(12) United States Patent
Takahashi et al.

(10) Patent No.: US 9,271,500 B2
(45) Date of Patent: Mar. 1, 2016

(54) FUSED HETEROCYCLIC COMPOUND

(71) Applicant: Sumitomo Chemical Company, Limited, Tokyo (JP)

(72) Inventors: Masaki Takahashi, Takarazuka (JP); Mai Ito, Takarazuka (JP); Yoshihiko Nokura, Takarazuka (JP); Takamasa Tanabe, Takarazuka (JP); Chie Shimizu, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/408,432

(22) PCT Filed: Jun. 10, 2013

(86) PCT No.: PCT/JP2013/066529
§ 371 (c)(1),
(2) Date: Dec. 16, 2014

(87) PCT Pub. No.: WO2013/191113
PCT Pub. Date: Dec. 27, 2013

(65) Prior Publication Data
US 2015/0181880 A1 Jul. 2, 2015

(30) Foreign Application Priority Data
Jun. 18, 2012 (JP) ................. 2012-136789

(51) Int. Cl.
| | | |
|---|---|---|
| C07D 419/02 | (2006.01) | |
| A61K 31/519 | (2006.01) | |
| A01N 43/90 | (2006.01) | |
| A01N 43/56 | (2006.01) | |
| C07D 231/56 | (2006.01) | |
| C07D 401/04 | (2006.01) | |
| C07D 471/04 | (2006.01) | |
| C07D 487/04 | (2006.01) | |

(52) U.S. Cl.
CPC ............... *A01N 43/90* (2013.01); *A01N 43/56* (2013.01); *C07D 231/56* (2013.01); *C07D 401/04* (2013.01); *C07D 471/04* (2013.01); *C07D 487/04* (2013.01)

(58) Field of Classification Search
None
See application file for complete search history.

(56) References Cited

U.S. PATENT DOCUMENTS

2014/0018373 A1  1/2014 Takyo et al.
2014/0194290 A1  7/2014 Takahashi et al.

FOREIGN PATENT DOCUMENTS

JP    2008-308448 A    12/2008
WO       0212236 A1    2/2002

OTHER PUBLICATIONS

CAPLUS 1965:82597.*
Almirante, L. et al., J.Med. Chem. (1965), 8(3), 305-12.*
Int'l Search Report issued Aug. 20, 2013 in Int'l Application No. PCT/JP2013/066529.
Almirante et al, "Derivatives of Imidazole. II. Synthesis and Reactions of Imidazo[1,2-alpha]pyrimidines and Other Bi- and Tricyclic Imidazo Derivatives with Analgesic, Antiinflammatory, Antipyretic, and Anticonvulsant Activity," Journal of Medicinal Chemistry, vol. 9, No. 1, pp. 29-33 (1966).
Almirante et al, "Derivatives of Imidazole. I. Synthesis and Reactions of Imidazo[1,2-alpha]pyridines with Analgesic, Antiinflammatory, Antypyretic, and Anticonvulsant Activity," Journal of Medicinal Chemistry, vol. 8, No. 3, pp. 305-312 (1965).
SciFinder File Registry No. 891743.
SciFinder File Registry No. 899363.

* cited by examiner

*Primary Examiner* — Heidi Reese
(74) *Attorney, Agent, or Firm* — Panitch Schwarze Belisario & Nadel LLP

(57) ABSTRACT

The fused heterocyclic compound represented by formula (1), or an N-oxide thereof, has excellent effectiveness in pest control.

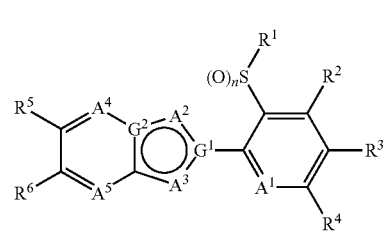

(1)

In the formula $G^1$ represents a nitrogen atom, etc.; $G^2$ represents a nitrogen atom, etc.; $A^1$ represents a nitrogen atom, etc.; $A^2$ represents a nitrogen atom, etc.; $A^3$ represents a nitrogen atom, etc.; $A^4$ represents a nitrogen atom, etc.; $A^5$ represents a nitrogen atom, etc.; $R^1$ represents a C1-C6 chain hydrocarbon group, etc., optionally having one or more atoms or groups selected from group X; $R^2$, $R^3$ and $R^4$ are the same or different, and represent a C1-C6 chain hydrocarbon group, etc., optionally having one or more atoms or groups selected from group X; $R^5$ and $R^6$ are the same or different, and represent a C1-C6 chain hydrocarbon group, etc., optionally having one or more atoms or groups selected from group X; and n represents 0, 1, 2.

6 Claims, No Drawings

FUSED HETEROCYCLIC COMPOUND

CROSS-REFERENCE TO RELATED APPLICATION

This application is a Section 371 of International Application No. PCT/JP2013/066529, filed Jun. 10, 2013, which was published in the Japanese language on Dec. 27, 2013, under International Publication No. WO 2013/191113 A1, and the disclosure of which is incorporated herein by reference.

TECHNICAL FIELD

The present invention relates to a certain kind of fused heterocyclic compounds and a use thereof for pest control.

BACKGROUND ART

Various fused heterocyclic compounds are known to have an activity as a medicine (for example, refer to Journal of Medicinal Chemistry, 8(3), 305(1965) and Journal of Medicinal Chemistry, 9(1), 29(1966)).

SUMMARY OF THE INVENTION

The present invention provides a compound having an excellent control effect on pests and a method for controlling pests using the compound.

More specifically, the present invention is as described below.

[1] A fused heterocyclic compound represented by formula (1) or an N-oxide thereof (hereinafter, referred to as compound of the present invention),

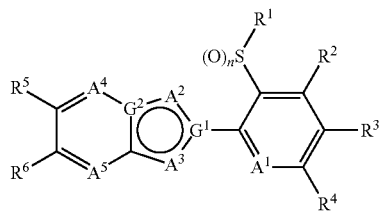

(1)

wherein $G^1$ represents a nitrogen atom or a carbon atom;
$G^2$ represents a nitrogen atom or a carbon atom (wherein one of
$G^1$ and $G^2$ is a nitrogen atom, and the other is a carbon atom);
$A^1$ represents a nitrogen atom or $CR^7$;
$A^2$ represents a nitrogen atom or $CR^8$;
$A^3$ represents a nitrogen atom or $CR^9$;
$A^4$ represents a nitrogen atom or $CR^{10}$;
A represents a nitrogen atom or $CR^1$;
$R^1$ represents a C1 to C6 chain hydrocarbon group optionally having one or more atoms or groups selected from group X or a C3 to C6 alicyclic hydrocarbon group optionally having one or more atoms or groups selected from group Y;
$R^2$, $R^3$, $R^4$ and $R^7$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-S(O)_2NR^{12}R^{13}$, $-NR^{12}R^{13}$, $-NR^{12}CO_2R^{13}$, $-NR^{12}C(O)R^{13}$, $-CO_2R^{12}$, $-C(O)R^{12}$, $-C(O)NR^{12}R^{13}$, $-SF_5$, a cyano group, a nitro group, a halogen atom, or a hydrogen atom;
$R^5$ and $R^6$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{14}$, $-S(O)_mR^{14}$, $-S(O)_2NR^{14}R^{15}$, $-NR^{14}R^{15}$, $-NR^{14}CO_2R^{15}$, $-NR^{14}C(O)R^{15}$, $-CO_2R^{14}$, $-C(O)R^{14}$, $-C(O)NR^{14}R^{15}$, $-SF_5$, a cyano group, a nitro group, a halogen atom, or a hydrogen atom;
$R^8$ and $R^9$ are the same or different and represent a C1 to C6 chain hydrocarbon group optionally having one or more atoms or groups selected from group X, a C3 to C6 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{16}$, $-S(O)_mR^{16}$, $-S(O)_2NR^{16}R^{17}$, $-NR^{16}R^{17}$, $-NR^{16}CO_2R^{17}$, $-NR^{16}C(O)R^{17}$, $-CO_2R^{16}$, $-C(O)R^{18}$, $-C(O)NR^{16}R^{17}$, a cyano group, a nitro group, a halogen atom, or a hydrogen atom;
$R^{10}$ and $R^{11}$ are the same or different and represent a C1 to C6 chain hydrocarbon group optionally having one or more halogen atoms, $-OR^{19}$, $-S(O)_mR^{19}$, $-NR^{19}R^{20}$, $-CO_2R^{19}$, $-C(O)R^{19}$, a cyano group, a nitro group, a halogen atom, or a hydrogen atom;
$R^{12}$, $R^{13}$, $R^{14}$, $R^{15}$, $R^{16}$, $R^{17}$, $R^{19}$ and $R^{20}$ are the same or different and represent a C1 to C6 chain hydrocarbon group optionally having one or more atoms or groups selected from group X, or a hydrogen atom;
$R^{18}$ represents a C1 to C6 chain hydrocarbon group optionally having one or more atoms or groups selected from group X;
each m independently represents 0, 1, or 2; and
n represents 0, 1, or 2;
wherein $R^5$ and $R^6$ do not simultaneously represent a hydrogen atom;
when $G^2$ is a nitrogen atom, and $R^5$ and $R^{11}$ are simultaneously a chlorine atom, $R^4$ does not represent a methyl group or a chlorine atom;
when m is 1 or 2 in $-S(O)_mR^{12}$, $R^{12}$ does not represent a hydrogen atom; when m is 1 or 2 in $-S(O)_mR^{14}$, $R^{14}$ does not represent a hydrogen atom; when m is 1 or 2 in $-S(O)_mR^{16}$, $R^{16}$ does not represent a hydrogen atom; and when m is 1 or 2 in $-S(O)_mR^{19}$, $R^{19}$ does not represent a hydrogen atom.

Group X: a group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, cyano groups, hydroxy groups, and halogen atoms.

Group Y: a group consisting of C1 to C6 chain hydrocarbon groups optionally having one or more halogen atoms, C1 to C6 alkoxy groups optionally having one or more halogen atoms, C2 to C6 alkenyloxy groups optionally having one or more halogen atoms, C2 to C6 alkynyloxy groups optionally having one or more halogen atoms, and halogen atoms.

Group Z: a group consisting of C1 to C6 chain hydrocarbon groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C1 to C6 alkylamino groups optionally having one or more halogen atoms, C2 to C8 dialkylamino groups optionally having one or more halogen atoms, halogen atoms, cyano groups, nitro groups, and $SF_5$.

[2] The compound according to [1],
wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a C3 to C6 cycloalkyl group optionally having one or more halogen atoms or one or more C1 to C3 alkyl groups;
$R^2$, $R^4$ and $R^7$ are the same or different and are a halogen atom or a hydrogen atom;
$R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered aromatic heterocyclic group (wherein the 5- or 6-membered aromatic heterocyclic group optionally has one or more atoms or groups selected from a group consisting of halogen atoms, C1 to C3 alkyl groups optionally having a halogen atom and C1 to C3 alkoxy groups optionally having a halogen atom), —$OR^{12}$ (wherein $R^{12}$ is a C1 to C6 alkyl group optionally having one or more halogen atoms), —$S(O)_mR^{12}$ (wherein $R^{12}$ is a C1 to C6 alkyl group optionally having one or more halogen atoms, and m is 0, 1, or 2), a cyano group, a nitro group, a halogen atom or a hydrogen atom;
either one of $R^5$ and $R^6$ is a C1 to C6 alkyl group optionally having one or more halogen atoms, —$OR^{14}$ (wherein $R^{14}$ is a C1 to C6 alkyl group optionally having one or more halogen atoms), —$S(O)_mR^{14}$ (wherein $R^{14}$ is a C1 to C6 alkyl group optionally having one or more halogen atoms, and m is 0, 1, or 2), $SF_5$, or a halogen atom, and the other is a halogen atom or a hydrogen atom;
$R^8$ and $R^9$ are the same or different and are a C1 to C6 alkyl group optionally having one or more halogen atoms, a halogen atom, or a hydrogen atom;
$R^{10}$ is a halogen atom or a hydrogen atom; and
$R^{11}$ is a C1 to C6 alkyl group optionally having one or more halogen atoms, —$OR^{19}$ (wherein $R^{19}$ is a C1 to C6 alkyl group optionally having one or more halogen atoms), —$S(O)_mR^{19}$ (wherein $R^{19}$ is a C1 to C6 alkyl group optionally having one or more halogen atoms, and m is 0, 1, or 2), a halogen atom, or a hydrogen atom.

[3] The compound according to [1] or [2],
wherein $R^1$ is an ethyl group, a cyclopropylmethyl group, or a cyclopropyl group;
$R^2$, $R^4$ and $R^7$ are a hydrogen atom;
$R^3$ is a C1 to C6 alkyl group optionally having one or more halogen atoms, —$OR^{12}$ (wherein $R^{12}$ is a C1 to C6 alkyl group optionally having one or more halogen atoms), —$S(O)_mR^{12}$ (wherein $R^{12}$ is a C1 to C6 alkyl group optionally having one or more halogen atoms, and m is 0, 1, or 2), a halogen atom, or a hydrogen atom; either one of $R^5$ and $R^6$ is a C1 to C6 haloalkyl group, —$OR^{14}$ (wherein $R^{14}$ is a C1 to C6 haloalkyl group), —$S(O)_mR^{14}$ (wherein $R^{14}$ is a C1 to C6 haloalkyl group, and m is 0, 1, or 2), $SF_5$, or a halogen atom, and the other is a halogen atom or a hydrogen atom;
$R^8$ and $R^9$ are the same or different and are a methyl group, a hydrogen atom, or a halogen atom; and
$R^{10}$ and $R^{11}$ are the same or different and are a halogen atom or a hydrogen atom.

[4] The compound according to any one of [1] to [3], wherein $G^1$ is a nitrogen atom.

[5] The compound according to any one of [1] to [3], wherein $G^1$ is a nitrogen atom; $A^2$ is a nitrogen atom; and $A^3$ is $CR^9$.

[6] The compound according to any one of [1] to [3], wherein $G^2$ is a nitrogen atom.

[7] The compound according to any one of [1] to [3], wherein $G^2$ is a nitrogen atom; $A^2$ is a nitrogen atom; and $A^3$ is $CR^9$.

[8] The compound according to any one of [1] to [3], wherein $G^2$ is a nitrogen atom; $A^2$ is $CR^8$; and $A^3$ is a nitrogen atom.

[9] The compound according to any one of [1] to [3], wherein $G^2$ is a nitrogen atom; $A^4$ is $CR^9$; and $A^5$ is a nitrogen atom.

[10] The compound according to any one of [1] to [3], wherein

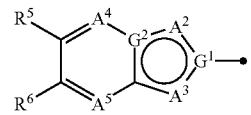

in the formula (1) is any of J1 to J6 as shown below:

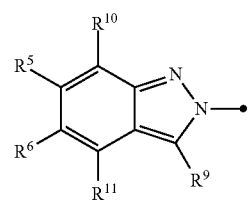

J1

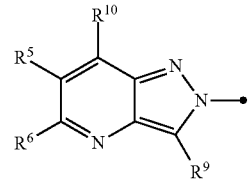

J2

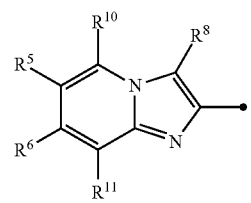

J3

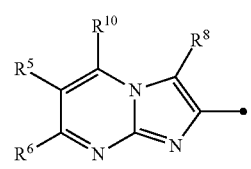

J4

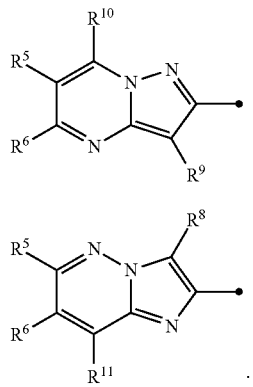

[11] A pest control composition comprising the compound as defined in any one of [1] to [10], and an inert carrier.
[12] A method for controlling pests comprising applying an effective amount of the compound as defined in any one of [1] to [10] to a pest or a place where a pest inhabits.

MODE FOR CARRYING OUT THE INVENTION

In the compound of the present invention, an N-oxide is a compound in which the nitrogen atom constituting the ring on the heterocyclic group is oxidized. Examples of the heterocyclic group that may form an N-oxide include a pyridine ring and fused rings containing a pyridine ring.

The groups used in the description of the present specification will be described below with examples.

The notation of "Ca to Cb chain hydrocarbon group" in the present specification represents a straight or branched saturated or unsaturated hydrocarbon group having the number of carbon atoms of a to b.

Examples of the "C1 to C6 chain hydrocarbon group" include C1 to C6 alkyl groups such as a methyl group, an ethyl group, a propyl group, an isopropyl group, a butyl group, an isobutyl group, a sec-butyl group, a tert-butyl group, a pentyl group, a neopentyl group and a hexyl group; C2 to C6 alkenyl groups such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group and a 1-hexenyl group; and C2 to C6 alkynyl groups such as an ethynyl group, a propargyl group, a 2-butynyl group, a 3-butynyl group, a 1-pentynyl group and a 1-hexynyl group.

The notation of "Ca to Cb alkyl group" in the present specification represents a straight or branched alkyl group having the number of carbon atoms of a to b.

Examples of the "C1 to C6 alkyl group" include a methyl group, an ethyl group, a propyl group, an isopropyl group, a butyl group, an isobutyl group, a sec-butyl group, a tert-butyl group, a pentyl group, a neopentyl group, and a hexyl group.

Examples of the "C2 to C6 alkyl group" include an ethyl group, a propyl group, an isopropyl group, a butyl group, an isobutyl group, a sec-butyl group, a tert-butyl group, a pentyl group, a neopentyl group, and a hexyl group.

Examples of the "C1 to C3 alkyl group" include a methyl group, an ethyl group, a propyl group, and an isopropyl group.

The notation of "Ca to Cb alkenyl group" in the present specification represents a straight or branched unsaturated hydrocarbon group having the number of carbon atoms of a to b, and having one or two or more double bonds in the molecule.

Examples of the "C2 to C6 alkenyl group" include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, and a 1-hexenyl group.

The notation of "Ca to Cb alkynyl group" in the present specification represents a straight or branched unsaturated hydrocarbon group having the number of carbon atoms of a to b, and having one or two or more triple bonds in the molecule.

Examples of the "C2 to C6 alkynyl group" include an ethynyl group, a propargyl group, a 2-butynyl group, a 3-butynyl group, a 1-pentynyl group, and a 1-hexynyl group.

The notation of "Ca to Cb haloalkyl group" in the present specification represents a straight or branched alkyl group having the number of carbon atoms of a to b, in which one or more hydrogen atoms bound to the carbon atom are substituted by a halogen atom, and at that time, when having two or more halogen atoms, those halogen atoms may be the same or different from each other.

Examples of the "C1 to C6 haloalkyl group" include a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the "C1 to C3 haloalkyl group" include the groups exemplified in the "C1 to C6 haloalkyl group" described above.

The "C1 to C6 perfluoroalkyl group" represents a straight or branched hydrocarbon group having the number of carbon atoms of 1 to 6, in which all hydrogen atoms bound to the carbon atom are substituted by a fluorine atom, and includes a trifluoromethyl group, a pentafluoroethyl group, a heptafluoropropyl group, and a heptafluoroisopropyl group.

Examples of the "C1 to C3 perfluoroalkyl group" include the groups exemplified in the "C1 to C6 perfluoroalkyl group" described above.

The notation of "Ca to Cb alkoxy group" in the present specification represents a straight or branched group represented by alkyl-O— having the number of carbon atoms of a to b.

Examples of the "C1 to C6 alkoxy group" include a methoxy group, an ethoxy group, a propoxy group, an isopropoxy group, a butoxy group, an isobutoxy group, a sec-butoxy group, a tert-butoxy group, a pentyloxy group, a neopentyloxy group, and a hexyloxy group.

Examples of the "C1 to C3 alkoxy group" include a methoxy group, an ethoxy group, a propoxy group, and an isopropoxy group.

The notation of "Ca to Cb alkenyloxy group" in the present specification represents a straight or branched group represented by alkenyl-O— having the number of carbon atoms of a to b, and having one or two or more double bonds in the molecule.

Examples of the "C2 to C6 alkenyloxy group" include a vinyloxy group, a 1-propenyloxy group, a 2-propenyloxy group, a 1-methylvinyloxy group, a 2-methyl-1-propenyloxy group, a 1-butenyloxy group, a 2-butenyloxy group, a 3-butenyloxy group, a 1-pentenyloxy group, and a 1-hexenyloxy group.

The notation of "Ca to Cb alkynyloxy group" in the present specification represents a straight or branched group represented by alkynyl-O— having the number of carbon atoms of a to b, and having one or two or more triple bonds in the molecule.

Examples of the "C2 to C6 alkynyloxy group" include an ethynyloxy group, a propargyloxy group, a 2-butynyloxy group, a 3-butynyloxy group, a 1-pentynyloxy group, and a 1-hexynyloxy group.

The notation of "Ca to Cb alkylsulfanyl group" in the present specification represents a straight or branched group represented by alkyl-S— having the number of carbon atoms of a to b.

Examples of the "C1 to C6 alkylsulfanyl group" include a methylsulfanyl group, an ethylsulfanyl group, a propylsulfanyl group, an isopropylsulfanyl group, a butylsulfanyl group, a pentylsulfanyl group, and a hexylsulfanyl group.

The notation of "Ca to Cb alkylsulfinyl group" in the present specification represents a straight or branched group represented by alkyl-S(O)— having the number of carbon atoms of a to b.

Examples of the "C1 to C6 alkylsulfinyl group" include a methylsulfinyl group, an ethylsulfinyl group, a propylsulfinyl group, an isopropylsulfinyl group, a butylsulfinyl group, a pentylsulfinyl group, and a hexylsulfinyl group.

The notation of "Ca to Cb alkylsulfonyl group" in the present specification represents a straight or branched group represented by alkyl-S(O)$_2$— having the number of carbon atoms of a to b.

Examples of the "C1 to C6 alkylsulfonyl group" include a methylsulfonyl group, an ethylsulfonyl group, a propylsulfonyl group, an isopropylsulfonyl group, a butylsulfonyl group, a pentylsulfonyl group, and a hexylsulfonyl group.

The notation of "Ca to Cb alkylcarbonyl group" in the present specification represents a straight or branched group represented by alkyl-C(O)— having the number of carbon atoms of a to b.

Examples of the "C2 to C6 alkylcarbonyl group" include an acetyl group, a propionyl group, a butyryl group, a pentanoyl group, and a hexanoyl group.

The notation of "Ca to Cb alkoxycarbonyl group" in the present specification represents a straight or branched group represented by alkyl-O—C(O)— having the number of carbon atoms of a to b.

Examples of the "C2 to C6 alkoxycarbonyl group" include a methoxycarbonyl group, an ethoxycarbonyl group, a propoxycarbonyl group, a butoxycarbonyl group, a pentyloxycarbonyl group, and a tert-butoxycarbonyl group.

The notation of "Ca to Cb alicyclic hydrocarbon group" in the present specification represents a cyclic nonaromatic hydrocarbon group having the number of carbon atoms of a to b.

Examples of the "C3 to C6 alicyclic hydrocarbon group" include a cyclopropyl group, a cyclobutyl group, a cyclopentyl group, a cyclohexyl group, a 1-cyclohexenyl group, a 2-cyclohexenyl group, and a 3-cyclohexenyl group.

The notation of "Ca to Cb cycloalkyl group" in the present specification represents a cyclic alkyl group having the number of carbon atoms of a to b.

The "C3 to C6 cycloalkyl group" includes a cyclopropyl group, a cyclobutyl group, a cyclopentyl group, and a cyclohexyl group.

The notation of "Ca to Cb alkylamino group" in the present specification represents a straight or branched group represented by alkyl-NH— having the number of carbon atoms of a to b.

Examples of the "C1 to C6 alkylamino group" include a methylamino group, an ethylamino group, a propylamino group, an isopropylamino group, and a butylamino group.

The notation of "Ca to Cb dialkylamino group" in the present specification represents a straight or branched dialkylamino group having a total number of carbon atoms of the alkyl groups of a to b, in which the number of carbon atoms of each alkyl group may be the same or different.

Examples of the "C2 to C8 dialkylamino group" include a dimethylamino group, a diethylamino group, and a dipropylamino group.

In the notation of "optionally having one or more atoms or groups selected from group X" in the present specification, when having two or more atoms or groups selected from group X, the atoms or groups selected from group X may be the same or different from each other.

In the notation of "optionally having one or more atoms or groups selected from group Y" in the present specification, when having two or more atoms or groups selected from group Y, the atoms or groups selected from group Y may be the same or different from each other.

In the notation of "optionally having one or more atoms or groups selected from group Z" in the present specification, when having two or more atoms or groups selected from group Z, the atoms or groups selected from group Z may be the same or different from each other.

In the notation of "optionally having one or more halogen atoms" in the present specification, when having two or more halogen atoms, those halogen atoms may be the same or different from each other.

The notation of "heterocyclic group" in the present specification represents a heterocyclic compound residue containing one or more atoms selected from the group consisting of a nitrogen atom, an oxygen atom and a sulfur atom, other than a carbon atom in the cyclic structure, and examples include a 5-membered heterocyclic group and a 6-membered heterocyclic group.

The "5-membered heterocyclic group" represents a 5-membered heterocyclic compound residue containing one or more atoms selected from the group consisting of a nitrogen atom, an oxygen atom and a sulfur atom, other than a carbon atom in the cyclic structure, and examples include a 5-membered aromatic heterocyclic group and a 5-membered nonaromatic heterocyclic group.

Examples of the "5-membered aromatic heterocyclic group" include a pyrrolyl group, a furyl group, a pyrazolyl group, a thienyl group, an imidazolyl group, a triazolyl group, a tetrazolyl group, and an isoxazolyl group.

Examples of the "5-membered nonaromatic heterocyclic group" include a pyrrolidinyl group, a pyrazolidinyl group, and a tetrahydrofuryl group.

The "6-membered heterocyclic group" represents a 6-membered heterocyclic compound residue containing one or more atoms selected from the group consisting of a nitrogen atom, an oxygen atom and a sulfur atom, other than a carbon atom, in the cyclic structure, and examples include a 6-membered aromatic heterocyclic group and a 6-membered nonaromatic heterocyclic group.

Examples of the "6-membered aromatic heterocyclic group" include a pyrazinyl group, a pyrimidinyl group, and a pyridyl group.

Examples of the "6-membered nonaromatic heterocyclic group" include a piperidyl group, a morpholinyl group, a piperazinyl group, and a thiomorpholinyl group.

The "halogen atom" in the present specification refers to a fluorine atom, a chlorine atom, a bromine atom, and an iodine atom.

The notation of the "C1 to C6 chain hydrocarbon group optionally having one or more atoms or groups selected from group X" in the compound of the present invention represents a straight or branched hydrocarbon group having a carbon atom number of 1 to 6, in which a hydrogen atom bound to the carbon atom is optionally substituted by an atom or group selected from group X, and at that time, when having two or more atoms or groups selected from group X, the atoms or groups selected from group X may be the same or different each other.

Examples of the "C1 to C6 chain hydrocarbon group optionally having one or more atoms or groups selected from group X" include C1 to C6 alkyl groups optionally having one or more atoms or groups selected from group X such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a trifluoromethyl group, a trichloromethyl group, a 2-fluoroethyl group, a 2,2-difluoroethyl group, a 2,2,2,-trifluoroethyl group, a pentafluoroethyl group, a methylsulfanylethyl group, an ethylsulfanylethyl group, a methylsulfinylethyl group, a methylsulfonylethyl group, a 2-hydroxyethyl group, a cyclopropylmethyl group, a 1-methylcyclopropylmethyl group, and a 2,2-difluorocyclopropylmethyl group; C2 to C6 alkenyl groups optionally having one or more atoms or groups selected from group X such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group X such as an ethynyl group, a propargyl group, a 2-butynyl group, a 3-butynyl group, a 1-pentynyl group, a 1-hexynyl group and a 4,4,4-trifluoro-2-butynyl group, and the "C1 to C6 chain hydrocarbon group optionally having one or more atoms or groups selected from group X" is selected in the range of each specified number of carbon atoms.

The notation of the "C3 to C6 alicyclic hydrocarbon group optionally having one or more atoms or groups selected from group Y" in the compound of the present invention represents a cyclic nonaromatic hydrocarbon group having a carbon atom number of 3 to 6, in which a hydrogen atom bound to the carbon atom is optionally substituted by an atom or group selected from group Y, and at that time, when having two or more atoms or groups selected from group Y, the atoms or groups selected from group Y may be the same or different each other.

Examples of the "C3 to C6 alicyclic hydrocarbon group optionally having one or more atoms or groups selected from group Y" include a cyclopropyl group, a cyclobutyl group, a cyclopentyl group, a cyclohexyl group, a 1-cyclohexenyl group, a 2-cyclohexenyl group, a 3-cyclohexenyl group, a 1-methylcyclohexyl group, a 2-methylcyclohexyl group, a 3-methylcyclohexyl group, a 4-methylcyclohexyl group, a 2-methoxylcyclohexyl group, a 3-methoxylcyclohexyl group, a 4-methoxylcyclohexyl group, a 1-fluorocyclohexyl group, a 2-fluorocyclohexyl group, a 3-fluorocyclohexyl group, and a 4-fluorocyclohexyl group.

The notation of the "C1 to C6 chain hydrocarbon group optionally having one or more halogen atoms" in the compound of the present invention represents a straight or branched hydrocarbon group having a carbon atom number of 1 to 6, in which a hydrogen atom bound to the carbon atom is optionally substituted by a halogen atom, and at that time, when having two or more halogen atoms, those halogen atoms may be the same or different each other.

Examples of the "C1 to C6 chain hydrocarbon group optionally having one or more halogen atoms" include C1 to C6 alkyl groups optionally having one or more halogen atoms such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group and a heptafluoroisopropyl group; C2 to C6 alkenyl groups optionally having one or more halogen atoms such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more halogen atoms such as an ethynyl group, a propargyl group, a 2-butynyl group, a 3-butynyl group, a 1-pentynyl group, a 1-hexynyl group and a 4,4,4-trifluoro-2-butynyl group, and the "C1 to C6 chain hydrocarbon group optionally having one or more halogen atoms" is selected in the range of each specified number of carbon atoms.

The notation of the "phenyl group optionally having one or more atoms or groups selected from group Z" in the compound of the present invention represents a phenyl group in which a hydrogen atom bound to the carbon atom is optionally substituted by an atom or group selected from group Z, and at that time, when having two or more atoms or groups selected from group Z, the atoms or groups selected from group Z may be the same or different each other.

Examples of the "phenyl group optionally having one or more atoms or groups selected from group Z" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-methoxycarbonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group, and a 4-methoxycarbonylphenyl group.

The notation of the "heterocyclic group" in the "5- or 6-membered heterocyclic group optionally having one or more atoms or groups selected from group Z" in the compound of the present invention represents a heterocyclic compound residue containing one or more atoms selected from the group consisting of a nitrogen atom, an oxygen atom and a sulfur atom, other than a carbon atom, in the cyclic structure, and at that time, when having two or more atoms or groups selected from group Z, the atoms or groups selected from group Z may be the same or different each other.

In the compound of the present invention, a 5- or 6-membered heterocyclic group means a 5- or 6-membered aromatic heterocyclic group or a 5- or 6-membered nonaromatic heterocyclic group.

Examples of the "5- or 6-membered heterocyclic group optionally having one or more atoms or groups selected from group Z" include 5- or 6-membered nonaromatic heterocyclic groups optionally having one or more atoms or groups selected from group Z such as a pyrrolidin-1-yl group, a 3,3,4,4-tetrafluoropyrrolidin-1-yl group, a tetrahydrofuran-2-yl group, a piperidyl group, a morpholinyl group and a thiomorpholinyl group; and 5- or 6-membered aromatic heterocyclic groups optionally having one or more atoms or groups selected from group Z such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazole-1-yl group, a 3-chloro-1,2,4-triazole-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidyl group, a 5-pyrimidyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidyl group, a 3-chloro-5-trifluoromethylpyridin-2-yl group and a 5-trifluoromethylpyridin-2-yl group.

Examples of the "5- or 6-membered aromatic heterocyclic group (wherein the 5- or 6-membered aromatic heterocyclic group may have one or more atoms or groups selected from the group consisting of halogen atoms, C1 to C3 alkyl groups optionally having a halogen atom, and C1 to C3 alkoxy groups optionally having a halogen atom)" in the compound of the present invention include a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 5-bromo-2-furyl group, a 5-methoxy-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidyl group, a 5-pyrimidyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidyl group, a 3-chloro-5-trifluoromethylpyridin-2-yl group and a 5-trifluoromethylpyridin-2-yl group.

Examples of the "C1 to C6 alkyl group optionally having one or more atoms or groups selected from the group consisting of halogen atoms and a cyclopropyl group (wherein the cyclopropyl group may have one or more halogen atoms or one or more C1 to C3 alkyl groups)" in the compound of the present invention include a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, a heptafluoroisopropyl group, a cyclopropylmethyl group, a 2-cyclopropylethyl group, a 1-cyclopropylethyl group, and a 1-methylcyclopropylmethyl group.

Examples of the "C1 to C6 alkoxy groups optionally having one or more halogen atoms" in the compound of the present invention include a methoxy group, a trifluoromethoxy group, an ethoxy group, a 2,2,2-trifluoroethoxy group, a propoxy group, an isopropoxy group, a butoxy group, an isobutoxy group, a sec-butoxy group, a tert-butoxy group, a pentyloxy group, and a hexyloxy group.

Examples of the "C2 to C6 alkenyloxy groups optionally having one or more halogen atoms" in the compound of the present invention include a 2-propenyloxy group, a 2-methyl-2-propenyloxy group, a 2-butenyloxy group, a 3-butenyloxy group, a 2-pentenyloxy group, a 2-hexenyloxy group, a 3,3-difluoroallyloxy group, and a 3,3-dichloroallyloxy group.

Examples of the "C2 to C6 alkynyloxy groups optionally having one or more halogen atoms" in the compound of the present invention include a propargyloxy group, a 2-butynyloxy group, a 3-butynyloxy group, a 2-pentynyloxy group, a 2-hexynyloxy group, and a 4,4,4-trifluoro-2-butynyloxy group.

Examples of the "C1 to C6 alkylsulfanyl groups optionally having one or more halogen atoms" in the compound of the present invention include a methylsulfanyl group, an ethylsulfanyl group, a propylsulfanyl group, an isopropylsulfanyl group, a butylsulfanyl group, a pentylsulfanyl group, a hexylsulfanyl group, a trifluoromethylsulfanyl group, a 2,2,2-trifluoroethylsulfanyl group, and a pentafluoroethylsulfanyl group.

Examples of the "C1 to C6 alkylsulfinyl groups optionally having one or more halogen atoms" in the compound of the present invention include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

Examples of the "C1 to C6 alkylsulfonyl groups optionally having one or more halogen atoms" in the compound of the present invention include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, and a pentafluoroethylsulfonyl group.

Examples of the "C2 to C6 alkylcarbonyl groups optionally having one or more halogen atoms" in the compound of the present invention include an acetyl group, a propionyl group, a butyryl group, a pentanoyl group, a hexanoyl group, and a trifluoroacetyl group.

Examples of the "C2 to C6 alkoxycarbonyl groups optionally having one or more halogen atoms" in the compound of the present invention include a methoxycarbonyl group, an ethoxycarbonyl group, a propoxycarbonyl group, a butoxycarbonyl group, a pentyloxycarbonyl group, a tert-butoxycarbonyl group, and a 2,2,2-trifluoroethoxycarbonyl group.

Examples of the "C1 to C6 alkylamino groups optionally having one or more halogen atoms" in the compound of the present invention include a methylamino group, an ethylamino group, a 2,2,2-trifluoroethylamino group, a propylamino group, an isopropylamino group, and a butylamino group.

Examples of the "C2 to C8 dialkylamino groups optionally having one or more halogen atoms" in the compound of the present invention include a dimethylamino group, a diethylamino group, a bis(2,2,2-trifluoroethyl)amino group, and a dipropylamino group.

Examples of the "C3 to C6 cycloalkyl groups optionally having one or more halogen atoms or one or more C1 to C3 alkyl groups" in the compound of the present invention include a cyclopropyl group, a 1-methylcyclopropyl group, a 2-methylcyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

Examples of the "C4 to C9 cyclopropylalkyl groups (wherein the cyclopropyl group optionally has one or more halogen atoms or one or more C1 to C3 alkyl groups)" in the compound of the present invention include a cyclopropylmethyl group, a 2-cyclopropylethyl group, a 1-cyclopropylethyl group, and a 1-methylcyclopropyl group.

Examples of the "C1 to C6 alkyl group optionally having one or more halogen atoms" in the compound of the present invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the "C2 to C6 alkenyl group optionally having one or more halogen atoms" in the compound of the present invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the "C2 to C6 alkynyl group optionally having one or more halogen atoms" in the compound of the present invention include an ethynyl group, a propargyl group, a 2-butynyl group, a 3-butynyl group, a 1-pentynyl group, a 1-hexynyl group, and a 4,4,4-trifluoro-2-butynyl group.

Examples of the "pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom)" in the compound of the present invention include a 2-pyridyl group, a 3-pyridyl group, a 4-pyridyl group, a 5-trifluoromethyl-2-pyridyl group, and a 3-chloro-5-trifluoromethyl-2-pyridyl group.

Examples of the "pyrimidyl group (wherein the pyrimidyl group optionally has one or more atoms or substituents selected from the group consisting of halogen atoms, C1 to C3 alkyl groups optionally having a halogen atom, and C1 to C3 alkoxy groups optionally having a halogen atom)" in the compound of the present invention include a 2-pyrimidyl group, a 4-pyrimidyl group, a 5-pyrimidyl group, and a 2-chloro-4-pyrimidyl group.

Examples of the compound of the present invention include the following compounds.

In the formula (1), compounds wherein $G^1$ is a nitrogen atom.

In the formula (1), compounds wherein $G^1$ is a nitrogen atom, $A^2$ is a nitrogen atom, and $A^3$ is $CR^9$.

In the formula (1), compounds wherein $G^2$ is a nitrogen atom.

In the formula (1), compounds wherein $G^2$ is a nitrogen atom, $A^2$ is a nitrogen atom, and $A^3$ is $CR^9$.

In the formula (1), compounds wherein $G^2$ is a nitrogen atom, $A^2$ is $CR^8$, and $A^3$ is a nitrogen atom.

In the formula (1), compounds wherein $G^2$ is a nitrogen atom, $A^4$ is $CR^9$, and $A^5$ is a nitrogen atom.

In the formula (1), compounds wherein

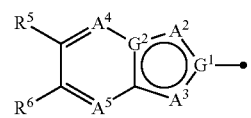

is J1 to J6 as shown below

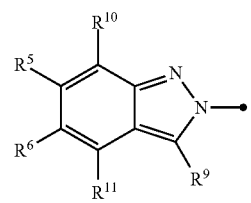

J1

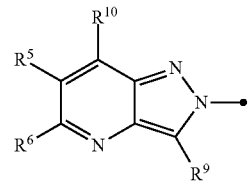

J2

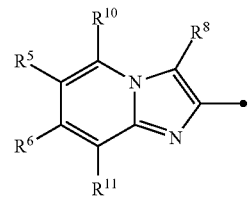

J3

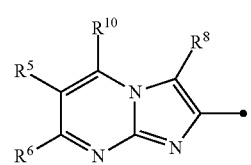

J4

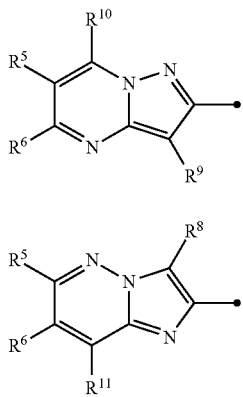

wherein symbols represent the same meaning as in the formula (1).

In the formula (1), compounds wherein

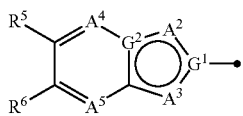

is J1', J2', J3'-1, J3'-2, J4'-1, J4'-2, J5'-1, J5'-2, J6'-1 and J6'-2 as shown below

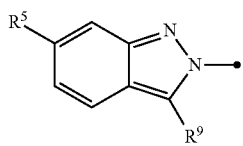

J1'

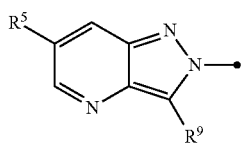

J2'

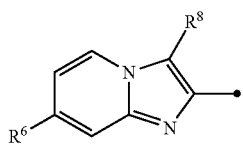

J3'-1

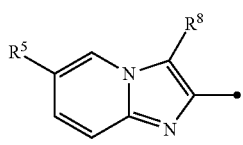

J3'-2

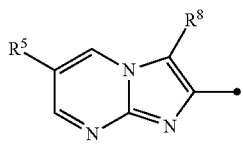

J4'-1

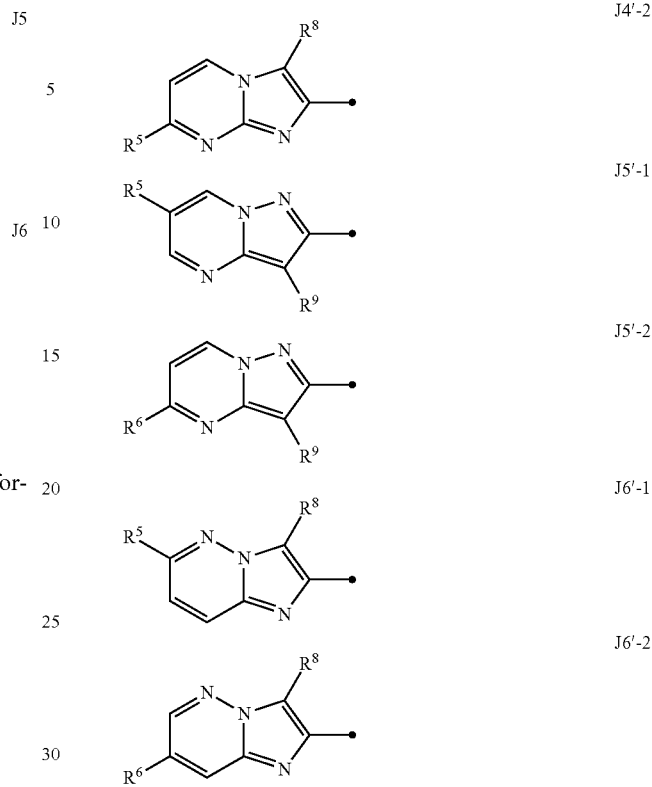

wherein symbols represent the same meaning as in the formula (1).

In the formula (1), compounds wherein $R^1$ is a C1 to C6 chain hydrocarbon group optionally having one or more atoms or groups selected from group X;

In the formula (1), compounds wherein $R^1$ is a C1 to C6 alkyl group optionally having one or more atoms or groups selected from the group consisting of halogen atoms and a cyclopropyl group (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms;

In the formula (1), compounds wherein $R^1$ is a C1 to C6 alkyl group optionally having one or more atoms or groups selected from the group consisting of halogen atoms and a cyclopropyl group (wherein the cyclopropyl group optionally has one or more halogen atoms or one or more C1 to C3 alkyl groups);

In the formula (1), compounds wherein $R^1$ is a C1 to C6 alkyl group, a C1 to C6 haloalkyl group, or a C4 to C9 cyclopropylalkyl group (wherein the cyclopropyl group optionally has one or more halogen atoms or one or more C1 to C3 alkyl groups);

In the formula (1), compounds wherein $R^1$ is a C2 to C6 alkyl group, a C1 to C6 haloalkyl group, or a C4 to C9 cyclopropylalkyl group (wherein the cyclopropyl group optionally has one or more halogen atoms or one or more C1 to C3 alkyl groups);

In the formula (1), compounds wherein $R^1$ is a C3 to C6 alicyclic hydrocarbon group, optionally having one or more atoms or groups selected from group Y;

In the formula (1), C3 to C6 cycloalkyl groups optionally having one or more halogen atoms or one or more C1 to C3 alkyl groups;

In the formula (1), compounds wherein $R^1$ is a methyl group, an ethyl group, a propyl group, an isopropyl group, a trifluoromethyl group, a 2,2,2-trifluoroethyl group, a cyclopropylmethyl group, a cyclopropyl group, a 2-methylyclopropyl group, or a 2,2-difluorocyclopropyl group;

In the formula (1), compounds wherein $R^1$ is an ethyl group, a cyclopropylmethyl group, or a cyclopropyl group;

In the formula (1), compounds wherein $R^1$ is an ethyl group;

In the formula (1), compounds wherein, when $A^1$ is $CR^7$, $R^2$, $R^4$ and $R^7$ are the same or different and are a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{12}$, $-S(O)_m R^{12}$, $-SF_5$, a cyano group, a nitro group, a halogen atom, or a hydrogen atom;

In the formula (1), compounds wherein, when $A^1$ is $CR^7$, $R^2$, $R^4$ and $R^7$ are the same or different and are a C1 to C6 alkyl group optionally having one or more halogen atoms, $-OR^{12}$ (wherein $R^{12}$ is a C1 to C6 alkyl group optionally having one or more halogen atoms), $-S(O)_m R^{12}$ (wherein $R^{12}$ is a C1 to C6 alkyl group optionally having one or more halogen atoms), a halogen atom, or a hydrogen atom;

In the formula (1), compounds wherein, when $A^1$ is $CR^7$, $R^2$, $R^4$ and $R^7$ are the same or different and are a halogen atom or a hydrogen atom;

In the formula (1), compounds wherein, when $A^1$ is $CR^7$, $R^2$, $R^4$ and $R^7$ are all a hydrogen atom;

In the formula (1), compounds wherein, when $A^1$ is a nitrogen atom, $R^2$ and $R^4$ are the same or different and are a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{12}$, $-S(O)_m R^{12}$, $-SF_5$, a cyano group, a nitro group, a halogen atom, or a hydrogen atom;

In the formula (1), compounds wherein, when $A^1$ is a nitrogen atom, $R^2$ and $R^4$ are the same or different and are a C1 to C6 alkyl group optionally having one or more halogen atoms, $-OR^{12}$ (wherein $R^{12}$ is a C1 to C6 alkyl group optionally having one or more halogen atoms), $-S(O)_m R^{12}$ (wherein $R^{12}$ is a C1 to C6 alkyl group optionally having one or more halogen atoms), a halogen atom, or a hydrogen atom;

In the formula (1), compounds wherein, when $A^1$ is a nitrogen atom, $R^2$ and $R^4$ are the same or different and are a halogen atom or a hydrogen atom;

In the formula (1), compounds wherein, when $A^1$ is a nitrogen atom, $R^2$ and $R^4$ are both a hydrogen atom;

In the formula (1), compounds wherein $R^3$ is a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{12}$, $-S(O)_m R^{12}$, $-SF_5$, a cyano group, a nitro group, a halogen atom, or a hydrogen atom;

In the formula (1), compounds wherein $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered aromatic heterocyclic group (wherein the 5- or 6-membered aromatic heterocyclic group optionally has one or more atoms or substituents selected from a group consisting of halogen atoms, C1 to C3 alkyl groups optionally having a halogen atom and C1 to C3 alkoxy groups optionally having a halogen atom), $-OR^{12}$ (wherein $R^{12}$ is a C1 to C6 alkyl group optionally having one or more halogen atoms), $-S(O)_m R^{12}$ (wherein $R^{12}$ is a C1 to C6 alkyl group optionally having one or more halogen atoms), a cyano group, a nitro group, a halogen atom, or a hydrogen atom;

In the formula (1), compounds wherein $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom), a pyrimidyl group (wherein the pyrimidyl group optionally has one or more atoms or substituents selected from the group consisting of halogen atoms, C1 to C3 alkyl groups optionally having a halogen atom, and C1 to C3 alkoxy groups optionally having a halogen atom), $-OR^{12}$ (wherein $R^{12}$ is a C1 to C6 alkyl group optionally having one or more halogen atoms), $-S(O)_m R^{12}$ (wherein $R^{12}$ is a C1 to C6 alkyl group optionally having one or more halogen atoms), a halogen atom, or a hydrogen atom;

In the formula (1), compounds wherein $R^3$ is a C1 to C6 alkyl group optionally having one or more halogen atoms, $-OR^{12}$ (wherein $R^{12}$ is a C1 to C6 alkyl group optionally having one or more halogen atoms), $-S(O)_m R^{12}$ (wherein $R^{12}$ is a C1 to C6 alkyl group optionally having one or more halogen atoms), a halogen atom, or a hydrogen atom;

In the formula (1), compounds wherein $R^3$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, $-CF_2CF_3$, $-CF_2CF_2CF_3$, $-CF(CF_3)_2$, $-CF_2CF_2CF_2CF_3$, $-OCF_3$, $-OCF_2CF_3$, $-SCF_3$, $-S(O)CF_3$, $-S(O)_2CF_3$, $-SCF_2CF_3$, $-S(O)\ CF_2CF_3$, $-S(O)_2CF_2CF_3$, a 2-pyridyl group, a 5-trifluoromethyl-2-pyridyl group, a 2-pyrimidyl group, a fluorine atom, a chlorine atom, a bromine atom, an iodine atom, or a hydrogen atom;

In the formula (1), compounds wherein $R^3$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, $-CF_2CF_3$, $-CF_2CF_2CF_3$, $-CF(CF_3)_2$, $-CF_2CF_2CF_2CF_3$, $-OCF_3$, $-OCF_2CF_3$, $-SCF_3$, $-S(O)CF_3$, $-S(O)_2CF_3$, $-SCF_2CF_3$, $-S(O)\ CF_2CF_3$, $-S(O)_2CF_2CF_3$, a fluorine atom, a chlorine atom, a bromine atom, an iodine atom, or a hydrogen atom;

In the formula (1), compounds wherein $R^3$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, $-CF_2CF_3$, $-CF_2CF_2CF_3$, $-CF(CF_3)_2$, $-CF_2CF_2CF_2CF_3$, $-OCF_3$, $-OCF_2CF_3$, $-SCF_3$, $-S(O)CF_3$, $-S(O)_2CF_3$, $-SCF_2CF_3$, $-S(O)\ CF_2CF_3$, $-S(O)_2CF_2CF_3$, a fluorine atom, a chlorine atom, a bromine atom, or an iodine atom;

In the formula (1), compounds wherein $R^5$ and $R^6$ are the same or different and are a C1 to C6 chain hydrocarbon group optionally having one or more atoms or groups selected from group X, $-OR^{14}$, $-S(O)_m R^{14}$, $-SF_5$, a halogen atom, or a hydrogen atom;

In the formula (1), compounds wherein $R^5$ and $R^6$ are the same or different and are a C1 to C6 alkyl group optionally having one or more halogen atoms, —OR$^{14}$ (wherein R$^{14}$ is a C1 to C6 alkyl group optionally having one or more halogen atoms), —S(O)$_m$R$^{14}$ (wherein R$^{14}$ is a C1 to C6 alkyl group optionally having one or more halogen atoms), —SF$_5$, a halogen atom, or a hydrogen atom;

In the formula (1), compounds wherein either one of R$^5$ and R$^6$ is a C1 to C6 chain hydrocarbon group optionally having one or more atoms or groups selected from group X, —OR$^{14}$, —S(O)$_m$R$^{14}$, —SF$_5$, or a halogen atom, and the other is a halogen atom or a hydrogen atom;

In the formula (1), compounds wherein either one of R$^5$ and R$^6$ is a C1 to C6 alkyl group optionally having one or more halogen atoms, —OR$^{14}$ (wherein R$^{14}$ is a C1 to C6 alkyl group optionally having one or more halogen atoms), —S(O)$_m$R$^{14}$ (wherein R$^{14}$ is a C1 to C6 alkyl group optionally having one or more halogen atoms), —SF$_5$, or a halogen atom, and the other is a halogen atom or a hydrogen atom;

In the formula (1), compounds wherein either one of R$^5$ and R$^6$ is a C1 to C6 haloalkyl group, —OR$^{14}$ (wherein R$^{14}$ is a C1 to C6 haloalkyl group), —S(O)$_m$R$^{14}$ (wherein R$^{14}$ is a C1 to C6 haloalkyl group), —SF$_5$, or a halogen atom, and the other is a halogen atom or a hydrogen atom;

In the formula (1), compounds wherein either one of R$^5$ and R$^6$ is a C1 to C6 haloalkyl group, —OR$^{14}$ (wherein R$^{14}$ is a C1 to C6 haloalkyl group), —S(O)$_m$R$^{14}$ (wherein R$^{14}$ is a C1 to C6 haloalkyl group) or —SF$_5$, and the other is a halogen atom or a hydrogen atom;

In the formula (1), compounds wherein either one of R$^5$ and R$^6$ is a C1 to C6 haloalkyl group, —OR$^{14}$ (wherein R$^{14}$ is a C1 to C6 haloalkyl group), —S(O)$_m$R$^{14}$ (wherein R$^{14}$ is a C1 to C6 haloalkyl group) or a halogen atom, and the other is a halogen atom or a hydrogen atom;

In the formula (1), compounds wherein either one of R$^5$ and R$^6$ is a C1 to C6 haloalkyl group, —OR$^{14}$ (wherein R$^{14}$ is a C1 to C6 haloalkyl group), or —S(O)$_m$R$^{14}$ (wherein R$^{14}$ is a C1 to C6 haloalkyl group), and the other is a halogen atom or a hydrogen atom;

In the formula (1), compounds wherein either one of R$^5$ and R$^6$ is a C1 to C6 perfluoroalkyl group, —OR$^{14}$ (wherein R$^{1'}$ is a C1 to C6 perfluoroalkyl group), or —S(O)$_m$R$^1$ (wherein R$^{14}$ is a C1 to C6 perfluoroalkyl group), and the other is a halogen atom or a hydrogen atom;

In the formula (1), compounds wherein either one of R$^5$ and R$^6$ is a trifluoromethyl group, —CF$_2$CF$_3$, —CF$_2$CF$_2$CF$_3$, —CF(CF$_3$)$_2$, —OCF$_3$, —OCF$_2$CF$_3$, —SCF$_3$, —S(O)CF$_3$, —S(O)$_2$CF$_3$, —SCF$_2$CF$_3$, —S(O) CF$_2$CF$_3$, —S(O)$_2$CF$_2$CF$_3$, SF$_5$, a fluorine atom, a chlorine atom, a bromine atom, or an iodine atom, and the other is a halogen atom or a hydrogen atom;

In the formula (1), compounds wherein either one of R$^5$ and R$^6$ is a trifluoromethyl group, —CF$_2$CF$_3$, —CF$_2$CF$_2$CF$_3$, —CF(CF$_3$)$_2$, —OCF$_3$, —OCF$_2$CF$_3$, —SCF$_3$, —S(O)$_2$CF$_3$— SCF$_2$CF$_3$, —S(O)CF$_2$CF$_3$, —S(O)$_2$CF$_2$CF$_3$, SF$_5$, a fluorine atom, a chlorine atom, a bromine atom, or an iodine atom, and the other is a hydrogen atom;

In the formula (1), compounds wherein, when A$^2$ is CR$^8$, R$^8$ is a C1 to C6 chain hydrocarbon group optionally having one or more atoms or groups selected from group X, —OR$^{16}$, —S(O)$_m$R$^{16}$, —NR$^{16}$R$^{17}$, a halogen atom, or a hydrogen atom;

In the formula (1), compounds wherein, when A$^2$ is CR$^8$, R$^8$ is a C1 to C6 alkyl group optionally having one or more halogen atoms, —OR$^{16}$ (wherein R$^{16}$ is a C1 to C6 alkyl group optionally having one or more halogen atoms), —S(O)$_m$R$^{16}$ (wherein R$^{16}$ is a C1 to C6 alkyl group optionally having one or more halogen atoms), a halogen atom, or a hydrogen atom;

In the formula (1), compounds wherein, when A$^2$ is CR$^8$, R$^8$ is a methyl group, a halogen atom or a hydrogen atom;

In the formula (1), compounds wherein, when A$^2$ is CR$^8$, R$^8$ is a hydrogen atom;

In the formula (1), compounds wherein, when A$^3$ is CR$^9$, R$^9$ is a C1 to C6 chain hydrocarbon group optionally having one or more atoms or groups selected from group X, —OR$^{16}$, —S(O)$_m$R$^{16}$, —NR$^{16}$R$^{17}$, a halogen atom, or a hydrogen atom;

In the formula (1), compounds wherein, when A$^3$ is CR$^9$, R$^9$ is a C1 to C6 alkyl group optionally having one or more halogen atoms, —OR$^{16}$ (wherein R$^{16}$ is a C1 to C6 alkyl group optionally having one or more halogen atoms), —S(O)$_m$R$^{16}$ (wherein R$^{16}$ is a C1 to C6 alkyl group optionally having one or more halogen atoms), a halogen atom, or a hydrogen atom;

In the formula (1), compounds wherein, when A$^3$ is CR$^9$, R$^9$ is a methyl group, a halogen atom or a hydrogen atom;

In the formula (1), compounds wherein, when A$^3$ is CR$^9$, R$^9$ is a hydrogen atom;

In the formula (1), compounds wherein, when A$^4$ is CR$^{10}$, R$^{10}$ is a C1 to C6 chain hydrocarbon group optionally having one or more halogen atoms, —OR$^{19}$, —S(O)$_m$R$^{19}$, a halogen atom, or a hydrogen atom;

In the formula (1), compounds wherein, when A$^4$ is CR$^{10}$, R$^{10}$ is a C1 to C6 alkyl group optionally having one or more halogen atoms, —OR$^{19}$ (wherein R$^{19}$ is a C1 to C6 alkyl group optionally having one or more halogen atoms), —S(O) R$^{19}$ (wherein R$^{19}$ is a C1 to C6 alkyl group optionally having one or more halogen atoms), a halogen atom, or a hydrogen atom;

In the formula (1), compounds wherein, when A$^4$ is CR$^{10}$, R$^{10}$ is a halogen atom or a hydrogen atom;

In the formula (1), compounds wherein, when A$^4$ is CR$^{10}$, R$^{10}$ is a hydrogen atom;

In the formula (1), compounds wherein, when A$^5$ is CR$^{11}$, R$^{11}$ is a C1 to C6 chain hydrocarbon group optionally having one or more halogen atoms, —OR$^{19}$, —S(O)$_m$R$^{19}$, a halogen atom, or a hydrogen atom;

In the formula (1), compounds wherein, when A$^5$ is CR$^{11}$, R$^{11}$ is a C1 to C6 alkyl group optionally having one or more halogen atoms, —OR$^{19}$ (wherein R$^{19}$ is a C1 to C6 alkyl group optionally having one or more halogen atoms), —S(O)$_m$R$^{19}$ (wherein R$^{19}$ is a C1 to C6 alkyl group optionally having one or more halogen atoms), a halogen atom, or a hydrogen atom;

In the formula (1), compounds wherein, when A$^5$ is CR$^{11}$, R$^{11}$ is a halogen atom or a hydrogen atom;

In the formula (1), compounds wherein, when A$^5$ is CR$^{11}$, R$^{11}$ is a hydrogen atom;

In the formula (1), compounds wherein A$^1$ is CR$^7$;

In the formula (1), compounds wherein A$^1$ is a nitrogen atom;

In the formula (1), compounds wherein A$^2$ is CR$^8$;

In the formula (1), compounds wherein A$^2$ is a nitrogen atom;

In the formula (1), compounds wherein A$^3$ is CR$^9$;

In the formula (1), compounds wherein A$^3$ is a nitrogen atom;

In the formula (1), compounds wherein A$^4$ is CR$^{10}$ (particularly CH), and A$^5$ is CR$^{11}$ (particularly CH);

In the formula (1), compounds wherein A$^4$ is CR$^{10}$ (particularly CH), and A$^5$ is a nitrogen atom;

In the formula (1), compounds wherein A$^4$ is a nitrogen atom, and A$^5$ is CR$^{11}$ (particularly CH);

In the formula (1), compounds wherein n is 0;

In the formula (1), compounds wherein n is 1;

In the formula (1), compounds wherein n is 2;

In the formula (1), compounds wherein $R^2$ and $R^4$ are a hydrogen atom, $A^1$ is a nitrogen atom or $CR^7$ (particularly CH), and

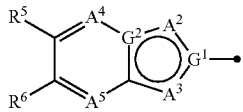

in the formula (1) is J1', J2', J3'-1, J3'-2, J4'-1, J4'-2, J5'-1, J5'-2, J6'-1 and J6'-2 as shown below

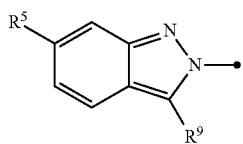
J1'

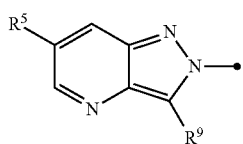
J2'

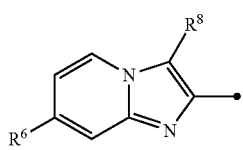
J3'-1

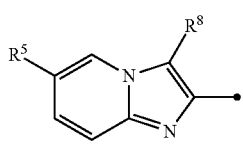
J3'-2

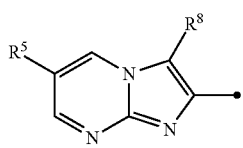
J4'-1

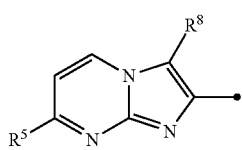
J4'-2

J5'-1

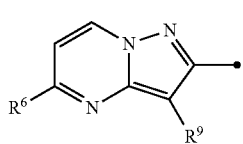
J5'-2

-continued

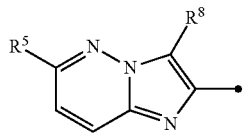
J6'-1

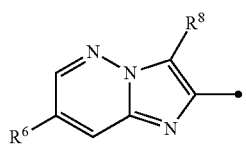
J6'-2 wherein symbols represent the same meaning as in the formula (1);

In the formula (1), compounds wherein $A^1$ is a nitrogen atom or CH, $A^2$ is a nitrogen atom or $CR^8$, $R^8$ is a C1 to C6 alkyl group optionally having one or more halogen atoms, a halogen atom, or a hydrogen atom, $A^3$ is a nitrogen atom or $CR^9$, $R^9$ is a C1 to C6 alkyl group optionally having one or more halogen atoms, a halogen atom, or a hydrogen atom, $A^4$ and $A^5$ are the same or different, and are a nitrogen atom or CH, $R^2$ and $R^4$ are a hydrogen atom, and $R^3$ is a C1 to C6 alkyl group optionally having one or more halogen atoms, $-OR^{12}$ (wherein $R^{12}$ is a C1 to C6 alkyl group optionally having one or more halogen atoms), $-S(O)_m R^{12}$ (wherein $R^{12}$ is a C1 to C6 alkyl group optionally having one or more halogen atoms), a halogen atom, or a hydrogen atom.

In the formula (1), compounds wherein $G^1$ represents a nitrogen atom or a carbon atom, $G^2$ represents a nitrogen atom or a carbon atom (wherein either one of $G^1$ and $G^2$ is a nitrogen atom, and the other is a carbon atom), $A^1$ is $CR^7$, $A^2$ is a nitrogen atom or $CR^8$, $A^3$ is a nitrogen atom or $CR^9$, $A^4$ is $CR^{10}$, $A^5$ is $CR^{11}$, $R^1$ is a C1 to C6 chain hydrocarbon group optionally having a halogen atom, $R^2$, $R^3$ and $R^4$ are the same or different, and are a C1 to C6 chain hydrocarbon group optionally having a halogen atom or a hydrogen atom, $R^5$ and $R^6$ are the same or different, and are a C1 to C6 chain hydrocarbon group optionally having a halogen atom, or a hydrogen atom, $R^7$ is a hydrogen atom, $R^8$ is a hydrogen atom, $R^9$ is a halogen atom or a hydrogen atom, $R^{10}$ and $R^{11}$ are a hydrogen atom, and n represents 0, 1 or 2 (wherein $R^5$ and $R^6$ do not simultaneously represent a hydrogen atom).

In the formula (1), compounds wherein $R^1$ is a C1 to C3 alkyl group, a C1 to C3 haloalkyl group, a C4 to C6 cyclopropylalkyl group, or a C3 to C6 cycloalkyl group, $R^2$ and $R^4$ are a hydrogen atom, $R^3$ is a C1 to C3 alkyl group, a C1 to C3 haloalkyl group (particularly, a C1 to C3 perfluoroalkyl group), $-OR^{12}$ (wherein $R^{12}$ is a C1 to C3 haloalkyl group, particularly a C1 to C3 perfluoroalkyl group such as $-CF_3$ and $-CF_2CF_3$), $-S(O)_m R^{16}$ (wherein $R^{16}$ is a C1 to C3 haloalkyl group, particularly, a C1 to C3 perfluoroalkyl group such as —CF₃ and —CF₂CF₃, and m is 0, 1 or 2), a halogen atom, or a hydrogen atom, and

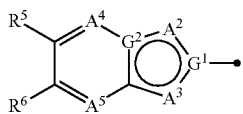

is J1 to J6 as shown below

J1
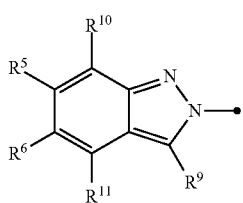

J2
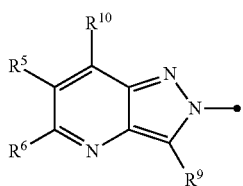

J3
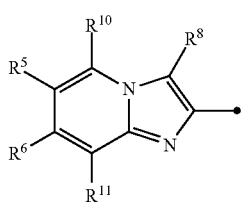

J4
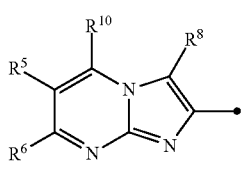

J5
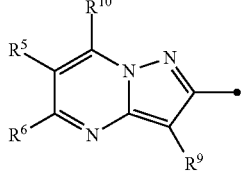

J6
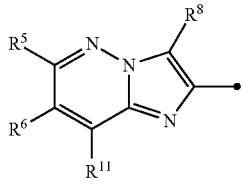

wherein,
R⁵ is a C1 to C3 alkyl group, a C1 to C3 haloalkyl group (particularly, a C1 to C3 perfluoroalkyl group such as —CF₃ and —CF₂CF₃), a halogen atom, or a hydrogen atom, R⁶ is a C1 to C3 alkyl group, a C1 to C3 haloalkyl group (particularly, a C1 to C3 perfluoroalkyl group such as —CF₃ and —CF₂CF₃), or a hydrogen atom, R⁷, R¹⁰ and R¹¹ are a hydrogen atom, and R⁸ and R⁹ are the same or different, and are a C1 to C3 alkyl group, a halogen atom, or a hydrogen atom, wherein R⁵ and R⁶ do not simultaneously represent a hydrogen atom.

In the formula (1), compounds wherein

R¹ is a C1 to C3 alkyl group, a C1 to C3 haloalkyl group, a C4 to C6 cyclopropylalkyl group, or a C3 to C6 cycloalkyl group,
R² and R⁴ are a hydrogen atom, R³ is a C1 to C3 alkyl group, a C1 to C3 haloalkyl group (particularly, a C1 to C3 perfluoroalkyl group), —OR¹² (wherein R¹² is a C1 to C3 haloalkyl group, particularly, a C1 to C3 perfluoroalkyl group such as —CF₃ and —CF₂CF₃), —S(O)ₘR¹⁶ (wherein R¹⁶ is a C1 to C3 haloalkyl group, particularly, a C1 to C3 perfluoroalkyl group such as —CF₃ and —CF₂CF₃, and m is 0, 1 or 2), a halogen atom, or a hydrogen atom, and

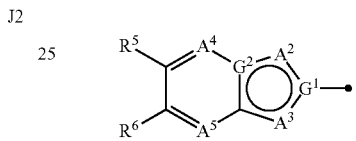

is J1', J2', J3'-1, J3'-2, J4'-1, J4'-2, J5'-1, J5'-2, J6'-1 and J6'-2 as shown below J1'
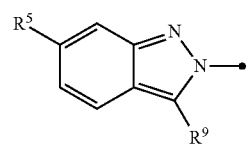

J2'

J3'-1
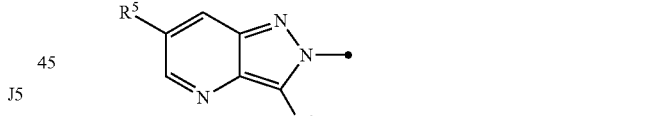

J3'-2

J4'-1

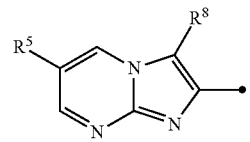

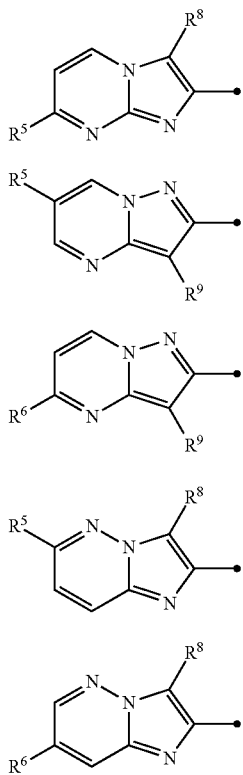

wherein $R^5$ is a C1 to C3 alkyl group, a C1 to C3 haloalkyl group (particularly, a C1 to C3 perfluoroalkyl group such as —$CF_3$ and —$CF_2CF_3$), or a halogen atom, $R^6$ is a C1 to C3 alkyl group, or a C1 to C3 haloalkyl group (particularly, a C1 to C3 perfluoroalkyl group such as —$CF_3$ and —$CF_2CF_3$), and $R^8$ and $R^9$ are the same or different, and are a C1 to C3 alkyl group, a halogen atom, or a hydrogen atom.

In the formula (1), compounds wherein $R^1$ is a C1 to C3 alkyl group (particularly, an ethyl group), $R^2$ and $R^4$ are a hydrogen atom, $R^3$ is a C1 to C3 alkyl group, a C1 to C3 haloalkyl group (particularly, a C1 to C3 perfluoroalkyl group such as —$CF_3$), or a hydrogen atom, and

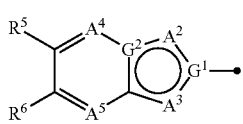

is J1', J2', J3'-1, J3'-2, J4'-1, J4'-2, J5'-1, J5'-2, J6'-1 and J6'-2 (particularly, J1', J3'-1, J3'-2, J4'-1, J5'-1) as shown below

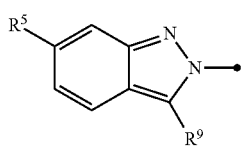

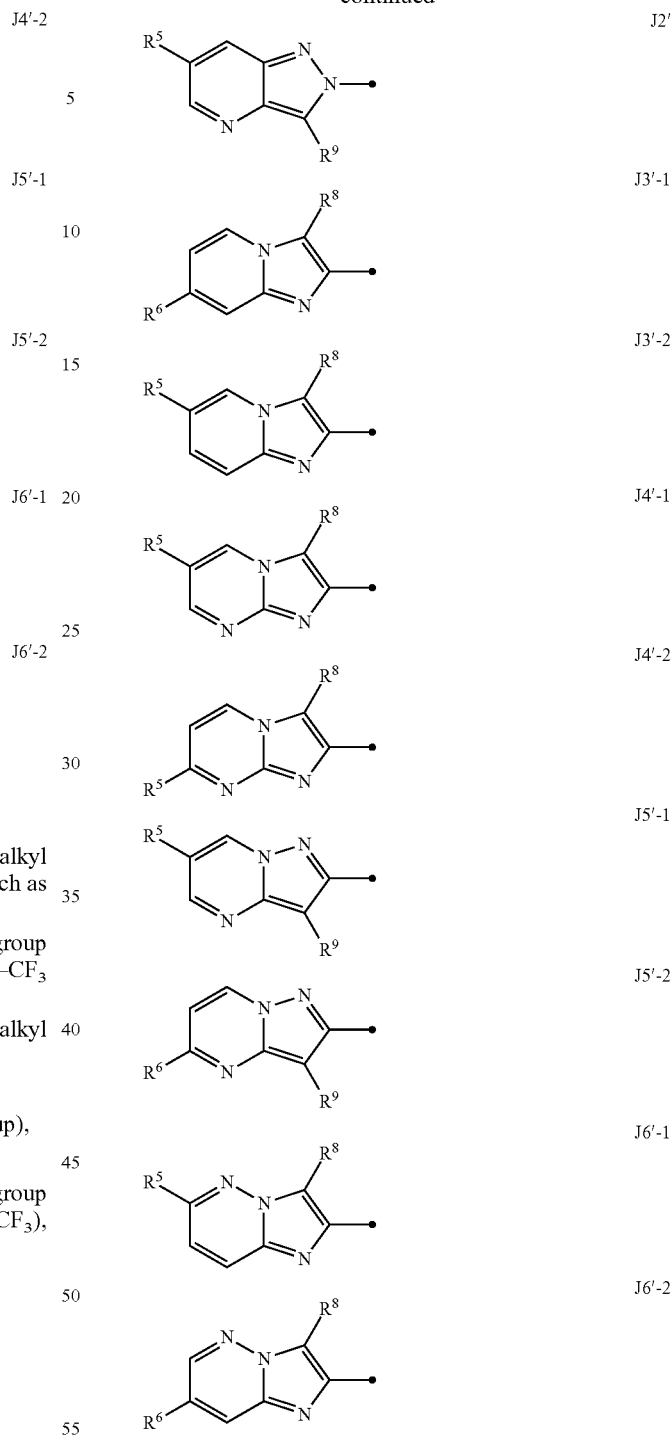

wherein $R^5$ is a C1 to C3 alkyl group, a C1 to C3 haloalkyl group (particularly, a C1 to C3 perfluoroalkyl group such as —$CF_3$ and —$CF_2CF_3$), or a halogen atom, $R^6$ is a C1 to C3 alkyl group or a C1 to C3 haloalkyl group (particularly, a C1 to C3 perfluoroalkyl group such as —$CF_3$ and —$CF_2CF_3$), and $R^8$ and $R^9$ are the same or different, and are a halogen atom or a hydrogen atom.

Next, the method for producing the compound of the present invention will be described.

The compound of the present invention and an intermediate compound can be produced, for example, according to the following (Production Method 1) to (Production Method 10).
(Production Method 1)

The compound of the present invention (P1) in which $G^1$ and $A^2$ are a nitrogen atom, $G^2$ is a carbon atom, and $A^3$ is CH in the formula (1) can be produced according to the following scheme:

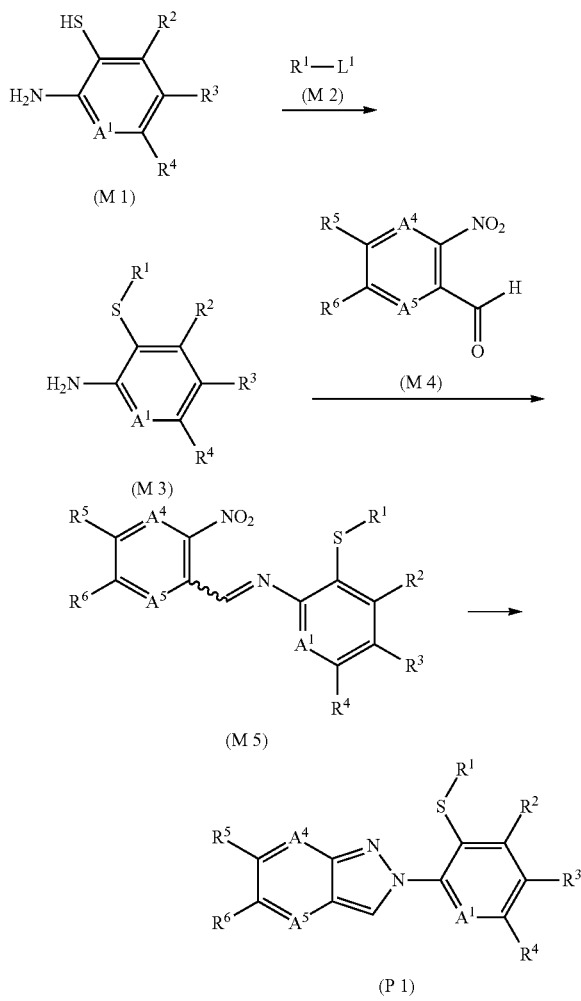

wherein $L^1$ represents a leaving group such as a chlorine atom, a bromine atom, an iodine atom, a trifluoromethanesulfonyloxy group or a methanesulfonyloxy group, and other symbols represent the same meaning as in the formula (1).

The intermediate compound (M3) can be produced by reacting the compound (M1) with the compound (M2), in the presence of a base.

The reaction is usually carried out in the presence of a solvent.

Examples of the solvent include ethers such as tetrahydrofuran (hereinafter, referred to as THF), ethylene glycol dimethyl ether, tert-butyl methyl ether and 1,4-dioxane, alcohols such as methanol and ethanol, aromatic hydrocarbons such as toluene and xylene, nitriles such as acetonitrile, aprotic polar solvents such as N,N-dimethylformamide (hereinafter, referred to as DMF), N-methyl pyrrolidone (hereinafter, referred to as NMP), 1,3-dimethyl-2-imidazolidinone (hereinafter, referred to as DMI) and dimethyl sulfoxide (hereinafter, referred to as DMSO), water, and mixtures thereof.

Examples of the base include hydrides of alkali metals and alkaline earth metals such as sodium hydride, potassium hydride and calcium hydride, inorganic bases such as sodium carbonate and potassium carbonate, and organic bases such as triethylamine.

In the reaction, the compound (M2) is usually used in a ratio of 0.8 to 1.2 mol, and the base is usually used in a ratio of 0.8 to 1.2 mol, based on 1 mol of the compound (M1).

The reaction temperature is usually within the range of 0 to 100° C. The reaction time is usually within the range of 0.1 to 24 hours.

After completion of the reaction, the intermediate compound (M3) can be isolated by subjecting it to usual post-treatment operations. The intermediate compound (M3) also can be further purified by chromatography, recrystallization, or the like.

The intermediate compound (M5) can be produced by dehydration condensing the intermediate compound (M3) with the intermediate compound (M4).

The reaction is usually carried out in the presence or absence of a solvent.

Examples of the solvent include aromatic hydrocarbons such as benzene, toluene and xylene, and mixtures thereof.

The reaction can be also carried out by adding an acid catalyst as necessary. Examples of the acid catalyst include hydrochloric acid, sulfuric acid, p-toluenesulfonic acid, and pyridinium p-toluenesulfonate.

In the reaction, the compound (M4) is usually used in a ratio of 1 to 2 mol, and the acid catalyst is usually used in a ratio of 0.01 to 1 mol, based on 1 mol of the compound (M3).

The reaction temperature is usually within the range of 0 to 150° C. The reaction time is usually within the range of 0.1 to 24 hours.

After completion of the reaction, the intermediate compound (M5) can be isolated by subjecting it to usual post-treatment operations. The isolated intermediate compound (M5) also can be further purified by chromatography, recrystallization, or the like.

The compound of the present invention (P1) can be produced by reacting the intermediate compound (M5) with triethyl phosphite.

The reaction is usually carried out in the presence or absence of a solvent.

Examples of the solvent include acetonitrile.

In the reaction, triethyl phosphite is usually used in an excess amount, based on 1 mol of the compound (M5), and the amount can be appropriately changed.

The reaction temperature is usually within the range of 80 to 160° C. The reaction time is usually within the range of 0.1 to 24 hours.

After completion of the reaction, the compound of the present invention (P1) can be isolated by subjecting it to usual post-treatment operations. The compound of the present invention (P1) also can be further purified by chromatography, recrystallization, or the like.

(Production Method 2)

The compound of the present invention (P2) in which $G^1$ is a carbon atom, $G^2$ and $A^3$ are a nitrogen atom, $A^2$ is CH, and $A^4$ is $CR^{10}$ in the formula (1) can be produced according to the following scheme:

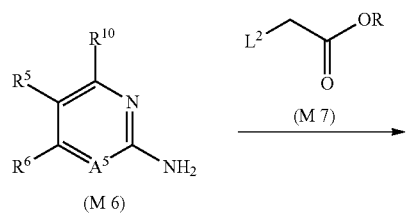
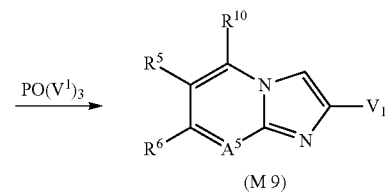
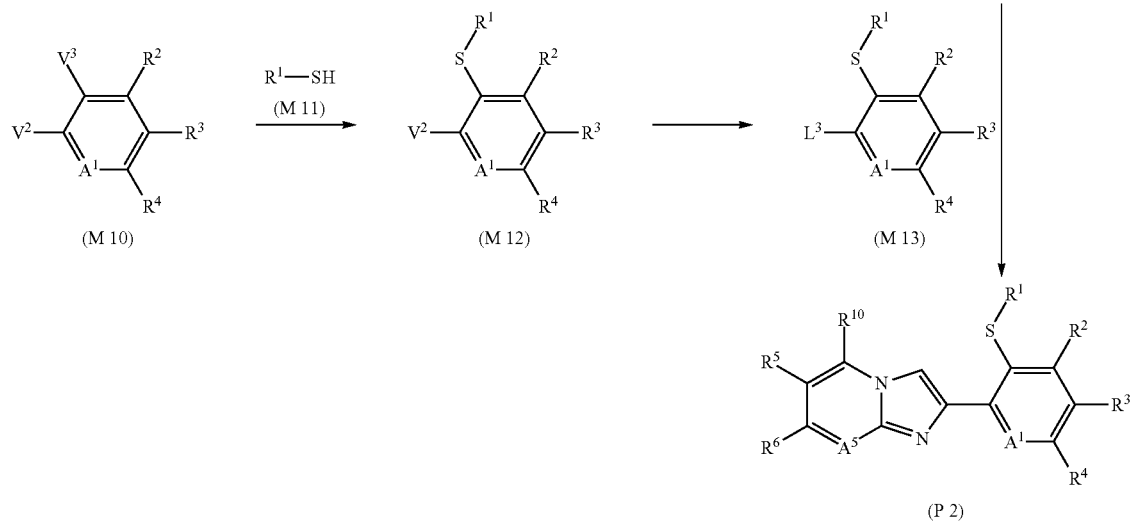

wherein R represents a methyl group or an ethyl group, $L^2$ represents a chlorine atom or a bromine atom, $L^3$ represents a $B(OH)_2$ group or a $B(OR^f)_2$ group (wherein two $R^f$'s are combined to form a $C(CH_3)_2C(CH_3)_2$— group), $V^1$ represents a chlorine atom or a bromine atom, $V^2$ represents a bromine atom or an iodine atom, $V^3$ represents a halogen atom such as a fluorine atom, a chlorine atom or a bromine atom, and other symbols represent the same meaning as in the formula (1).

The intermediate compound (M8) can be produced by reacting the compound (M6) with the compound (M7).

The reaction is usually carried out in the presence or absence of a solvent.

Examples of the solvent include alcohols such as methanol and ethanol, aromatic hydrocarbons such as toluene and xylene, and mixtures thereof.

In the reaction, the compound (M7) is usually used in a ratio of 1 to 10 mol, based on 1 mol of the compound (M6).

The reaction temperature is usually within the range of 0 to 200° C. The reaction time is usually within the range of 0.1 to 24 hours.

After completion of the reaction, the intermediate compound (M8) can be isolated by subjecting it to usual post-treatment operations. The isolated intermediate compound (M8) also can be further purified by recrystallization or the like.

The intermediate compound (M9) can be produced by reacting the intermediate compound (M8) with phosphorus oxychloride or phosphorus oxybromide.

The reaction is usually carried out in the presence or absence of a solvent.

Examples of the solvent include nitriles such as acetonitrile and propionitrile, aromatic hydrocarbons such as toluene and xylene, and mixtures thereof.

In the reaction, phosphorus oxychloride or phosphorus oxybromide is usually used in a ratio of 1 to 10 mol, based on 1 mol of the intermediate compound (M8).

The reaction temperature is usually within the range of 60 to 120° C. The reaction time is usually within the range of 0.1 to 24 hours.

After completion of the reaction, the intermediate compound (M9) can be isolated by subjecting it to usual post-treatment operations. The isolated intermediate compound (M9) also can be further purified by recrystallization, chromatography, or the like.

The intermediate compound (M12) can be produced by reacting the compound (M10) with the compound (M11) in the presence of a base.

The reaction is usually carried out in the presence of a solvent.

Examples of the solvent include ethers such as THF, ethylene glycol dimethyl ether, tert-butyl methyl ether and 1,4-dioxane, alcohols such as methanol and ethanol, aromatic hydrocarbons such as toluene and xylene, nitriles such as acetonitrile, aprotic polar solvents such as DMF, NMP, DMI and DMSO, water, and mixtures thereof.

Examples of the base include hydrides of alkali metals and alkaline earth metals such as sodium hydride, potassium hydride and calcium hydride, inorganic bases such as sodium carbonate and potassium carbonate, and organic bases such as triethylamine.

In the reaction, the compound (M11) is usually used in a ratio of 0.8 to 1.2 mol, and the base is usually used in a ratio of 0.8 to 1.2 mol, based on 1 mol of the compound (M10).

The reaction temperature is usually within the range of 0 to 100° C. The reaction time is usually within the range of 0.1 to 24 hours.

After completion of the reaction, the intermediate compound (M12) can be isolated by subjecting it to usual post-treatment operations. The intermediate compound (M12) also can be further purified by chromatography, recrystallization, or the like.

In the reaction, $V^3$ is preferably a fluorine atom or a chlorine atom.

The intermediate compound (M13) can be prepared by reacting the intermediate compound (M12) with an alkyllithium compound, then reacting the produced reaction intermediate with isopropoxyboronic acid pinacol ester or reacting the produced reaction intermediate with trialkyl borate and then hydrolyzing the reactant.

The reaction is usually carried out in the presence of a solvent.

Examples of the solvent include ethers such as diethyl ether, THF, ethylene glycol dimethyl ether, tert-butyl methyl ether and 1,4-dioxane, aromatic hydrocarbons such as toluene and xylene, and mixtures thereof.

Examples of the alkyllithium compound include n-, sec- and tert-butyllithium.

Examples of the trialkyl borate include trimethyl borate, triethyl borate, and triisopropyl borate.

In the reaction, the alkyllithium compound is usually used in a ratio of 1 mol, based on 1 mol of the intermediate compound (M12), but the amount can be appropriately changed.

In the reaction, the isopropoxyboronic acid pinacol ester or trialkyl borate is usually used in a ratio of 1 mol, based on 1 mol of the intermediate compound (M12), but the amount can be appropriately changed.

The reaction temperature in the reaction of the intermediate compound (M12) with the alkyllithium compound is usually within the range of −78 to 20° C., and the reaction time is usually within the range of 0.1 to 12 hours.

The reaction temperature in the reaction of the reaction intermediate with the isopropoxyboronic acid pinacol ester or trialkyl borate is usually within the range of −78° C. to 40° C., and the reaction time is usually within the range of 0.1 to 24 hours.

After completion of the reaction, the intermediate compound (M13) can be isolated by subjecting it to usual post-treatment operations. The isolated intermediate compound (M13) also can be further purified by recrystallization, chromatography, or the like.

The intermediate compound (M13) in which $L^3$ is a $B(OR^f)_2$ group (wherein two $R^f$s are combined to form a —$C(CH_3)_2C(CH_3)_2$— group) can be produced by reacting the intermediate compound (M12) with bis(pinacolato)diboron in the presence of a catalyst and a base.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, and mixtures thereof.

Examples of the catalyst include palladium catalysts such as tetrakis(triphenylphosphine)palladium, a [1,1'-bis(diphenylphosphino)ferrocene]dichloropalladium methylene chloride complex, and tris(dibenzylideneacetone) dipalladium (0).

In the reaction, a ligand can be also added as necessary. Examples of the ligand include tricyclohexylphosphine.

Examples of the base include potassium acetate.

In the reaction, bis(pinacolato)diboron is usually used in a ratio of 1 to 2 mol, the palladium catalyst is usually used in a ratio of 0.0001 to 0.1 mol, the ligand is usually used in a ratio of 0.0002 to 0.2 mol, and the base is usually used in a ratio of 1 to 5 mol, based on 1 mol of the intermediate compound (M12).

The reaction temperature is usually within the range of 50 to 120° C. The reaction time is usually within the range of 0.1 to 24 hours.

After completion of the reaction, the intermediate compound (M13) can be isolated by subjecting it to usual post-treatment operations. The isolated intermediate compound (M13) also can be further purified by recrystallization, chromatography, or the like.

The compound of the present invention (P2) can be produced by reacting the intermediate compound (M9) with the intermediate compound (M13) in the presence of a catalyst and a base.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, aprotic polar solvents such as DMF, water, and mixtures thereof.

Examples of the catalyst include palladium catalysts such as tetrakis(triphenylphosphine)palladium, a [1,1'-bis(diphenylphosphino)ferrocene]dichloropalladium methylene chloride complex, and tris(dibenzylideneacetone) dipalladium (0).

In the reaction, a ligand can be also added as necessary. Examples of the ligand include tricyclohexylphosphine and X-Phos(2-dicyclohexylphosphino-2',4',6'-triisopropylbiphenyl).

Examples of the base include inorganic bases such as sodium hydroxide, potassium hydroxide, potassium carbonate, cesium carbonate, potassium tert-butoxide and potassium phosphate, and organic acid salts such as sodium acetate and potassium acetate.

In the reaction, the intermediate compound (M13) is usually used in a ratio of 1 to 3 mol, the palladium catalyst is usually used in a ratio of 0.0001 to 0.1 mol, the ligand is usually used in a ratio of 0.0002 to 0.2 mol, and the base is usually used in a ratio of 1 to 10 mol, based on 1 mol of the intermediate compound (M9).

The reaction temperature is usually within the range of 50 to 150° C. The reaction time is usually within the range of 0.1 to 24 hours.

After completion of the reaction, the compound of the present invention (P2) can be isolated by subjecting it to usual post-treatment operations. The isolated compound of the present invention (P2) also can be further purified by recrystallization, chromatography, or the like.

(Production Method 3)

The compound of the present invention (P3) in which $G^1$ is a carbon atom, $G^2$ and $A^3$ are a nitrogen atom, and $A^2$ is $CR^8$ in the formula (1) can be produced according to the following scheme:

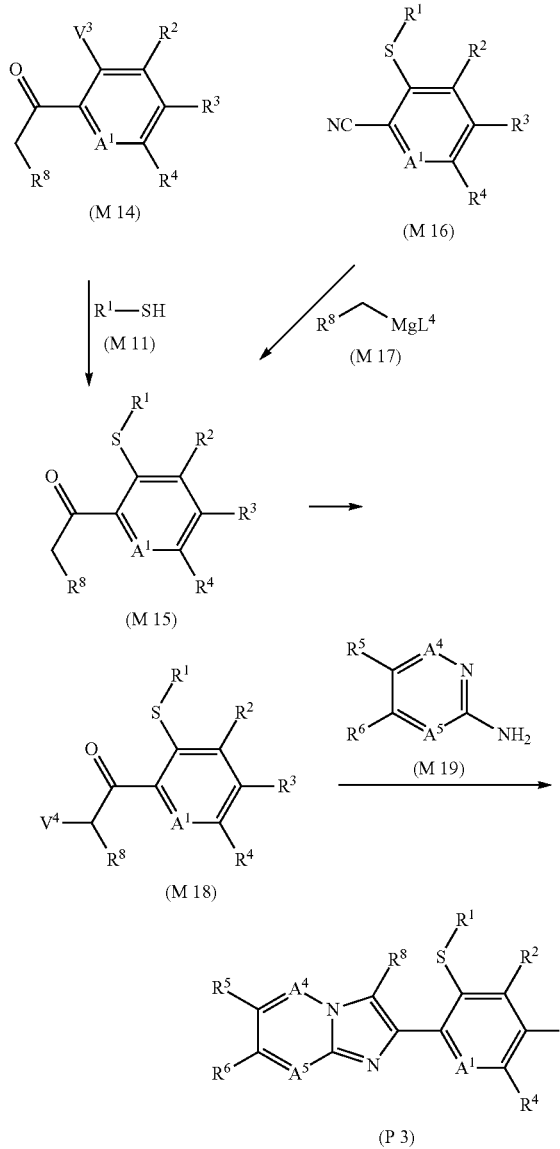

(M 14)
(M 16)
(M 11)
(M 17)
(M 15)
(M 19)
(M 18)
(P 3)

wherein L⁴ represents a chlorine atom, a bromine atom or an iodine atom, V³ represents a halogen atom, V⁴ represents a chlorine atom or a bromine atom, and other symbols represent the same meaning as in the formula (1).

The intermediate compound (M15) can be produced according to Production Method 2, using the compound (M14) in place of the intermediate compound (M10).

In the reaction, V³ is preferably a fluorine atom or a chlorine atom.

The intermediate compound (M15) can be produced by reacting the compound (M16) with the compound (M17).

Examples of the solvent include ethers such as THF, ethylene glycol dimethyl ether, tert-butyl methyl ether and 1,4-dioxane, aromatic hydrocarbons such as toluene and xylene, and mixtures thereof.

In the reaction, the compound (M17) is usually used in a ratio of 0.9 to 1.2 mol, based on 1 mol of the compound (M16).

The reaction temperature is usually within the range of −20 to 100° C. The reaction time is usually within the range of 0.1 to 24 hours.

After completion of the reaction, the intermediate compound (M15) can be isolated by subjecting it to usual post-treatment operations. The intermediate compound (M15) also can be further purified by chromatography, recrystallization, or the like.

The intermediate compound (M18) can be produced by reacting the intermediate compound (M15) with a chlorinating agent or a brominating agent.

The reaction is usually carried out in the presence of a solvent.

Examples of the solvent include aliphatic halogenated hydrocarbons such as dichloromethane, chloroform and carbon tetrachloride, alcohols such as methanol and ethanol, ethers such as diethyl ether, THF, ethylene glycol dimethyl ether, tert-butyl methyl ether and 1,4-dioxane, aprotic polar solvents such as DMF, NMP, DMI and DMSO, acetic acid, water, and mixtures thereof.

Examples of the chlorinating agent include chlorine and N-chlorosuccinimide, and examples of the brominating agent include bromine, N-bromosuccinimide, tetrabutylammonium tribromide and phenyltrimethylammonium tribromide.

In the reaction, a catalytic amount of aluminum chloride or hydrogen bromide can be also added as necessary.

In the reaction, the chlorinating agent or brominating agent is usually used in a ratio of 0.9 to 1.2 mol, based on 1 mol of the intermediate compound (M15).

The reaction temperature is usually within the range of 0 to 150° C. The reaction time is usually within the range of 0.5 to 24 hours.

After completion of the reaction, the intermediate compound (M18) can be isolated by subjecting it to usual post-treatment operations. Alternatively, after completion of the present reaction, the intermediate compound (M18) can be subjected to the next reaction, without isolation.

The compound of the present invention (P3) can be produced by reacting the intermediate compound (M18) with the compound (M19) in the presence of a base.

The reaction is usually carried out in the presence of a solvent.

Examples of the solvent include aliphatic halogenated hydrocarbons such as dichloromethane, chloroform and carbon tetrachloride, alcohols such as methanol and ethanol, ethers such as diethyl ether, THF, ethylene glycol dimethyl ether, tert-butyl methyl ether and 1,4-dioxane, aprotic polar solvents such as DMF, NMP, DMI and DMSO, water, and mixtures thereof.

Examples of the base include inorganic bases such as sodium bicarbonate, sodium carbonate and potassium carbonate, and organic bases such as triethylamine.

In the reaction, the compound (M19) is usually used in a ratio of 1 to 2 mol, and the base is usually used in a ratio of 1 to 5 mol, based on 1 mol of the intermediate compound (M18).

The reaction temperature is usually within the range of 0 to 150° C. The reaction time is usually within the range of 0.1 to 24 hours.

After completion of the reaction, the compound of the present invention (P3) can be isolated by subjecting it to usual post-treatment operations. The isolated compound of the present invention (P3) also can be further purified by chromatography, recrystallization, or the like.

(Production Method 4)

The compound of the present invention (P4) in which $G^1$ is a carbon atom, $G^2$, $A^2$ and $A^5$ are a nitrogen atom, $A^3$ is $CR^9$, and $A^4$ is $CR^{10}$ in the formula (1) can be produced according to the following scheme:

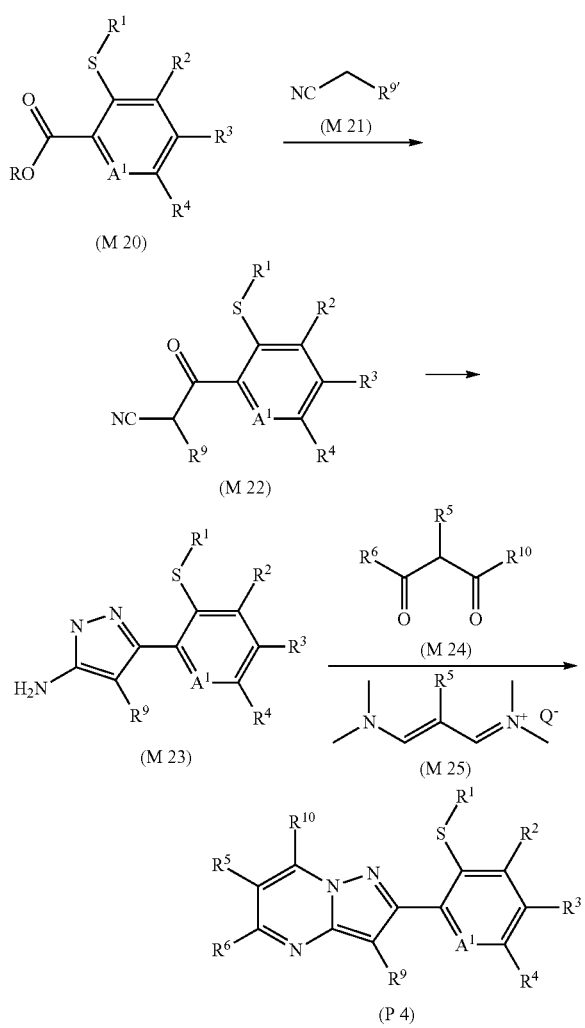

wherein R represents a methyl group or an ethyl group, Q represents Cl or PF$_6$, and other symbols represent the same meaning as in the formula (1).

The intermediate compound (M22) can be produced by reacting the compound (M20) with the compound (M21) in the presence of a base.

The reaction is usually carried out in the presence of a solvent.

Examples of the solvent include aliphatic halogenated hydrocarbons such as dichloromethane and chloroform, aromatic hydrocarbons such as toluene and xylene, ethers such as diethyl ether, THF, ethylene glycol dimethyl ether, tert-butyl methyl ether and 1,4-dioxane, aprotic polar solvents such as DMF, NMP, DMI and DMSO, and mixtures thereof.

Examples of the base include hydrides of alkali metals or alkaline earth metals such as sodium hydride, potassium hydride and calcium hydride, inorganic bases such as sodium carbonate and potassium carbonate, organic bases such as triethylamine, and potassium tert-butoxide.

In the reaction, the compound (M21) is usually used in a ratio of 1 to 5 mol, and the base is usually used in a ratio of 1 to 10 mol, based on 1 mol of the intermediate compound (M20).

The reaction temperature is usually within the range of 0 to 150° C. The reaction time is usually within the range of 0.1 to 24 hours.

After completion of the reaction, the intermediate compound (M22) can be isolated by subjecting it to usual post-treatment operations. The isolated intermediate compound (M22) also can be further purified by chromatography, recrystallization, or the like.

The intermediate compound (M23) can be produced by reacting the intermediate compound (M22) with hydrazine.

The reaction is usually carried out in the presence of a solvent.

Examples of the solvent include aliphatic halogenated hydrocarbons such as dichloromethane and chloroform, aromatic hydrocarbons such as toluene and xylene, alcohols such as methanol and ethanol, ethers such as diethyl ether, THF, ethylene glycol dimethyl ether, tert-butyl methyl ether and 1,4-dioxane, water, and mixtures thereof.

In the reaction, hydrazine is usually used in a ratio of 1 to 2 mol, based on 1 mol of the intermediate compound (M22).

The reaction temperature is usually within the range of 0 to 150° C. The reaction time is usually within the range of 0.1 to 24 hours.

After completion of the reaction, the intermediate compound (M23) can be isolated by subjecting it to usual post-treatment operations. The isolated intermediate compound (M23) also can be further purified by chromatography, recrystallization, or the like.

The compound of the present invention (P4) can be produced by reacting the compound (M23) with the compound (M24) or the compound (M25).

The reaction is usually carried out in the presence of a solvent.

Examples of the solvent include aliphatic halogenated hydrocarbons such as dichloromethane and chloroform, alcohols such as methanol and ethanol, nitriles such as acetonitrile and propionitrile, aromatic hydrocarbons such as toluene and xylene, ethers such as diethyl ether, THF, ethylene glycol dimethyl ether, tert-butyl methyl ether and 1,4-dioxane, aprotic polar solvents such as DMF, NMP, DMI and DMSO, acetic acid, water, and mixtures thereof.

The reaction can be also carried out by adding an acid catalyst such as p-toluenesulfonic acid, trifluoroacetic acid or hydrochloric acid, as necessary.

The reaction can be also carried out by adding a base such as sodium methoxide, potassium tert-butoxide or triethylamine, as necessary.

In the reaction, the compound (M24) is usually used in a ratio of 1 to 3 mol, the compound (M25) is usually used in a ratio of 1 to 3 mol, and the base is usually used in a ratio of 1 to 3 mol, based on 1 mol of the intermediate compound (M16).

The reaction temperature is usually within the range of 0 to 150° C. The reaction time is usually within the range of 0.1 to 24 hours.

After completion of the reaction, the compound of the present invention (P4) can be isolated by subjecting it to usual post-treatment operations. The isolated compound of the present invention (P4) also can be further purified by chromatography, recrystallization, or the like.

(Production Method 5)

The compound of the present invention (P6) in which A$^2$ is CR$^{8'}$ (wherein R$^{8'}$ is a chlorine atom, a bromine atom or an iodine atom) in the formula (1) and the compound of the present invention (P7) in which A$^2$ is CR$^8$ in the formula (1) can be produced according to the following scheme:

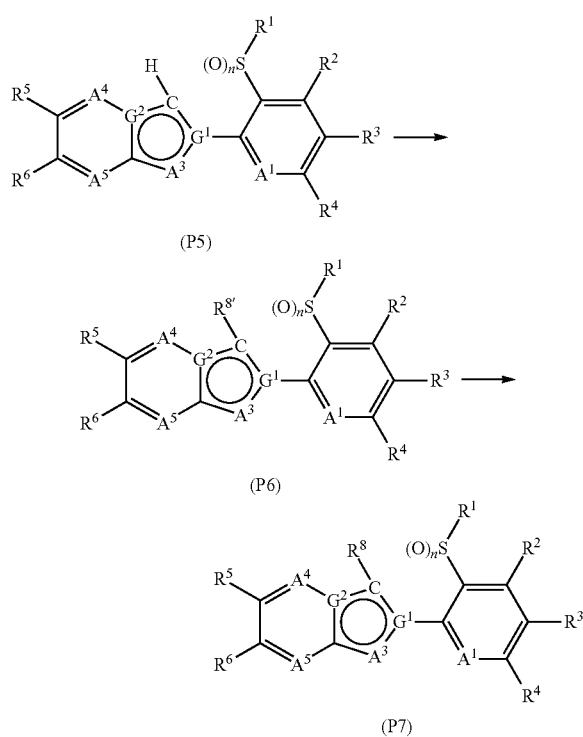

(P5)

(P6)

(P7)

wherein $R^{8'}$ represents a chlorine atom, a bromine atom or an iodine atom, and other symbols represent the same meaning as in the formula (1).

The compound of the present invention (P6) can be produced by reacting the compound of the present invention (P5) with a halogenating agent.

The reaction is usually carried out in the presence of a solvent.

Examples of the solvent include aliphatic halogenated hydrocarbons such as dichloromethane and chloroform, aromatic hydrocarbons such as toluene and xylene, ethers such as diethyl ether, THF, ethylene glycol dimethyl ether, tert-butyl methyl ether and 1,4-dioxane, aprotic polar solvents such as DMF, NMP, DMI and DMSO, and mixtures thereof.

Examples of the halogenating agent include chlorine, bromine, iodine, N-chlorosuccinimide, N-bromosuccinimide, N-iodosuccinimide and halonium salts.

In the reaction, the halogenating agent is usually used in a ratio of 1 to 2 mol, based on 1 mol of the compound of the present invention (P5).

The reaction temperature is usually within the range of 0 to 150° C. The reaction time is usually within the range of 0.1 to 24 hours.

After completion of the reaction, the compound of the present invention (P6) can be isolated by subjecting it to usual post-treatment operations. The isolated compound of the present invention (P6) also can be further purified by chromatography, recrystallization, or the like.

The compound of the present invention (P7) can be produced by reacting the compound of the present invention (P6) with an organic boron compound, an organic zinc compound, an organic silicon compound, an organic tin compound, an alcohol, a thiol, an amine or the like.

The reaction is usually carried out in the presence of a solvent.

Examples of the solvent include aliphatic halogenated hydrocarbons such as dichloromethane and chloroform, aromatic hydrocarbons such as toluene and xylene, ethers such as diethyl ether, THF, ethylene glycol dimethyl ether, tert-butyl methyl ether and 1,4-dioxane, aprotic polar solvents such as DMF, NMP, DMI and DMSO, water, and mixtures thereof.

In the reaction, a catalyst can be added as necessary. Examples of the catalyst include palladium catalysts such as tetrakis(triphenylphosphine)palladium, a [1,1'-bis(diphenylphosphino)ferrocene]dichloropalladium methylene chloride complex, tris(dibenzylideneacetone) dipalladium(0) and palladium acetate and copper catalysts such as copper(I) bromide and copper(I) iodide.

In the reaction, a ligand can be also added as necessary. Examples of the ligand include tricyclohexylphosphine and X-Phos(2-dicyclohexylphosphino-2',4',6'-triisopropylbiphenyl).

In the reaction, a base can be also added as necessary.

Examples of the base include inorganic bases such as sodium hydroxide, potassium hydroxide, potassium carbonate, cesium carbonate, potassium tert-butoxide and potassium phosphate, organic acid salts such as sodium acetate and potassium acetate, and tertiary amines such as triethylamine and N,N-diisopropylethylamine.

In the reaction, the organic boron compound, organic zinc compound, organic silicon compound, organic tin compound, alcohol, thiol, amine or the like is usually used in a ratio of 1 to 3 mol, the catalyst is used in a ratio of 0.0001 to 1 mol, the ligand is used in a ratio of 0.0002 to 1 mol, and the base is usually used in a ratio of 1 to 10 mol, based on 1 mol of the compound of the present invention (P6).

The reaction temperature is usually within the range of 50 to 200° C. The reaction time is usually within the range of 0.1 to 24 hours.

After completion of the reaction, the compound of the present invention (P7) can be isolated by subjecting it to usual post-treatment operations. The isolated compound of the present invention (P7) also can be further purified by recrystallization, chromatography, or the like.

(Production Method 6)

The compound of the present invention (P9) in which $A^3$ is $CR^{9'}$ (wherein $R^{9'}$ is a chlorine atom, a bromine atom or an iodine atom) in the formula (1) and the compound of the present invention (P10) in which $A^3$ is $CR^8$ in the formula (1) can be produced according to the following scheme:

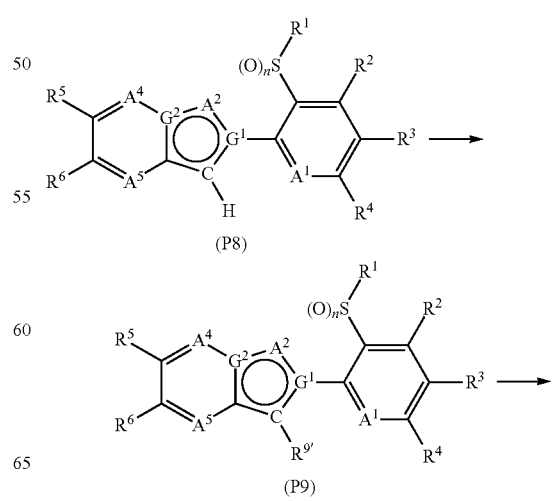

(P8)

(P9)

-continued

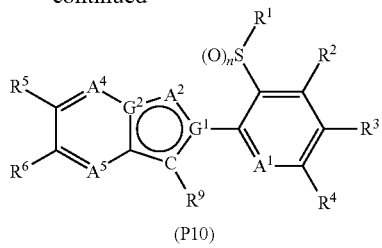

(P10)

wherein R[8'] represents a chlorine atom, a bromine atom or an iodine atom, and other symbols represent the same meaning as in the formula (1).

The compound of the present invention (P9) can be produced according to Production Method 5, using the compound of the present invention (P8) in place of the compound of the present invention (P5).

The compound of the present invention (P10) can be produced according to Production Method 5, using the compound of the present invention (P9) in place of the compound of the present invention (P6).

(Production Method 7)

The compound of the present invention in which n is 1 or 2 in the formula (1) can be produced by oxidizing the compound of the present invention in which n is 0.

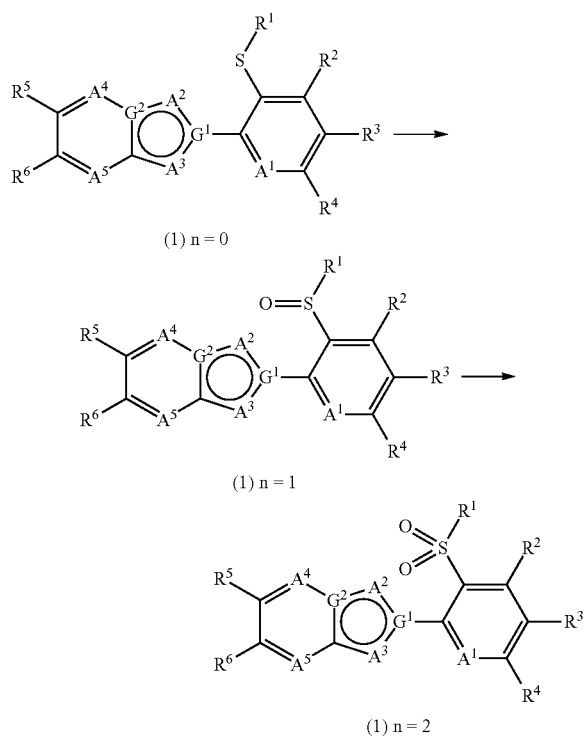

wherein symbols represent the same meaning as in the formula (1).

The compound of the present invention (1-n1) in which n is 1 in the formula (1) can be produced by reacting the compound of the present invention (1-n0) in which n is 0 with an oxidizing agent.

The reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include sodium periodate and m-chloroperoxybenzoic acid.

In the reaction, the oxidizing agent is usually used in a ratio of 1 to 3 mol, based on 1 mol of the compound of the present invention (1-n0). Preferably, the oxidizing agent is used in a ratio of 1 to 1.2 mol, based on 1 mol of the compound of the present invention (1-n0).

The reaction temperature is usually within the range of −20 to 80° C. The reaction time is usually within the range of 0.1 to 12 hours.

After completion of the reaction, the compound of the present invention (1-n1) can be isolated by subjecting it to usual post-treatment operations. The isolated compound of the present invention (1-n1) also can be further purified by chromatography, recrystallization, or the like.

The compound of the present invention (1-n2) in which n is 2 in the formula (1) can be produced by reacting the compound of the present invention (1-n1) in which n is 1 with an oxidizing agent.

The reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperoxybenzoic acid and aqueous hydrogen peroxide.

In the reaction, the oxidizing agent is usually used in a ratio of 1 to 4 mol, based on 1 mol of the compound of the present invention (1-n1). Preferably, the oxidizing agent is used in a ratio of 1 to 2 mol, based on 1 mol of the compound of the present invention (1-n1).

The reaction temperature is usually within the range of −20 to 120° C. The reaction time is usually within the range of 0.1 to 12 hours.

After completion of the reaction, the compound of the present invention (1-n2) can be isolated by subjecting it to usual post-treatment operations. The compound of the present invention (1-n2) also can be further purified by chromatography, recrystallization, or the like.

The compound of the present invention (1-n2) in which n is 2 in the formula (1) can be produced by a one step reaction (one pot) by reacting the compound of the present invention (1-n0) in which n is 0 with an oxidizing agent.

The reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 2 to 5 mol, based on 1 mol of the compound of the present invention (1-n0). Preferably, the oxidizing agent is used in a ratio of 2 to 3 mol, based on 1 mol of the compound of the present invention (1-n0).

The reaction temperature is usually within the range of 0 to 120° C. The reaction time is usually within the range of 0.1 to 12 hours.

After completion of the reaction, the compound of the present invention (1-n2) can be isolated by subjecting it to usual post-treatment operations. The isolated compound of the present invention (1-n2) also can be further purified by chromatography, recrystallization, or the like.

(Production Method 8)

Among the compounds of the present invention and the above-described intermediate compounds, a compound having a nitrogen-containing heterocyclic group having a lone pair of electrons on the nitrogen atom is reacted with an oxidizing agent, whereby an N-oxide in which the nitrogen atom is oxidized can be also produced.

Examples of the nitrogen-containing heterocyclic group include a pyridine ring, and fused rings containing a pyridine ring.

The reaction can be carried out by a known method, and is carried out using an oxidizing agent such as m-chloroperbenzoic acid or hydrogen peroxide, in a solvent, for example, a halogenated hydrocarbon such as dichloromethane, chloroform or chlorobenzene, an alcohol such as methanol or ethanol, acetic acid, water, and mixtures thereof.

Next, specific examples of the compound of the present invention are shown below.

In the formula (A-1),

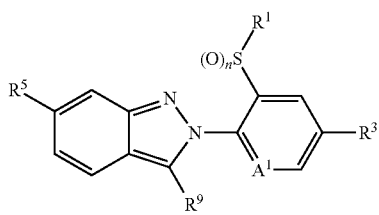

wherein symbols represent the same meaning as in the formula (1), compounds of the present invention wherein $R^5$ is a trifluoromethyl group, $R^9$ is a hydrogen atom, and $R^1$, $R^3$, $A^1$ and n are the combinations shown in [Table 1] to [Table 16].

TABLE 1

| $R^1$ | $R^3$ | $A^1$ | n |
|---|---|---|---|
| Me | H | N | 0 |
| Me | H | N | 1 |
| Me | H | N | 2 |
| Me | F | N | 0 |
| Me | F | N | 1 |
| Me | F | N | 2 |
| Me | Cl | N | 0 |
| Me | Cl | N | 1 |
| Me | Cl | N | 2 |
| Me | Br | N | 0 |
| Me | Br | N | 1 |
| Me | Br | N | 2 |
| Me | $CF_3$ | N | 0 |
| Me | $CF_3$ | N | 1 |
| Me | $CF_3$ | N | 2 |
| Me | $CF_2CF_3$ | N | 0 |
| Me | $CF_2CF_3$ | N | 1 |
| Me | $CF_2CF_3$ | N | 2 |
| Me | $OCF_3$ | N | 0 |
| Me | $OCF_3$ | N | 1 |
| Me | $OCF_3$ | N | 2 |
| Me | $SCF_3$ | N | 0 |
| Me | $SCF_3$ | N | 1 |
| Me | $SCF_3$ | N | 2 |
| Me | $S(O)CF_3$ | N | 0 |
| Me | $S(O)CF_3$ | N | 1 |

TABLE 1-continued

| $R^1$ | $R^3$ | $A^1$ | n |
|---|---|---|---|
| Me | $S(O)CF_3$ | N | 2 |
| Me | $S(O)_2CF_3$ | N | 0 |
| Me | $S(O)_2CF_3$ | N | 1 |
| Me | $S(O)_2CF_3$ | N | 2 |

TABLE 2

| $R^1$ | $R^3$ | $A^1$ | n |
|---|---|---|---|
| Et | H | N | 0 |
| Et | H | N | 1 |
| Et | H | N | 2 |
| Et | F | N | 0 |
| Et | F | N | 1 |
| Et | F | N | 2 |
| Et | Cl | N | 0 |
| Et | Cl | N | 1 |
| Et | Cl | N | 2 |
| Et | Br | N | 0 |
| Et | Br | N | 1 |
| Et | Br | N | 2 |
| Et | $CF_3$ | N | 0 |
| Et | $CF_3$ | N | 1 |
| Et | $CF_3$ | N | 2 |
| Et | $CF_2CF_3$ | N | 0 |
| Et | $CF_2CF_3$ | N | 1 |
| Et | $CF_2CF_3$ | N | 2 |
| Et | $OCF_3$ | N | 0 |
| Et | $OCF_3$ | N | 1 |
| Et | $OCF_3$ | N | 2 |
| Et | $SCF_3$ | N | 0 |
| Et | $SCF_3$ | N | 1 |
| Et | $SCF_3$ | N | 2 |
| Et | $S(O)CF_3$ | N | 0 |
| Et | $S(O)CF_3$ | N | 1 |
| Et | $S(O)CF_3$ | N | 2 |
| Et | $S(O)_2CF_3$ | N | 0 |
| Et | $S(O)_2CF_3$ | N | 1 |
| Et | $S(O)_2CF_3$ | N | 2 |

TABLE 3

| $R^1$ | $R^3$ | $A^1$ | n |
|---|---|---|---|
| Pr | H | N | 0 |
| Pr | H | N | 1 |
| Pr | H | N | 2 |
| Pr | F | N | 0 |
| Pr | F | N | 1 |
| Pr | F | N | 2 |
| Pr | Cl | N | 0 |
| Pr | Cl | N | 1 |
| Pr | Cl | N | 2 |
| Pr | Br | N | 0 |
| Pr | Br | N | 1 |
| Pr | Br | N | 2 |
| Pr | $CF_3$ | N | 0 |
| Pr | $CF_3$ | N | 1 |
| Pr | $CF_3$ | N | 2 |
| Pr | $CF_2CF_3$ | N | 0 |
| Pr | $CF_2CF_3$ | N | 1 |
| Pr | $CF_2CF_3$ | N | 2 |
| Pr | $OCF_3$ | N | 0 |
| Pr | $OCF_3$ | N | 1 |
| Pr | $OCF_3$ | N | 2 |
| Pr | $SCF_3$ | N | 0 |
| Pr | $SCF_3$ | N | 1 |
| Pr | $SCF_3$ | N | 2 |
| Pr | $S(O)CF_3$ | N | 0 |
| Pr | $S(O)CF_3$ | N | 1 |

TABLE 3-continued

| R¹ | R³ | A¹ | n |
|---|---|---|---|
| Pr | S(O)CF₃ | N | 2 |
| Pr | S(O)₂CF₃ | N | 0 |
| Pr | S(O)₂CF₃ | N | 1 |
| Pr | S(O)₂CF₃ | N | 2 |

TABLE 4

| R¹ | R³ | A¹ | n |
|---|---|---|---|
| iPr | H | N | 0 |
| iPr | H | N | 1 |
| iPr | H | N | 2 |
| iPr | F | N | 0 |
| iPr | F | N | 1 |
| iPr | F | N | 2 |
| iPr | Cl | N | 0 |
| iPr | Cl | N | 1 |
| iPr | Cl | N | 2 |
| iPr | Br | N | 0 |
| iPr | Br | N | 1 |
| iPr | Br | N | 2 |
| iPr | CF₃ | N | 0 |
| iPr | CF₃ | N | 1 |
| iPr | CF₃ | N | 2 |
| iPr | CF₂CF₃ | N | 0 |
| iPr | CF₂CF₃ | N | 1 |
| iPr | CF₂CF₃ | N | 2 |
| iPr | OCF₃ | N | 0 |
| iPr | OCF₃ | N | 1 |
| iPr | OCF₃ | N | 2 |
| iPr | SCF₃ | N | 0 |
| iPr | SCF₃ | N | 1 |
| iPr | SCF₃ | N | 2 |
| iPr | S(O)CF₃ | N | 0 |
| iPr | S(O)CF₃ | N | 1 |
| iPr | S(O)CF₃ | N | 2 |
| iPr | S(O)₂CF₃ | N | 0 |
| iPr | S(O)₂CF₃ | N | 1 |
| iPr | S(O)₂CF₃ | N | 2 |

TABLE 5

| R¹ | R³ | A¹ | n |
|---|---|---|---|
| cyPr | H | N | 0 |
| cyPr | H | N | 1 |
| cyPr | H | N | 2 |
| cyPr | F | N | 0 |
| cyPr | F | N | 1 |
| cyPr | F | N | 2 |
| cyPr | Cl | N | 0 |
| cyPr | Cl | N | 1 |
| cyPr | Cl | N | 2 |
| cyPr | Br | N | 0 |
| cyPr | Br | N | 1 |
| cyPr | Br | N | 2 |
| cyPr | CF₃ | N | 0 |
| cyPr | CF₃ | N | 1 |
| cyPr | CF₃ | N | 2 |
| cyPr | CF₂CF₃ | N | 0 |
| cyPr | CF₂CF₃ | N | 1 |
| cyPr | CF₂CF₃ | N | 2 |
| cyPr | OCF₃ | N | 0 |
| cyPr | OCF₃ | N | 1 |
| cyPr | OCF₃ | N | 2 |
| cyPr | SCF₃ | N | 0 |
| cyPr | SCF₃ | N | 1 |
| cyPr | SCF₃ | N | 2 |
| cyPr | S(O)CF₃ | N | 0 |

TABLE 5-continued

| R¹ | R³ | A¹ | n |
|---|---|---|---|
| cyPr | S(O)CF₃ | N | 1 |
| cyPr | S(O)CF₃ | N | 2 |
| cyPr | S(O)₂CF₃ | N | 0 |
| cyPr | S(O)₂CF₃ | N | 1 |
| cyPr | S(O)₂CF₃ | N | 2 |

TABLE 6

| R¹ | R³ | A¹ | n |
|---|---|---|---|
| CH₂cyP | H | N | 0 |
| CH₂cyP | H | N | 1 |
| CH₂cyP | H | N | 2 |
| CH₂cyP | F | N | 0 |
| CH₂cyP | F | N | 1 |
| CH₂cyP | F | N | 2 |
| CH₂cyP | Cl | N | 0 |
| CH₂cyP | Cl | N | 1 |
| CH₂cyP | Cl | N | 2 |
| CH₂cyP | Br | N | 0 |
| CH₂cyP | Br | N | 1 |
| CH₂cyP | Br | N | 2 |
| CH₂cyP | CF₃ | N | 0 |
| CH₂cyP | CF₃ | N | 1 |
| CH₂cyP | CF₃ | N | 2 |
| CH₂cyP | CF₂CF₃ | N | 0 |
| CH₂cyP | CF₂CF₃ | N | 1 |
| CH₂cyP | CF₂CF₃ | N | 2 |
| CH₂cyP | OCF₃ | N | 0 |
| CH₂cyP | OCF₃ | N | 1 |
| CH₂cyP | OCF₃ | N | 2 |
| CH₂cyP | SCF₃ | N | 0 |
| CH₂cyP | SCF₃ | N | 1 |
| CH₂cyP | SCF₃ | N | 2 |
| CH₂cyP | S(O)CF₃ | N | 0 |
| CH₂cyP | S(O)CF₃ | N | 1 |
| CH₂cyP | S(O)CF₃ | N | 2 |
| CH₂cyP | S(O)₂CF₃ | N | 0 |
| CH₂cyP | S(O)₂CF₃ | N | 1 |
| CH₂cyP | S(O)₂CF₃ | N | 2 |

TABLE 7

| R¹ | R³ | A¹ | n |
|---|---|---|---|
| CF₃ | H | N | 0 |
| CF₃ | H | N | 1 |
| CF₃ | H | N | 2 |
| CF₃ | F | N | 0 |
| CF₃ | F | N | 1 |
| CF₃ | F | N | 2 |
| CF₃ | Cl | N | 0 |
| CF₃ | Cl | N | 1 |
| CF₃ | Cl | N | 2 |
| CF₃ | Br | N | 0 |
| CF₃ | Br | N | 1 |
| CF₃ | Br | N | 2 |
| CF₃ | CF₃ | N | 0 |
| CF₃ | CF₃ | N | 1 |
| CF₃ | CF₃ | N | 2 |
| CF₃ | CF₂CF₃ | N | 0 |
| CF₃ | CF₂CF₃ | N | 1 |
| CF₃ | CF₂CF₃ | N | 2 |
| CF₃ | OCF₃ | N | 0 |
| CF₃ | OCF₃ | N | 1 |
| CF₃ | OCF₃ | N | 2 |
| CF₃ | SCF₃ | N | 0 |
| CF₃ | SCF₃ | N | 1 |
| CF₃ | SCF₃ | N | 2 |
| CF₃ | S(O)CF₃ | N | 0 |
| CF₃ | S(O)CF₃ | N | 1 |
| CF₃ | S(O)CF₃ | N | 2 |
| CF₃ | S(O)₂CF₃ | N | 0 |

TABLE 7-continued

| R¹ | R³ | A¹ | n |
|---|---|---|---|
| CF₃ | S(O)₂CF₃ | N | 1 |
| CF₃ | S(O)₂CF₃ | N | 2 |

TABLE 8

| R¹ | R³ | A¹ | n |
|---|---|---|---|
| CH₂CF₃ | H | N | 0 |
| CH₂CF₃ | H | N | 1 |
| CH₂CF₃ | H | N | 2 |
| CH₂CF₃ | F | N | 0 |
| CH₂CF₃ | F | N | 1 |
| CH₂CF₃ | F | N | 2 |
| CH₂CF₃ | Cl | N | 0 |
| CH₂CF₃ | Cl | N | 1 |
| CH₂CF₃ | Cl | N | 2 |
| CH₂CF₃ | Br | N | 0 |
| CH₂CF₃ | Br | N | 1 |
| CH₂CF₃ | Br | N | 2 |
| CH₂CF₃ | CF₃ | N | 0 |
| CH₂CF₃ | CF₃ | N | 1 |
| CH₂CF₃ | CF₃ | N | 2 |
| CH₂CF₃ | CF₂CF₃ | N | 0 |
| CH₂CF₃ | CF₂CF₃ | N | 1 |
| CH₂CF₃ | CF₂CF₃ | N | 2 |
| CH₂CF₃ | OCF₃ | N | 0 |
| CH₂CF₃ | OCF₃ | N | 1 |
| CH₂CF₃ | OCF₃ | N | 2 |
| CH₂CF₃ | SCF₃ | N | 0 |
| CH₂CF₃ | SCF₃ | N | 1 |
| CH₂CF₃ | SCF₃ | N | 2 |
| CH₂CF₃ | S(O)CF₃ | N | 0 |
| CH₂CF₃ | S(O)CF₃ | N | 1 |
| CH₂CF₃ | S(O)CF₃ | N | 2 |
| CH₂CF₃ | S(O)₂CF₃ | N | 0 |
| CH₂CF₃ | S(O)₂CF₃ | N | 1 |
| CH₂CF₃ | S(O)₂CF₃ | N | 2 |

TABLE 9

| R¹ | R³ | A¹ | n |
|---|---|---|---|
| Me | H | CH | 0 |
| Me | H | CH | 1 |
| Me | H | CH | 2 |
| Me | F | CH | 0 |
| Me | F | CH | 1 |
| Me | F | CH | 2 |
| Me | Cl | CH | 0 |
| Me | Cl | CH | 1 |
| Me | Cl | CH | 2 |
| Me | Br | CH | 0 |
| Me | Br | CH | 1 |
| Me | Br | CH | 2 |
| Me | CF₃ | CH | 0 |
| Me | CF₃ | CH | 1 |
| Me | CF₃ | CH | 2 |
| Me | CF₂CF₃ | CH | 0 |
| Me | CF₂CF₃ | CH | 1 |
| Me | CF₂CF₃ | CH | 2 |
| Me | OCF₃ | CH | 0 |
| Me | OCF₃ | CH | 1 |
| Me | OCF₃ | CH | 2 |
| Me | SCF₃ | CH | 0 |
| Me | SCF₃ | CH | 1 |
| Me | SCF₃ | CH | 2 |
| Me | S(O)CF₃ | CH | 0 |
| Me | S(O)CF₃ | CH | 1 |
| Me | S(O)CF₃ | CH | 2 |
| Me | S(O)₂CF₃ | CH | 0 |
| Me | S(O)₂CF₃ | CH | 1 |
| Me | S(O)₂CF₃ | CH | 2 |

TABLE 10

| R¹ | R³ | A¹ | n |
|---|---|---|---|
| Et | H | CH | 0 |
| Et | H | CH | 1 |
| Et | H | CH | 2 |
| Et | F | CH | 0 |
| Et | F | CH | 1 |
| Et | F | CH | 2 |
| Et | Cl | CH | 0 |
| Et | Cl | CH | 1 |
| Et | Cl | CH | 2 |
| Et | Br | CH | 0 |
| Et | Br | CH | 1 |
| Et | Br | CH | 2 |
| Et | CF₃ | CH | 0 |
| Et | CF₃ | CH | 1 |
| Et | CF₃ | CH | 2 |
| Et | CF₂CF₃ | CH | 0 |
| Et | CF₂CF₃ | CH | 1 |
| Et | CF₂CF₃ | CH | 2 |
| Et | OCF₃ | CH | 0 |
| Et | OCF₃ | CH | 1 |
| Et | OCF₃ | CH | 2 |
| Et | SCF₃ | CH | 0 |
| Et | SCF₃ | CH | 1 |
| Et | SCF₃ | CH | 2 |
| Et | S(O)CF₃ | CH | 0 |
| Et | S(O)CF₃ | CH | 1 |
| Et | S(O)CF₃ | CH | 2 |
| Et | S(O)₂CF₃ | CH | 0 |
| Et | S(O)₂CF₃ | CH | 1 |
| Et | S(O)₂CF₃ | CH | 2 |

TABLE 11

| R¹ | R³ | A¹ | n |
|---|---|---|---|
| Pr | H | CH | 0 |
| Pr | H | CH | 1 |
| Pr | H | CH | 2 |
| Pr | F | CH | 0 |
| Pr | F | CH | 1 |
| Pr | F | CH | 2 |
| Pr | Cl | CH | 0 |
| Pr | Cl | CH | 1 |
| Pr | Cl | CH | 2 |
| Pr | Br | CH | 0 |
| Pr | Br | CH | 1 |
| Pr | Br | CH | 2 |
| Pr | CF₃ | CH | 0 |
| Pr | CF₃ | CH | 1 |
| Pr | CF₃ | CH | 2 |
| Pr | CF₂CF₃ | CH | 0 |
| Pr | CF₂CF₃ | CH | 1 |
| Pr | CF₂CF₃ | CH | 2 |
| Pr | OCF₃ | CH | 0 |
| Pr | OCF₃ | CH | 1 |
| Pr | OCF₃ | CH | 2 |
| Pr | SCF₃ | CH | 0 |
| Pr | SCF₃ | CH | 1 |
| Pr | SCF₃ | CH | 2 |
| Pr | S(O)CF₃ | CH | 0 |
| Pr | S(O)CF₃ | CH | 1 |
| Pr | S(O)CF₃ | CH | 2 |
| Pr | S(O)₂CF₃ | CH | 0 |
| Pr | S(O)₂CF₃ | CH | 1 |
| Pr | S(O)₂CF₃ | CH | 2 |

TABLE 12

| R¹ | R³ | A¹ | n |
|---|---|---|---|
| iPr | H | CH | 0 |
| iPr | H | CH | 1 |
| iPr | H | CH | 2 |

TABLE 12-continued

| R$^1$ | R$^3$ | A$^1$ | n |
|---|---|---|---|
| iPr | F | CH | 0 |
| iPr | F | CH | 1 |
| iPr | F | CH | 2 |
| iPr | Cl | CH | 0 |
| iPr | Cl | CH | 1 |
| iPr | Cl | CH | 2 |
| iPr | Br | CH | 0 |
| iPr | Br | CH | 1 |
| iPr | Br | CH | 2 |
| iPr | CF$_3$ | CH | 0 |
| iPr | CF$_3$ | CH | 1 |
| iPr | CF$_3$ | CH | 2 |
| iPr | CF$_2$CF$_3$ | CH | 0 |
| iPr | CF$_2$CF$_3$ | CH | 1 |
| iPr | CF$_2$CF$_3$ | CH | 2 |
| iPr | OCF$_3$ | CH | 0 |
| iPr | OCF$_3$ | CH | 1 |
| iPr | OCF$_3$ | CH | 2 |
| iPr | SCF$_3$ | CH | 0 |
| iPr | SCF$_3$ | CH | 1 |
| iPr | SCF$_3$ | CH | 2 |
| iPr | S(O)CF$_3$ | CH | 0 |
| iPr | S(O)CF$_3$ | CH | 1 |
| iPr | S(O)CF$_3$ | CH | 2 |
| iPr | S(O)$_2$CF$_3$ | CH | 0 |
| iPr | S(O)$_2$CF$_3$ | CH | 1 |
| iPr | S(O)$_2$CF$_3$ | CH | 2 |

TABLE 13

| R$^1$ | R$^3$ | A$^1$ | n |
|---|---|---|---|
| cyPr | H | CH | 0 |
| cyPr | H | CH | 1 |
| cyPr | H | CH | 2 |
| cyPr | F | CH | 0 |
| cyPr | F | CH | 1 |
| cyPr | F | CH | 2 |
| cyPr | Cl | CH | 0 |
| cyPr | Cl | CH | 1 |
| cyPr | Cl | CH | 2 |
| cyPr | Br | CH | 0 |
| cyPr | Br | CH | 1 |
| cyPr | Br | CH | 2 |
| cyPr | CF$_3$ | CH | 0 |
| cyPr | CF$_3$ | CH | 1 |
| cyPr | CF$_3$ | CH | 2 |
| cyPr | CF$_2$CF$_3$ | CH | 0 |
| cyPr | CF$_2$CF$_3$ | CH | 1 |
| cyPr | CF$_2$CF$_3$ | CH | 2 |
| cyPr | OCF$_3$ | CH | 0 |
| cyPr | OCF$_3$ | CH | 1 |
| cyPr | OCF$_3$ | CH | 2 |
| cyPr | SCF$_3$ | CH | 0 |
| cyPr | SCF$_3$ | CH | 1 |
| cyPr | SCF$_3$ | CH | 2 |
| cyPr | S(O)CF$_3$ | CH | 0 |
| cyPr | S(O)CF$_3$ | CH | 1 |
| cyPr | S(O)CF$_3$ | CH | 2 |
| cyPr | S(O)$_2$CF$_3$ | CH | 0 |
| cyPr | S(O)$_2$CF$_3$ | CH | 1 |
| cyPr | S(O)$_2$CF$_3$ | CH | 2 |

TABLE 14

| R$^1$ | R$^3$ | A$^1$ | n |
|---|---|---|---|
| CH$_2$cyP | H | CH | 0 |
| CH$_2$cyP | H | CH | 1 |
| CH$_2$cyP | H | CH | 2 |
| CH$_2$cyP | F | CH | 0 |
| CH$_2$cyP | F | CH | 1 |
| CH$_2$cyP | F | CH | 2 |

TABLE 14-continued

| R$^1$ | R$^3$ | A$^1$ | n |
|---|---|---|---|
| CH$_2$cyP | Cl | CH | 0 |
| CH$_2$cyP | Cl | CH | 1 |
| CH$_2$cyP | Cl | CH | 2 |
| CH$_2$cyP | Br | CH | 0 |
| CH$_2$cyP | Br | CH | 1 |
| CH$_2$cyP | Br | CH | 2 |
| CH$_2$cyP | CF$_3$ | CH | 0 |
| CH$_2$cyP | CF$_3$ | CH | 1 |
| CH$_2$cyP | CF$_3$ | CH | 2 |
| CH$_2$cyP | CF$_2$CF$_3$ | CH | 0 |
| CH$_2$cyP | CF$_2$CF$_3$ | CH | 1 |
| CH$_2$cyP | CF$_2$CF$_3$ | CH | 2 |
| CH$_2$cyP | OCF$_3$ | CH | 0 |
| CH$_2$cyP | OCF$_3$ | CH | 1 |
| CH$_2$cyP | OCF$_3$ | CH | 2 |
| CH$_2$cyP | SCF$_3$ | CH | 0 |
| CH$_2$cyP | SCF$_3$ | CH | 1 |
| CH$_2$cyP | SCF$_3$ | CH | 2 |
| CH$_2$cyP | S(O)CF$_3$ | CH | 0 |
| CH$_2$cyP | S(O)CF$_3$ | CH | 1 |
| CH$_2$cyP | S(O)CF$_3$ | CH | 2 |
| CH$_2$cyP | S(O)$_2$CF$_3$ | CH | 0 |
| CH$_2$cyP | S(O)$_2$CF$_3$ | CH | 1 |
| CH$_2$cyP | S(O)$_2$CF$_3$ | CH | 2 |

TABLE 15

| R$^1$ | R$^3$ | A$^1$ | n |
|---|---|---|---|
| CF$_3$ | H | CH | 0 |
| CF$_3$ | H | CH | 1 |
| CF$_3$ | H | CH | 2 |
| CF$_3$ | F | CH | 0 |
| CF$_3$ | F | CH | 1 |
| CF$_3$ | F | CH | 2 |
| CF$_3$ | Cl | CH | 0 |
| CF$_3$ | Cl | CH | 1 |
| CF$_3$ | Cl | CH | 2 |
| CF$_3$ | Br | CH | 0 |
| CF$_3$ | Br | CH | 1 |
| CF$_3$ | Br | CH | 2 |
| CF$_3$ | CF$_3$ | CH | 0 |
| CF$_3$ | CF$_3$ | CH | 1 |
| CF$_3$ | CF$_3$ | CH | 2 |
| CF$_3$ | CF$_2$CF$_3$ | CH | 0 |
| CF$_3$ | CF$_2$CF$_3$ | CH | 1 |
| CF$_3$ | CF$_2$CF$_3$ | CH | 2 |
| CF$_3$ | OCF$_3$ | CH | 0 |
| CF$_3$ | OCF$_3$ | CH | 1 |
| CF$_3$ | OCF$_3$ | CH | 2 |
| CF$_3$ | SCF$_3$ | CH | 0 |
| CF$_3$ | SCF$_3$ | CH | 1 |
| CF$_3$ | SCF$_3$ | CH | 2 |
| CF$_3$ | S(O)CF$_3$ | CH | 0 |
| CF$_3$ | S(O)CF$_3$ | CH | 1 |
| CF$_3$ | S(O)CF$_3$ | CH | 2 |
| CF$_3$ | S(O)$_2$CF$_3$ | CH | 0 |
| CF$_3$ | S(O)$_2$CF$_3$ | CH | 1 |
| CF$_3$ | S(O)$_2$CF$_3$ | CH | 2 |

TABLE 16

| R$^1$ | R$^3$ | A$^1$ | n |
|---|---|---|---|
| CH$_2$CF$_3$ | H | CH | 0 |
| CH$_2$CF$_3$ | H | CH | 1 |
| CH$_2$CF$_3$ | H | CH | 2 |
| CH$_2$CF$_3$ | F | CH | 0 |
| CH$_2$CF$_3$ | F | CH | 1 |
| CH$_2$CF$_3$ | F | CH | 2 |
| CH$_2$CF$_3$ | Cl | CH | 0 |
| CH$_2$CF$_3$ | Cl | CH | 1 |
| CH$_2$CF$_3$ | Cl | CH | 2 |

TABLE 16-continued

| $R^1$ | $R^3$ | $A^1$ | n |
|---|---|---|---|
| $CH_2CF_3$ | Br | CH | 0 |
| $CH_2CF_3$ | Br | CH | 1 |
| $CH_2CF_3$ | Br | CH | 2 |
| $CH_2CF_3$ | $CF_3$ | CH | 0 |
| $CH_2CF_3$ | $CF_3$ | CH | 1 |
| $CH_2CF_3$ | $CF_3$ | CH | 2 |
| $CH_2CF_3$ | $CF_2CF_3$ | CH | 0 |
| $CH_2CF_3$ | $CF_2CF_3$ | CH | 1 |
| $CH_2CF_3$ | $CF_2CF_3$ | CH | 2 |
| $CH_2CF_3$ | $OCF_3$ | CH | 0 |
| $CH_2CF_3$ | $OCF_3$ | CH | 1 |
| $CH_2CF_3$ | $OCF_3$ | CH | 2 |
| $CH_2CF_3$ | $SCF_3$ | CH | 0 |
| $CH_2CF_3$ | $SCF_3$ | CH | 1 |
| $CH_2CF_3$ | $SCF_3$ | CH | 2 |
| $CH_2CF_3$ | $S(O)CF_3$ | CH | 0 |
| $CH_2CF_3$ | $S(O)CF_3$ | CH | 1 |
| $CH_2CF_3$ | $S(O)CF_3$ | CH | 2 |
| $CH_2CF_3$ | $S(O)_2CF_3$ | CH | 0 |
| $CH_2CF_3$ | $S(O)_2CF_3$ | CH | 1 |
| $CH_2CF_3$ | $S(O)_2CF_3$ | CH | 2 |

(In [Table 1] to [Table 16] above, Me represents a methyl group, Et represents an ethyl group, Pr represents an n-propyl group, iPr represents an isopropyl group, and cyPr represents a cyclopropyl group.)

In the formula (A), compounds wherein $R^5$ is a trifluoromethyl group, $R^9$ is a chlorine atom, and $R^1$, $R^3$, $A^1$ and n are the combinations shown in [Table 1] to [Table 16].

In the formula (A), compounds wherein $R^5$ is a trifluoromethyl group, $R^9$ is a bromine atom, and $R^1$, $R^3$, $A^1$ and n are the combinations shown in [Table 1] to [Table 16].

In the formula (A), compounds wherein $R^5$ is a trifluoromethyl group, $R^9$ is a methyl group, and $R^1$, $R^3$, $A^1$ and n are the combinations shown in [Table 1] to [Table 16].

In the formula (A), compounds wherein $R^5$ is a pentafluoroethyl group, $R^9$ is a hydrogen atom, and $R^1$, $R^3$, $A^1$ and n are the combinations shown in [Table 1] to [Table 16].

In the formula (A), compounds wherein $R^5$ is a pentafluoroethyl group, $R^9$ is a chlorine atom, and $R^1$, $R^3$, $A^1$ and n are the combinations shown in [Table 1] to [Table 16].

In the formula (A), compounds wherein $R^5$ is a pentafluoroethyl group, $R^9$ is a bromine atom, and $R^1$, $R^3$, $A^1$ and n are the combinations shown in [Table 1] to [Table 16].

In the formula (A), compounds wherein $R^5$ is a pentafluoroethyl group, is a methyl group, and R, $R^3$, $A^1$ and n are the combinations shown in [Table 1] to [Table 16].

In the formula (A), compounds wherein $R^5$ is a heptafluoroisopropyl group, $R^9$ is a hydrogen atom, and $R^1$, $R^3$, $A^1$ and n are the combinations shown in [Table 1] to [Table 16].

In the formula (A), compounds wherein $R^5$ is a heptafluoroisopropyl group, $R^9$ is a chlorine atom, and $R^1$, $R^3$, $A^1$ and n are the combinations shown in [Table 1] to [Table 16].

In the formula (A), compounds wherein $R^5$ is a heptafluoroisopropyl group, $R^9$ is a bromine atom, and $R^1$, $R^3$, $A^1$ and n are the combinations shown in [Table 1] to [Table 16].

In the formula (A), compounds wherein $R^5$ is a heptafluoroisopropyl group, $R^9$ is a methyl group, and $R^1$, $R^3$, $A^1$ and n are the combinations shown in [Table 1] to [Table 16].

In the formula (A), compounds wherein $R^5$ is a trifluoromethoxy group, $R^9$ is a hydrogen atom, and $R^1$, $R^3$, $A^1$ and n are the combinations shown in [Table 1] to [Table 16].

In the formula (A), compounds wherein $R^5$ is a trifluoromethoxy group, $R^9$ is a chlorine atom, and $R^1$, $R^3$, $A^1$ and n are the combinations shown in [Table 1] to [Table 16].

In the formula (A), compounds wherein $R^5$ is a trifluoromethoxy group, $R^9$ is a bromine atom, and $R^1$, $R^3$, $A^1$ and n are the combinations shown in [Table 1] to [Table 16].

In the formula (A), compounds wherein $R^5$ is a trifluoromethoxy group, $R^9$ is a methyl group, and $R^1$, $R^3$, $A^1$ and n are the combinations shown in [Table 1] to [Table 16].

In the formula (A), compounds wherein $R^5$ is a trifluoromethylsulfanyl group, $R^9$ is a hydrogen atom, and $R^1$, $R^3$, $A^1$ and n are the combinations shown in [Table 1] to [Table 16].

In the formula (A), compounds wherein $R^5$ is a trifluoromethylsulfanyl group, $R^9$ is a chlorine atom, and $R^1$, $R^3$, $A^1$ and n are the combinations shown in [Table 1] to [Table 16].

In the formula (A), compounds wherein $R^5$ is a trifluoromethylsulfanyl group, $R^9$ is a bromine atom, and $R^1$, $R^3$, $A^1$ and n are the combinations shown in [Table 1] to [Table 16].

In the formula (A), compounds wherein $R^5$ is a trifluoromethylsulfanyl group, $R^9$ is a methyl group, and $R^1$, $R^3$, $A^1$ and n are the combinations shown in [Table 1] to [Table 16].

In the formula (A), compounds wherein $R^5$ is a trifluoromethylsulfinyl group, $R^9$ is a hydrogen atom, and $R^1$, $R^3$, $A^1$ and n are the combinations shown in [Table 1] to [Table 16].

In the formula (A), compounds wherein $R^5$ is a trifluoromethylsulfinyl group, $R^9$ is a chlorine atom, and $R^1$, $R^3$, $A^1$ and n are the combinations shown in [Table 1] to [Table 16].

In the formula (A), compounds wherein $R^5$ is a trifluoromethylsulfinyl group, $R^9$ is a bromine atom, and $R^1$, $R^3$, $A^1$ and n are the combinations shown in [Table 1] to [Table 16].

In the formula (A), compounds wherein $R^5$ is a trifluoromethylsulfinyl group, $R^9$ is a methyl group, and $R^1$, $R^3$, $A^1$ and n are the combinations shown in [Table 1] to [Table 16].

In the formula (A), compounds wherein $R^5$ is a trifluoromethylsulfonyl group, $R^9$ is a hydrogen atom, and $R^1$, $R^3$, $A^1$ and n are the combinations shown in [Table 1] to [Table 16].

In the formula (A), compounds wherein $R^5$ is a trifluoromethylsulfonyl group, $R^9$ is a chlorine atom, and $R^1$, RB, $A^1$ and n are the combinations shown in [Table 1] to [Table 16].

In the formula (A), compounds wherein $R^5$ is a trifluoromethylsulfonyl group, $R^9$ is a bromine atom, and $R^1$, $R^3$, $A^1$ and n are the combinations shown in [Table 1] to [Table 16].

In the formula (A), compounds wherein $R^5$ is a trifluoromethylsulfonyl group, $R^9$ is a methyl group, and $R^1$, $R^3$, $A^1$ and n are the combinations shown in [Table 1] to [Table 16].

In the formula (B), (B)

wherein symbols represent the same meaning as in the formula (1), compounds wherein $R^5$ is a trifluoromethyl group, $R^9$ is a hydrogen atom, and $R^1$, $R^3$, $A^1$ and n are the combinations shown in [Table 1] to [Table 16].

In the formula (B), compounds wherein $R^5$ is a trifluoromethyl group, $R^9$ is a chlorine atom, and $R^1$, $R^3$, $A^1$ and n are the combinations shown in [Table 1] to [Table 16].

In the formula (B), compounds wherein $R^5$ is a trifluoromethyl group, $R^9$ is a bromine atom, and $R^1$, $R^3$, $A^1$ and n are the combinations shown in [Table 1] to [Table 16].

In the formula (B), compounds wherein $R^5$ is a trifluoromethyl group, $R^9$ is a methyl group, and $R^1$, $R^3$, $A^1$ and n are the combinations shown in [Table 1] to [Table 16].

In the formula (B), compounds wherein $R^5$ is a pentafluoroethyl group, $R^9$ is a hydrogen atom, and $R^1$, $R^3$, $A^1$ and n are the combinations shown in [Table 1] to [Table 16].

In the formula (B), compounds wherein $R^5$ is a pentafluoroethyl group, $R^9$ is a chlorine atom, and $R^1$, $R^3$, $A^1$ and n are the combinations shown in [Table 1] to [Table 16].

In the formula (B), compounds wherein $R^5$ is a pentafluoroethyl group, $R^9$ is a bromine atom, and $R^1$, $R^3$, $A^1$ and n are the combinations shown in [Table 1] to [Table 16].

In the formula (B), compounds wherein $R^5$ is a pentafluoroethyl group, $R^9$ is a methyl group, and $R^1$, $R^3$, $A^1$ and n are the combinations shown in [Table 1] to [Table 16].

In the formula (B), compounds wherein $R^5$ is a heptafluoroisopropyl group, $R^9$ is a hydrogen atom, and $R^1$, $R^3$, $A^1$ and n are the combinations shown in [Table 1] to [Table 16].

In the formula (B), compounds wherein $R^5$ is a heptafluoroisopropyl group, $R^9$ is a chlorine atom, and $R^1$, $R^3$, $A^1$ and n are the combinations shown in [Table 1] to [Table 16].

In the formula (B), compounds wherein $R^5$ is a heptafluoroisopropyl group, $R^9$ is a bromine atom, and $R^1$, $R^3$, $A^1$ and n are the combinations shown in [Table 1] to [Table 16].

In the formula (B), compounds wherein $R^5$ is a heptafluoroisopropyl group, $R^9$ is a methyl group, and $R^1$, $R^3$, $A^1$ and n are the combinations shown in [Table 1] to [Table 16].

In the formula (B), compounds wherein $R^5$ is a trifluoromethoxy group, $R^9$ is a hydrogen atom, and $R^1$, $R^3$, $A^1$ and n are the combinations shown in [Table 1] to [Table 16].

In the formula (B), compounds wherein $R^5$ is a trifluoromethoxy group, $R^9$ is a chlorine atom, and $R^1$, $R^3$, $A^1$ and n are the combinations shown in [Table 1] to [Table 16].

In the formula (B), compounds wherein $R^5$ is a trifluoromethoxy group, $R^9$ is a bromine atom, and $R^1$, $R^3$, $A^1$ and n are the combinations shown in [Table 1] to [Table 16].

In the formula (B), compounds wherein $R^5$ is a trifluoromethoxy group, $R^9$ is a methyl group, and $R^1$, $R^3$, $A^1$ and n are the combinations shown in [Table 1] to [Table 16].

In the formula (B), compounds wherein $R^5$ is a trifluoromethylsulfanyl group, $R^9$ is a hydrogen atom, and $R^1$, $R^3$, $A^1$ and n are the combinations shown in [Table 1] to [Table 16].

In the formula (B), compounds wherein $R^5$ is a trifluoromethylsulfanyl group, $R^9$ is a chlorine atom, and $R^1$, $R^3$, $A^1$ and n are the combinations shown in [Table 1] to [Table 16].

In the formula (B), compounds wherein $R^5$ is a trifluoromethylsulfanyl group, $R^9$ is a bromine atom, and $R^1$, $R^3$, $A^1$ and n are the combinations shown in [Table 1] to [Table 16].

In the formula (B), compounds wherein $R^5$ is a trifluoromethylsulfanyl group, $R^9$ is a methyl group, and $R^1$, $R^3$, $A^1$ and n are the combinations shown in [Table 1] to [Table 16].

In the formula (B), compounds wherein $R^5$ is a trifluoromethylsulfinyl group, $R^9$ is a hydrogen atom, and $R^1$, $R^3$, $A^1$ and n are the combinations shown in [Table 1] to [Table 16].

In the formula (B), compounds wherein $R^5$ is a trifluoromethylsulfinyl group, $R^9$ is a chlorine atom, and $R^1$, $R^3$, $A^1$ and n are the combinations shown in [Table 1] to [Table 16].

In the formula (B), compounds wherein $R^5$ is a trifluoromethylsulfinyl group, $R^9$ is a bromine atom, and $R^1$, $R^3$, $A^1$ and n are the combinations shown in [Table 1] to [Table 16].

In the formula (B), compounds wherein $R^5$ is a trifluoromethylsulfinyl group, $R^9$ is a methyl group, and $R^1$, $R^3$, $A^1$ and n are the combinations shown in [Table 1] to [Table 16].

In the formula (B), compounds wherein $R^5$ is a trifluoromethylsulfonyl group, $R^9$ is a hydrogen atom, and $R^1$, $R^3$, $A^1$ and n are the combinations shown in [Table 1] to [Table 16].

In the formula (B), compounds wherein $R^5$ is a trifluoromethylsulfonyl group, $R^9$ is a chlorine atom, and $R^1$, $R^3$, $A^1$ and n are the combinations shown in [Table 1] to [Table 16].

In the formula (B), compounds wherein $R^5$ is a trifluoromethylsulfonyl group, $R^9$ is a bromine atom, and $R^1$, $R^3$, $A^1$ and n are the combinations shown in [Table 1] to [Table 16].

In the formula (B), compounds wherein $R^5$ is a trifluoromethylsulfonyl group, $R^9$ is a methyl group, and $R^1$, $R^3$, $A^1$ and n are the combinations shown in [Table 1] to [Table 16].

In the formula (C-1), (C-1)

wherein symbols represent the same meaning as in the formula (1), compounds wherein $R^5$ is a trifluoromethyl group, $R^8$ is a hydrogen atom, and $R^1$, $R^3$, $A^1$ and n are the combinations shown in [Table 1] to [Table 16].

In the formula (C-1), compounds wherein $R^5$ is a trifluoromethyl group, $R^8$ is a chlorine atom, and $R^1$, $R^3$, $A^1$ and n are the combinations shown in [Table 1] to [Table 16].

In the formula (C-1), compounds wherein $R^5$ is a trifluoromethyl group, $R^8$ is a bromine atom, and $R^1$, $R^3$, $A^1$ and n are the combinations shown in [Table 1] to [Table 16].

In the formula (C-1), compounds wherein $R^5$ is a trifluoromethyl group, $R^8$ is a methyl group, and $R^1$, $R^3$, $A^1$ and n are the combinations shown in [Table 1] to [Table 16].

In the formula (C-1), compounds wherein $R^5$ is a pentafluoroethyl group, $R^8$ is a hydrogen atom, and $R^1$, $R^3$, $A^1$ and n are the combinations shown in [Table 1] to [Table 16].

In the formula (C-1), compounds wherein $R^5$ is a pentafluoroethyl group, $R^8$ is a chlorine atom, and $R^1$, $R^3$, $A^1$ and n are the combinations shown in [Table 1] to [Table 16].

In the formula (C-1), compounds wherein $R^5$ is a pentafluoroethyl group, $R^8$ is a bromine atom, and $R^1$, $R^3$, $A^1$ and n are the combinations shown in [Table 1] to [Table 16].

In the formula (C-1), compounds wherein $R^5$ is a pentafluoroethyl group, $R^8$ is a methyl group, and $R^1$, $R^3$, $A^1$ and n are the combinations shown in [Table 1] to [Table 16].

In the formula (C-1), compounds wherein $R^5$ is a heptafluoroisopropyl group, $R^8$ is a hydrogen atom, and $R^1$, $R^3$, $A^1$ and n are the combinations shown in [Table 1] to [Table 16].

In the formula (C-1), compounds wherein $R^5$ is a heptafluoroisopropyl group, $R^8$ is a chlorine atom, and $R^1$, $R^3$, $A^1$ and n are the combinations shown in [Table 1] to [Table 16].

In the formula (C-1), compounds wherein $R^5$ is a heptafluoroisopropyl group, $R^8$ is a bromine atom, and $R^1$, $R^3$, $A^1$ and n are the combinations shown in [Table 1] to [Table 16].

In the formula (C-1), compounds wherein $R^5$ is a heptafluoroisopropyl group, $R^8$ is a methyl group, and $R^1$, $R^3$, $A^1$ and n are the combinations shown in [Table 1] to [Table 16].

In the formula (C-1), compounds wherein $R^5$ is a trifluoromethoxy group, $R^8$ is a hydrogen atom, and $R^1$, $R^3$, $A^1$ and n are the combinations shown in [Table 1] to [Table 16].

In the formula (C-1), compounds wherein $R^5$ is a trifluoromethoxy group, $R^8$ is a chlorine atom, and $R^1$, $R^3$, $A^1$ and n are the combinations shown in [Table 1] to [Table 16].

In the formula (C-1), compounds wherein $R^5$ is a trifluoromethoxy group, $R^8$ is a bromine atom, and $R^1$, $R^3$, $A^1$ and n are the combinations shown in [Table 1] to [Table 16].

In the formula (C-1), compounds wherein $R^5$ is a trifluoromethoxy group, $R^8$ is a methyl group, and $R^1$, $R^3$, $A^1$ and n are the combinations shown in [Table 1] to [Table 16].

In the formula (C-1), compounds wherein $R^5$ is a trifluoromethylsulfanyl group, $R^8$ is a hydrogen atom, and $R^1$, $R^3$, $A^1$ and n are the combinations shown in [Table 1] to [Table 16].
In the formula (C-1), compounds wherein $R^5$ is a trifluoromethylsulfanyl group, $R^8$ is a chlorine atom, and $R^1$, $R^3$, $A^1$ and n are the combinations shown in [Table 1] to [Table 16].
In the formula (C-1), compounds wherein $R^5$ is a trifluoromethylsulfanyl group, $R^8$ is a bromine atom, and $R^1$, $R^3$, $A^1$ and n are the combinations shown in [Table 1] to [Table 16].
In the formula (C-1), compounds wherein $R^5$ is a trifluoromethylsulfanyl group, $R^8$ is a methyl group, and $R^1$, $R^3$, $A^1$ and n are the combinations shown in [Table 1] to [Table 16].
In the formula (C-1), compounds wherein $R^5$ is a trifluoromethylsulfinyl group, $R^8$ is a hydrogen atom, and $R^1$, $R^3$, $A^1$ and n are the combinations shown in [Table 1] to [Table 16].
In the formula (C-1), compounds wherein $R^5$ is a trifluoromethylsulfinyl group, $R^8$ is a chlorine atom, and $R^1$, $R^3$, $A^1$ and n are the combinations shown in [Table 1] to [Table 16].
In the formula (C-1), compounds wherein $R^5$ is a trifluoromethylsulfinyl group, $R^8$ is a bromine atom, and $R^1$, $R^3$, $A^1$ and n are the combinations shown in [Table 1] to [Table 16].
In the formula (C-1), compounds wherein $R^5$ is a trifluoromethylsulfinyl group, $R^8$ is a methyl group, and $R^1$, $R^3$, $A^1$ and n are the combinations shown in [Table 1] to [Table 16].
In the formula (C-1), compounds wherein $R^5$ is a trifluoromethylsulfonyl group, $R^8$ is a hydrogen atom, and $R^1$, $R^3$, $A^1$ and n are the combinations shown in [Table 1] to [Table 16].
In the formula (C-1), compounds wherein $R^5$ is a trifluoromethylsulfonyl group, $R^8$ is a chlorine atom, and $R^1$, $R^3$, $A^1$ and n are the combinations shown in [Table 1] to [Table 16].
In the formula (C-1), compounds wherein $R^5$ is a trifluoromethylsulfonyl group, $R^8$ is a bromine atom, and $R^1$, $R^3$, $A^1$ and n are the combinations shown in [Table 1] to [Table 16].
In the formula (C-1), compounds wherein $R^5$ is a trifluoromethylsulfonyl group, $R^8$ is a methyl group, and R, $R^3$, $A^1$ and n are the combinations shown in [Table 1] to [Table 16].
In the formula (C-2), (C-2)

wherein symbols represent the same meaning as in the formula (1), compounds wherein $R^6$ is a trifluoromethyl group, $R^8$ is a hydrogen atom, and $R^1$, $R^3$, $A^1$ and n are the combinations shown in [Table 1] to [Table 16].
In the formula (C-2), compounds wherein $R^6$ is a trifluoromethyl group, $R^8$ is a chlorine atom, and $R^1$, $R^3$, $A^1$ and n are the combinations shown in [Table 1] to [Table 16].
In the formula (C-2), compounds wherein $R^6$ is a trifluoromethyl group, $R^8$ is a bromine atom, and $R^1$, $R^3$, $A^1$ and n are the combinations shown in [Table 1] to [Table 16].
In the formula (C-2), compounds wherein $R^6$ is a trifluoromethyl group, $R^8$ is a methyl group, and $R^1$, $R^3$, $A^1$ and n are the combinations shown in [Table 1] to [Table 16].
In the formula (C-2), compounds wherein $R^6$ is a pentafluoroethyl group, $R^8$ is a hydrogen atom, and $R^1$, $R^3$, $A^1$ and n are the combinations shown in [Table 1] to [Table 16].
In the formula (C-2), compounds wherein $R^6$ is a pentafluoroethyl group, $R^8$ is a chlorine atom, and $R^1$, $R^3$, $A^1$ and n are the combinations shown in [Table 1] to [Table 16].
In the formula (C-2), compounds wherein $R^6$ is a pentafluoroethyl group, $R^8$ is a bromine atom, and $R^1$, $R^3$, $A^1$ and n are the combinations shown in [Table 1] to [Table 16].
In the formula (C-2), compounds wherein $R^6$ is a pentafluoroethyl group, $R^8$ is a methyl group, and $R^1$, $R^3$, $A^1$ and n are the combinations shown in [Table 1] to [Table 16].
In the formula (C-2), compounds wherein $R^6$ is a heptafluoroisopropyl group, $R^8$ is a hydrogen atom, and $R^1$, $R^3$, $A^1$ and n are the combinations shown in [Table 1] to [Table 16].
In the formula (C-2), compounds wherein $R^6$ is a heptafluoroisopropyl group, $R^8$ is a chlorine atom, and $R^1$, $R^3$, $A^1$ and n are the combinations shown in [Table 1] to [Table 16].
In the formula (C-2), compounds wherein $R^6$ is a heptafluoroisopropyl group, $R^8$ is a bromine atom, and $R^1$, $R^3$, $A^1$ and n are the combinations shown in [Table 1] to [Table 16].
In the formula (C-2), compounds wherein $R^6$ is a heptafluoroisopropyl group, $R^8$ is a methyl group, and $R^1$, $R^3$, $A^1$ and n are the combinations shown in [Table 1] to [Table 16].
In the formula (C-2), compounds wherein $R^6$ is a trifluoromethoxy group, $R^8$ is a hydrogen atom, and $R^1$, $R^3$, $A^1$ and n are the combinations shown in [Table 1] to [Table 16].
In the formula (C-2), compounds wherein $R^6$ is a trifluoromethoxy group, $R^8$ is a chlorine atom, and $R^1$, $R^3$, $A^1$ and n are the combinations shown in [Table 1] to [Table 16].
In the formula (C-2), compounds wherein $R^6$ is a trifluoromethoxy group, $R^8$ is a bromine atom, and $R^1$, $R^3$, $A^1$ and n are the combinations shown in [Table 1] to [Table 16].
In the formula (C-2), compounds wherein $R^6$ is a trifluoromethoxy group, $R^8$ is a methyl group, and $R^1$, $R^3$, $A^1$ and n are the combinations shown in [Table 1] to [Table 16].
In the formula (C-2), compounds wherein $R^6$ is a trifluoromethylsulfanyl group, $R^8$ is a hydrogen atom, and $R^1$, $R^3$, $A^1$ and n are the combinations shown in [Table 1] to [Table 16].
In the formula (C-2), compounds wherein $R^6$ is a trifluoromethylsulfanyl group, $R^8$ is a chlorine atom, and $R^1$, $R^3$, $A^1$ and n are the combinations shown in [Table 1] to [Table 16].
In the formula (C-2), compounds wherein $R^6$ is a trifluoromethylsulfanyl group, $R^8$ is a bromine atom, and $R^1$, $R^3$, $A^1$ and n are the combinations shown in [Table 1] to [Table 16].
In the formula (C-2), compounds wherein $R^6$ is a trifluoromethylsulfanyl group, $R^8$ is a methyl group, and $R^1$, $R^3$, $A^1$ and n are the combinations shown in [Table 1] to [Table 16].
In the formula (C-2), compounds wherein $R^6$ is a trifluoromethylsulfinyl group, $R^8$ is a hydrogen atom, and $R^1$, $R^3$, $A^1$ and n are the combinations shown in [Table 1] to [Table 16].
In the formula (C-2), compounds wherein $R^6$ is a trifluoromethylsulfinyl group, $R^8$ is a chlorine atom, and $R^1$, $R^3$, $A^1$ and n are the combinations shown in [Table 1] to [Table 16].
In the formula (C-2), compounds wherein $R^6$ is a trifluoromethylsulfinyl group, $R^8$ is a bromine atom, and $R^1$, $R^3$, $A^1$ and n are the combinations shown in [Table 1] to [Table 16].
In the formula (C-2), compounds wherein $R^6$ is a trifluoromethylsulfinyl group, $R^8$ is a methyl group, and $R^1$, $R^3$, $A^1$ and n are the combinations shown in [Table 1] to [Table 16].
In the formula (C-2), compounds wherein $R^6$ is a trifluoromethylsulfonyl group, $R^8$ is a hydrogen atom, and $R^1$, $R^3$, $A^1$ and n are the combinations shown in [Table 1] to [Table 16].
In the formula (C-2), compounds wherein $R^6$ is a trifluoromethylsulfonyl group, $R^8$ is a chlorine atom, and $R^1$, $R^3$, $A^1$ and n are the combinations shown in [Table 1] to [Table 16].
In the formula (C-2), compounds wherein $R^6$ is a trifluoromethylsulfonyl group, $R^8$ is a bromine atom, and $R^1$, $R^3$, $A^1$ and n are the combinations shown in [Table 1] to [Table 16].
In the formula (C-2), compounds wherein $R^6$ is a trifluoromethylsulfonyl group, $R^8$ is a methyl group, and $R^1$, $R^3$, $A^1$ and n are the combinations shown in [Table 1] to [Table 16].

In the formula (D-1), (D-1)

[Chemical structure showing imidazo[1,2-a]pyrimidine with substituents R¹, R³, R⁵, R⁸, A¹, and (O)ₙS]

wherein symbols represent the same meaning as in the formula (1), compounds wherein $R^5$ is a trifluoromethyl group, $R^8$ is a hydrogen atom, and $R^1$, $R^3$, $A^1$ and n are the combinations shown in [Table 1] to [Table 16].

In the formula (D-1), compounds wherein $R^5$ is a trifluoromethyl group, $R^8$ is a chlorine atom, and $R^1$, $R^3$, $A^1$ and n are the combinations shown in [Table 1] to [Table 16].

In the formula (D-1), compounds wherein $R^5$ is a trifluoromethyl group, $R^8$ is a bromine atom, and $R^1$, $R^3$, $A^1$ and n are the combinations shown in [Table 1] to [Table 16].

In the formula (D-1), compounds wherein $R^5$ is a trifluoromethyl group, $R^8$ is a methyl group, and $R^1$, $R^3$, $A^1$ and n are the combinations shown in [Table 1] to [Table 16].

In the formula (D-1), compounds wherein $R^5$ is a pentafluoroethyl group, $R^8$ is a hydrogen atom, and $R^1$, $R^3$, $A^1$ and n are the combinations shown in [Table 1] to [Table 16].

In the formula (D-1), compounds wherein $R^5$ is a pentafluoroethyl group, $R^8$ is a chlorine atom, and $R^1$, $R^3$, $A^1$ and n are the combinations shown in [Table 1] to [Table 16].

In the formula (D-1), compounds wherein $R^5$ is a pentafluoroethyl group, $R^8$ is a bromine atom, and $R^1$, $R^3$, $A^1$ and n are the combinations shown in [Table 1] to [Table 16].

In the formula (D-1), compounds wherein $R^5$ is a pentafluoroethyl group, $R^8$ is a methyl group, and $R^1$, $R^3$, $A^1$ and n are the combinations shown in [Table 1] to [Table 16].

In the formula (D-1), compounds wherein $R^5$ is a heptafluoroisopropyl group, $R^8$ is a hydrogen atom, and $R^1$, $R^3$, $A^1$ and n are the combinations shown in [Table 1] to [Table 16].

In the formula (D-1), compounds wherein $R^5$ is a heptafluoroisopropyl group, $R^8$ is a chlorine atom, and $R^1$, $R^3$, $A^1$ and n are the combinations shown in [Table 1] to [Table 16].

In the formula (D-1), compounds wherein $R^5$ is a heptafluoroisopropyl group, $R^8$ is a bromine atom, and $R^1$, $R^3$, $A^1$ and n are the combinations shown in [Table 1] to [Table 16].

In the formula (D-1), compounds wherein $R^5$ is a heptafluoroisopropyl group, $R^8$ is a methyl group, and $R^1$, $R^3$, $A^1$ and n are the combinations shown in [Table 1] to [Table 16].

In the formula (D-1), compounds wherein $R^5$ is a trifluoromethoxy group, $R^8$ is a hydrogen atom, and $R^1$, $R^3$, $A^1$ and n are the combinations shown in [Table 1] to [Table 16].

In the formula (D-1), compounds wherein $R^5$ is a trifluoromethoxy group, $R^8$ is a chlorine atom, and $R^1$, $R^3$, $A^1$ and n are the combinations shown in [Table 1] to [Table 16].

In the formula (D-1), compounds wherein $R^5$ is a trifluoromethoxy group, $R^8$ is a bromine atom, and $R^1$, $R^3$, $A^1$ and n are the combinations shown in [Table 1] to [Table 16].

In the formula (D-1), compounds wherein $R^5$ is a trifluoromethoxy group, $R^8$ is a methyl group, and $R^1$, $R^3$, $A^1$ and n are the combinations shown in [Table 1] to [Table 16].

In the formula (D-1), compounds wherein $R^5$ is a trifluoromethylsulfanyl group, $R^8$ is a hydrogen atom, and $R^1$, $R^3$, $A^1$ and n are the combinations shown in [Table 1] to [Table 16].

In the formula (D-1), compounds wherein $R^5$ is a trifluoromethylsulfanyl group, $R^8$ is a chlorine atom, and $R^1$, $R^3$, $A^1$ and n are the combinations shown in [Table 1] to [Table 16].

In the formula (D-1), compounds wherein $R^5$ is a trifluoromethylsulfanyl group, $R^8$ is a bromine atom, and $R^1$, $R^3$, $A^1$ and n are the combinations shown in [Table 1] to [Table 16].

In the formula (D-1), compounds wherein $R^5$ is a trifluoromethylsulfanyl group, $R^8$ is a methyl group, and $R^1$, $R^3$, $A^1$ and n are the combinations shown in [Table 1] to [Table 16].

In the formula (D-1), compounds wherein $R^5$ is a trifluoromethylsulfinyl group, $R^8$ is a hydrogen atom, and $R^1$, $R^3$, $A^1$ and n are the combinations shown in [Table 1] to [Table 16].

In the formula (D-1), compounds wherein $R^5$ is a trifluoromethylsulfinyl group, $R^8$ is a chlorine atom, and $R^1$, $R^3$, $A^1$ and n are the combinations shown in [Table 1] to [Table 16].

In the formula (D-1), compounds wherein $R^5$ is a trifluoromethylsulfinyl group, $R^8$ is a bromine atom, and $R^1$, $R^3$, $A^1$ and n are the combinations shown in [Table 1] to [Table 16].

In the formula (D-1), compounds wherein $R^5$ is a trifluoromethylsulfinyl group, $R^8$ is a methyl group, and $R^1$, $R^3$, $A^1$ and n are the combinations shown in [Table 1] to [Table 16].

In the formula (D-1), compounds wherein $R^5$ is a trifluoromethylsulfonyl group, $R^8$ is a hydrogen atom, and $R^1$, $R^3$, $A^1$ and n are the combinations shown in [Table 1] to [Table 16].

In the formula (D-1), compounds wherein $R^5$ is a trifluoromethylsulfonyl group, $R^8$ is a chlorine atom, and $R^1$, $R^3$, $A^1$ and n are the combinations shown in [Table 1] to [Table 16].

In the formula (D-1), compounds wherein $R^5$ is a trifluoromethylsulfonyl group, $R^8$ is a bromine atom, and $R^1$, $R^3$, $A^1$ and n are the combinations shown in [Table 1] to [Table 16].

In the formula (D-1), compounds wherein $R^5$ is a trifluoromethylsulfonyl group, $R^8$ is a methyl group, and $R^1$, $R^3$, $A^1$ and n are the combinations shown in [Table 1] to [Table 16].

In the formula (D-2), (D-2)

[Chemical structure showing imidazo[1,2-a]pyrimidine with substituents R¹, R³, R⁶, R⁸, A¹, and (O)ₙS]

wherein symbols represent the same meaning as in the formula (1), compounds wherein $R^6$ is a trifluoromethyl group, $R^8$ is a hydrogen atom, and $R^1$, $R^3$, $A^1$ and n are the combinations shown in [Table 1] to [Table 16].

In the formula (D-2), compounds wherein $R^6$ is a trifluoromethyl group, $R^8$ is a chlorine atom, and $R^1$, $R^3$, $A^1$ and n are the combinations shown in [Table 1] to [Table 16].

In the formula (D-2), compounds wherein $R^6$ is a trifluoromethyl group, $R^8$ is a bromine atom, and $R^1$, $R^3$, $A^1$ and n are the combinations shown in [Table 1] to [Table 16].

In the formula (D-2), compounds wherein $R^6$ is a trifluoromethyl group, $R^8$ is a methyl group, and $R^1$, $R^3$, $A^1$ and n are the combinations shown in [Table 1] to [Table 16].

In the formula (D-2), compounds wherein $R^6$ is a pentafluoroethyl group, $R^8$ is a hydrogen atom, and $R^1$, $R^3$, $A^1$ and n are the combinations shown in [Table 1] to [Table 16].

In the formula (D-2), compounds wherein $R^6$ is a pentafluoroethyl group, $R^8$ is a chlorine atom, and $R^1$, $R^3$, $A^1$ and n are the combinations shown in [Table 1] to [Table 16].

In the formula (D-2), compounds wherein $R^6$ is a pentafluoroethyl group, $R^8$ is a bromine atom, and $R^1$, $R^3$, $A^1$ and n are the combinations shown in [Table 1] to [Table 16].

In the formula (D-2), compounds wherein $R^6$ is a pentafluoroethyl group, $R^8$ is a methyl group, and $R^1$, $R^3$, $A^1$ and n are the combinations shown in [Table 1] to [Table 16].

In the formula (D-2), compounds wherein $R^6$ is a heptafluoroisopropyl group, $R^8$ is a hydrogen atom, and $R^1$, $R^3$, $A^1$ and n are the combinations shown in [Table 1] to [Table 16].

In the formula (D-2), compounds wherein $R^6$ is a heptafluoroisopropyl group, $R^8$ is a chlorine atom, and $R^1$, $R^3$, $A^1$ and n are the combinations shown in [Table 1] to [Table 16].

In the formula (D-2), compounds wherein $R^6$ is a heptafluoroisopropyl group, $R^8$ is a bromine atom, and $R^1$, $R^3$, $A^1$ and n are the combinations shown in [Table 1] to [Table 16].

In the formula (D-2), compounds wherein $R^6$ is a heptafluoroisopropyl group, $R^8$ is a methyl group, and $R^1$, $R^3$, $A^1$ and n are the combinations shown in [Table 1] to [Table 16].

In the formula (D-2), compounds wherein $R^6$ is a trifluoromethoxy group, $R^8$ is a hydrogen atom, and $R^1$, $R^3$, $A^1$ and n are the combinations shown in [Table 1] to [Table 16].

In the formula (D-2), compounds wherein $R^6$ is a trifluoromethoxy group, $R^8$ is a chlorine atom, and $R^1$, $R^3$, $A^1$ and n are the combinations shown in [Table 1] to [Table 16].

In the formula (D-2), compounds wherein $R^6$ is a trifluoromethoxy group, $R^8$ is a bromine atom, and $R^1$, $R^3$, $A^1$ and n are the combinations shown in [Table 1] to [Table 16].

In the formula (D-2), compounds wherein $R^6$ is a trifluoromethoxy group, $R^8$ is a methyl group, and $R^1$, $R^3$, $A^1$ and n are the combinations shown in [Table 1] to [Table 16].

In the formula (D-2), compounds wherein $R^6$ is a trifluoromethylsulfanyl group, $R^8$ is a hydrogen atom, and $R^1$, $R^3$, $A^1$ and n are the combinations shown in [Table 1] to [Table 16].

In the formula (D-2), compounds wherein $R^6$ is a trifluoromethylsulfanyl group, $R^8$ is a chlorine atom, and $R^1$, $R^3$, $A^1$ and n are the combinations shown in [Table 1] to [Table 16].

In the formula (D-2), compounds wherein $R^6$ is a trifluoromethylsulfanyl group, $R^8$ is a bromine atom, and $R^1$, $R^3$, $A^1$ and n are the combinations shown in [Table 1] to [Table 16].

In the formula (D-2), compounds wherein $R^6$ is a trifluoromethylsulfanyl group, $R^8$ is a methyl group, and $R^1$, $R^3$, $A^1$ and n are the combinations shown in [Table 1] to [Table 16].

In the formula (D-2), compounds wherein $R^6$ is a trifluoromethylsulfinyl group, $R^8$ is a hydrogen atom, and $R^1$, $R^3$, $A^1$ and n are the combinations shown in [Table 1] to [Table 16].

In the formula (D-2), compounds wherein $R^6$ is a trifluoromethylsulfinyl group, $R^8$ is a chlorine atom, and $R^1$, $R^3$, $A^1$ and n are the combinations shown in [Table 1] to [Table 16].

In the formula (D-2), compounds wherein $R^6$ is a trifluoromethylsulfinyl group, $R^8$ is a bromine atom, and $R^1$, $R^3$, $A^1$ and n are the combinations shown in [Table 1] to [Table 16].

In the formula (D-2), compounds wherein $R^6$ is a trifluoromethylsulfinyl group, $R^8$ is a methyl group, and $R^1$, $R^3$, $A^1$ and n are the combinations shown in [Table 1] to [Table 16].

In the formula (D-2), compounds wherein $R^6$ is a trifluoromethylsulfonyl group, $R^8$ is a hydrogen atom, and $R^1$, $R^3$, $A^1$ and n are the combinations shown in [Table 1] to [Table 16].

In the formula (D-2), compounds wherein $R^6$ is a trifluoromethylsulfonyl group, $R^8$ is a chlorine atom, and $R^1$, $R^3$, $A^1$ and n are the combinations shown in [Table 1] to [Table 16].

In the formula (D-2), compounds wherein $R^6$ is a trifluoromethylsulfonyl group, $R^8$ is a bromine atom, and $R^1$, $R^3$, $A^1$ and n are the combinations shown in [Table 1] to [Table 16].

In the formula (D-2), compounds wherein $R^6$ is a trifluoromethylsulfonyl group, $R^8$ is a methyl group, and $R^1$, $R^3$, $A^1$ and n are the combinations shown in [Table 1] to [Table 16].

In the formula (E-1), (E-1)

wherein symbols represent the same meaning as in the formula (1), compounds wherein $R^5$ is a trifluoromethyl group, $R^9$ is a hydrogen atom, and $R^1$, $R^3$, $A^1$ and n are the combinations shown in [Table 1] to [Table 16].

In the formula (E-1), compounds wherein $R^5$ is a trifluoromethyl group, $R^9$ is a chlorine atom, and $R^1$, $R^3$, $A^1$ and n are the combinations shown in [Table 1] to [Table 16].

In the formula (E-1), compounds wherein $R^5$ is a trifluoromethyl group, $R^9$ is a bromine atom, and $R^1$, $R^3$, $A^1$ and n are the combinations shown in [Table 1] to [Table 16].

In the formula (E-1), compounds wherein $R^5$ is a trifluoromethyl group, $R^9$ is a methyl group, and $R^1$, $R^3$, $A^1$ and n are the combinations shown in [Table 1] to [Table 16].

In the formula (E-1), compounds wherein $R^5$ is a pentafluoroethyl group, $R^9$ is a hydrogen atom, and $R^1$, $R^3$, $A^1$ and n are the combinations shown in [Table 1] to [Table 16].

In the formula (E-1), compounds wherein $R^5$ is a pentafluoroethyl group, $R^9$ is a chlorine atom, and $R^1$, $R^3$, $A^1$ and n are the combinations shown in [Table 1] to [Table 16].

In the formula (E-1), compounds wherein $R^5$ is a pentafluoroethyl group, $R^9$ is a bromine atom, and $R^1$, $R^3$, $A^1$ and n are the combinations shown in [Table 1] to [Table 16].

In the formula (E-1), compounds wherein $R^5$ is a pentafluoroethyl group, $R^9$ is a methyl group, and $R^1$, $R^3$, $A^1$ and n are the combinations shown in [Table 1] to [Table 16].

In the formula (E-1), compounds wherein $R^5$ is a heptafluoroisopropyl group, $R^9$ is a hydrogen atom, and $R^1$, $R^3$, $A^1$ and n are the combinations shown in [Table 1] to [Table 16].

In the formula (E-1), compounds wherein $R^5$ is a heptafluoroisopropyl group, $R^9$ is a chlorine atom, and $R^1$, $R^3$, $A^1$ and n are the combinations shown in [Table 1] to [Table 16].

In the formula (E-1), compounds wherein $R^5$ is a heptafluoroisopropyl group, $R^9$ is a bromine atom, and $R^1$, $R^3$, $A^1$ and n are the combinations shown in [Table 1] to [Table 16].

In the formula (E-1), compounds wherein $R^5$ is a heptafluoroisopropyl group, $R^9$ is a methyl group, and R, $R^3$, $A^1$ and n are the combinations shown in [Table 1] to [Table 16].

In the formula (E-1), compounds wherein $R^5$ is a trifluoromethoxy group, $R^9$ is a hydrogen atom, and $R^1$, $R^3$, $A^1$ and n are the combinations shown in [Table 1] to [Table 16].

In the formula (E-1), compounds wherein $R^5$ is a trifluoromethoxy group, $R^9$ is a chlorine atom, and $R^1$, $R^3$, $A^1$ and n are the combinations shown in [Table 1] to [Table 16].

In the formula (E-1), compounds wherein $R^5$ is a trifluoromethoxy group, $R^9$ is a bromine atom, and $R^1$, $R^3$, $A^1$ and n are the combinations shown in [Table 1] to [Table 16].

In the formula (E-1), compounds wherein $R^5$ is a trifluoromethoxy group, $R^9$ is a methyl group, and $R^1$, $R^3$, $A^1$ and n are the combinations shown in [Table 1] to [Table 16].

In the formula (E-1), compounds wherein $R^5$ is a trifluoromethylsulfanyl group, $R^9$ is a hydrogen atom, and $R^1$, $R^3$, $A^1$ and n are the combinations shown in [Table 1] to [Table 16].

In the formula (E-1), compounds wherein $R^5$ is a trifluoromethylsulfanyl group, $R^9$ is a chlorine atom, and $R^1$, $R^3$, $A^1$ and n are the combinations shown in [Table 1] to [Table 16].
In the formula (E-1), compounds wherein $R^5$ is a trifluoromethylsulfanyl group, $R^9$ is a bromine atom, and R, $R^3$, $A^1$ and n are the combinations shown in [Table 1] to [Table 16].
In the formula (E-1), compounds wherein $R^5$ is a trifluoromethylsulfanyl group, $R^9$ is a methyl group, and $R^1$, $R^3$, $A^1$ and n are the combinations shown in [Table 1] to [Table 16].
In the formula (E-1), compounds wherein $R^5$ is a trifluoromethylsulfinyl group, $R^9$ is a hydrogen atom, and $R^1$, $R^3$, $A^1$ and n are the combinations shown in [Table 1] to [Table 16].
In the formula (E-1), compounds wherein $R^5$ is a trifluoromethylsulfinyl group, $R^9$ is a chlorine atom, and $R^1$, $R^3$, $A^1$ and n are the combinations shown in [Table 1] to [Table 16].
In the formula (E-1), compounds wherein $R^5$ is a trifluoromethylsulfinyl group, $R^9$ is a bromine atom, and $R^1$, $R^3$, $A^1$ and n are the combinations shown in [Table 1] to [Table 16].
In the formula (E-1), compounds wherein $R^5$ is a trifluoromethylsulfinyl group, $R^9$ is a methyl group, and $R^1$, $R^3$, $A^1$ and n are the combinations shown in [Table 1] to [Table 16].
In the formula (E-1), compounds wherein $R^5$ is a trifluoromethylsulfonyl group, $R^9$ is a hydrogen atom, and $R^1$, $R^3$, $A^1$ and n are the combinations shown in [Table 1] to [Table 16].
In the formula (E-1), compounds wherein $R^5$ is a trifluoromethylsulfonyl group, $R^9$ is a chlorine atom, and $R^1$, $R^3$, $A^1$ and n are the combinations shown in [Table 1] to [Table 16].
In the formula (E-1), compounds wherein $R^5$ is a trifluoromethylsulfonyl group, $R^9$ is a bromine atom, and $R^1$, $R^3$, $A^1$ and n are the combinations shown in [Table 1] to [Table 16].
In the formula (E-1), compounds wherein $R^5$ is a trifluoromethylsulfonyl group, $R^9$ is a methyl group, and $R^1$, $R^3$, $A^1$ and n are the combinations shown in [Table 1] to [Table 16].
In the formula (E-2), (E-2)

wherein symbols represent the same meaning as in the formula (1), compounds wherein $R^6$ is a trifluoromethyl group, $R^9$ is a hydrogen atom, and $R^1$, $R^3$, $A^1$ and n are the combinations shown in [Table 1] to [Table 16].
In the formula (E-2), compounds wherein $R^6$ is a trifluoromethyl group, $R^9$ is a chlorine atom, and $R^1$, $R^3$, $A^1$ and n are the combinations shown in [Table 1] to [Table 16].
In the formula (E-2), compounds wherein $R^6$ is a trifluoromethyl group, $R^9$ is a bromine atom, and $R^1$, $R^3$, $A^1$ and n are the combinations shown in [Table 1] to [Table 16].
In the formula (E-2), compounds wherein $R^6$ is a trifluoromethyl group, $R^9$ is a methyl group, and $R^1$, $R^3$, $A^1$ and n are the combinations shown in [Table 1] to [Table 16].
In the formula (E-2), compounds wherein $R^6$ is a pentafluoroethyl group, $R^9$ is a hydrogen atom, and $R^1$, $R^3$, $A^1$ and n are the combinations shown in [Table 1] to [Table 16].
In the formula (E-2), compounds wherein $R^6$ is a pentafluoroethyl group, $R^9$ is a chlorine atom, and $R^1$, $R^3$, $A^1$ and n are the combinations shown in [Table 1] to [Table 16].
In the formula (E-2), compounds wherein $R^6$ is a pentafluoroethyl group, $R^9$ is a bromine atom, and $R^1$, $R^3$, $A^1$ and n are the combinations shown in [Table 1] to [Table 16].
In the formula (E-2), compounds wherein $R^6$ is a pentafluoroethyl group, $R^9$ is a methyl group, and $R^1$, $R^3$, $A^1$ and n are the combinations shown in [Table 1] to [Table 16].
In the formula (E-2), compounds wherein $R^6$ is a heptafluoroisopropyl group, $R^9$ is a hydrogen atom, and $R^1$, $R^3$, $A^1$ and n are the combinations shown in [Table 1] to [Table 16].
In the formula (E-2), compounds wherein $R^6$ is a heptafluoroisopropyl group, $R^9$ is a chlorine atom, and $R^1$, $R^3$, $A^1$ and n are the combinations shown in [Table 1] to [Table 16].
In the formula (E-2), compounds wherein $R^6$ is a heptafluoroisopropyl group, $R^9$ is a bromine atom, and $R^1$, $R^3$, $A^1$ and n are the combinations shown in [Table 1] to [Table 16].
In the formula (E-2), compounds wherein $R^6$ is a heptafluoroisopropyl group, $R^9$ is a methyl group, and $R^1$, $R^3$, $A^1$ and n are the combinations shown in [Table 1] to [Table 16].
In the formula (E-2), compounds wherein $R^6$ is a trifluoromethoxy group, $R^9$ is a hydrogen atom, and $R^1$, $R^3$, $A^1$ and n are the combinations shown in [Table 1] to [Table 16].
In the formula (E-2), compounds wherein $R^6$ is a trifluoromethoxy group, $R^9$ is a chlorine atom, and $R^1$, $R^3$, $A^1$ and n are the combinations shown in [Table 1] to [Table 16].
In the formula (E-2), compounds wherein $R^6$ is a trifluoromethoxy group, $R^9$ is a bromine atom, and $R^1$, $R^3$, $A^1$ and n are the combinations shown in [Table 1] to [Table 16].
In the formula (E-2), compounds wherein $R^6$ is a trifluoromethoxy group, $R^9$ is a methyl group, and $R^1$, $R^3$, $A^1$ and n are the combinations shown in [Table 1] to [Table 16].
In the formula (E-2), compounds wherein $R^6$ is a trifluoromethylsulfanyl group, $R^9$ is a hydrogen atom, and $R^1$, $R^3$, $A^1$ and n are the combinations shown in [Table 1] to [Table 16].
In the formula (E-2), compounds wherein $R^6$ is a trifluoromethylsulfanyl group, $R^9$ is a chlorine atom, and $R^1$, $R^3$, $A^1$ and n are the combinations shown in [Table 1] to [Table 16].
In the formula (E-2), compounds wherein $R^6$ is a trifluoromethylsulfanyl group, $R^9$ is a bromine atom, and R, $R^3$, $A^1$ and n are the combinations shown in [Table 1] to [Table 16].
In the formula (E-2), compounds wherein $R^6$ is a trifluoromethylsulfanyl group, $R^9$ is a methyl group, and $R^1$, $R^3$, $A^1$ and n are the combinations shown in [Table 1] to [Table 16].
In the formula (E-2), compounds wherein $R^6$ is a trifluoromethylsulfinyl group, $R^9$ is a hydrogen atom, and $R^1$, $R^3$, $A^1$ and n are the combinations shown in [Table 1] to [Table 16].
In the formula (E-2), compounds wherein $R^6$ is a trifluoromethylsulfinyl group, $R^9$ is a chlorine atom, and $R^1$, $R^3$, $A^1$ and n are the combinations shown in [Table 1] to [Table 16].
In the formula (E-2), compounds wherein $R^6$ is a trifluoromethylsulfinyl group, $R^9$ is a bromine atom, and $R^1$, $R^3$, $A^1$ and n are the combinations shown in [Table 1] to [Table 16].
In the formula (E-2), compounds wherein $R^6$ is a trifluoromethylsulfinyl group, $R^9$ is a methyl group, and $R^1$, $R^3$, $A^1$ and n are the combinations shown in [Table 1] to [Table 16].
In the formula (E-2), compounds wherein $R^6$ is a trifluoromethylsulfonyl group, $R^9$ is a hydrogen atom, and $R^1$, $R^3$, $A^1$ and n are the combinations shown in [Table 1] to [Table 16].
In the formula (E-2), compounds wherein $R^6$ is a trifluoromethylsulfonyl group, $R^9$ is a chlorine atom, and $R^1$, $R^3$, $A^1$ and n are the combinations shown in [Table 1] to [Table 16].
In the formula (E-2), compounds wherein $R^6$ is a trifluoromethylsulfonyl group, $R^9$ is a bromine atom, and $R^1$, $R^3$, $A^1$ and n are the combinations shown in [Table 1] to [Table 16].
In the formula (E-2), compounds wherein $R^6$ is a trifluoromethylsulfonyl group, $R^9$ is a methyl group, and $R^1$, $R^3$, $A^1$ and n are the combinations shown in [Table 1] to [Table 16].

In the formula (F-1), $$\text{(F-1)}$$

wherein symbols represent the same meaning as in the formula (1), compounds wherein $R^5$ is a trifluoromethyl group, $R^8$ is a hydrogen atom, and $R^1$, $R^3$, $A^1$ and n are the combinations shown in [Table 1] to [Table 16].

In the formula (F-1), compounds wherein $R^1$ is a trifluoromethyl group, $R^8$ is a chlorine atom, and $R^1$, $R^3$, $A^1$ and n are the combinations shown in [Table 1] to [Table 16].

In the formula (F-1), compounds wherein $R^5$ is a trifluoromethyl group, $R^8$ is a bromine atom, and $R^1$, $R^3$, $A^1$ and n are the combinations shown in [Table 1] to [Table 16].

In the formula (F-1), compounds wherein $R^5$ is a trifluoromethyl group, $R^8$ is a methyl group, and $R^1$, $R^3$, $A^1$ and n are the combinations shown in [Table 1] to [Table 16].

In the formula (F-1), compounds wherein $R^5$ is a pentafluoroethyl group, $R^8$ is a hydrogen atom, and $R^1$, $R^3$, $A^1$ and n are the combinations shown in [Table 1] to [Table 16].

In the formula (F-1), compounds wherein $R^5$ is a pentafluoroethyl group, $R^8$ is a chlorine atom, and $R^1$, $R^3$, $A^1$ and n are the combinations shown in [Table 1] to [Table 16].

In the formula (F-1), compounds wherein $R^5$ is a pentafluoroethyl group, $R^8$ is a bromine atom, and $R^1$, $R^3$, $A^1$ and n are the combinations shown in [Table 1] to [Table 16].

In the formula (F-1), compounds wherein $R^5$ is a pentafluoroethyl group, $R^8$ is a methyl group, and $R^1$, $R^3$, $A^1$ and n are the combinations shown in [Table 1] to [Table 16].

In the formula (F-1), compounds wherein $R^5$ is a heptafluoroisopropyl group, $R^8$ is a hydrogen atom, and $R^1$, $R^3$, $A^1$ and n are the combinations shown in [Table 1] to [Table 16].

In the formula (F-1), compounds wherein $R^5$ is a heptafluoroisopropyl group, $R^8$ is a chlorine atom, and $R^1$, $R^3$, $A^1$ and n are the combinations shown in [Table 1] to [Table 16].

In the formula (F-1), compounds wherein $R^5$ is a heptafluoroisopropyl group, $R^8$ is a bromine atom, and $R^1$, $R^3$, $A^1$ and n are the combinations shown in [Table 1] to [Table 16].

In the formula (F-1), compounds wherein $R^5$ is a heptafluoroisopropyl group, $R^8$ is a methyl group, and $R^1$, $R^3$, $A^1$ and n are the combinations shown in [Table 1] to [Table 16].

In the formula (F-1), compounds wherein $R^5$ is a trifluoromethoxy group, $R^8$ is a hydrogen atom, and $R^1$, $R^3$, $A^1$ and n are the combinations shown in [Table 1] to [Table 16].

In the formula (F-1), compounds wherein $R^5$ is a trifluoromethoxy group, $R^8$ is a chlorine atom, and $R^1$, $R^3$, $A^1$ and n are the combinations shown in [Table 1] to [Table 16].

In the formula (F-1), compounds wherein $R^5$ is a trifluoromethoxy group, $R^8$ is a bromine atom, and $R^1$, $R^3$, $A^1$ and n are the combinations shown in [Table 1] to [Table 16].

In the formula (F-1), compounds wherein $R^5$ is a trifluoromethoxy group, $R^8$ is a methyl group, and $R^1$, $R^3$, $A^1$ and n are the combinations shown in [Table 1] to [Table 16].

In the formula (F-1), compounds wherein $R^5$ is a trifluoromethylsulfanyl group, $R^8$ is a hydrogen atom, and $R^1$, $R^3$, $A^1$ and n are the combinations shown in [Table 1] to [Table 16].

In the formula (F-1), compounds wherein $R^5$ is a trifluoromethylsulfanyl group, $R^8$ is a chlorine atom, and $R^1$, $R^3$, $A^1$ and n are the combinations shown in [Table 1] to [Table 16].

In the formula (F-1), compounds wherein $R^5$ is a trifluoromethylsulfanyl group, $R^8$ is a bromine atom, and $R^1$, $R^3$, $A^1$ and n are the combinations shown in [Table 1] to [Table 16].

In the formula (F-1), compounds wherein $R^5$ is a trifluoromethylsulfanyl group, $R^8$ is a methyl group, and $R^1$, $R^3$, $A^1$ and n are the combinations shown in [Table 1] to [Table 16].

In the formula (F-1), compounds wherein $R^5$ is a trifluoromethylsulfinyl group, $R^8$ is a hydrogen atom, and $R^1$, $R^3$, $A^1$ and n are the combinations shown in [Table 1] to [Table 16].

In the formula (F-1), compounds wherein $R^5$ is a trifluoromethylsulfinyl group, $R^8$ is a chlorine atom, and $R^1$, $R^3$, $A^1$ and n are the combinations shown in [Table 1] to [Table 16].

In the formula (F-1), compounds wherein $R^5$ is a trifluoromethylsulfinyl group, $R^8$ is a bromine atom, and $R^1$, $R^3$, $A^1$ and n are the combinations shown in [Table 1] to [Table 16].

In the formula (F-1), compounds wherein $R^5$ is a trifluoromethylsulfinyl group, $R^8$ is a methyl group, and $R^1$, $R^3$, $A^1$ and n are the combinations shown in [Table 1] to [Table 16].

In the formula (F-1), compounds wherein $R^5$ is a trifluoromethylsulfonyl group, $R^8$ is a hydrogen atom, and $R^1$, $R^3$, $A^1$ and n are the combinations shown in [Table 1] to [Table 16].

In the formula (F-1), compounds wherein $R^5$ is a trifluoromethylsulfonyl group, $R^8$ is a chlorine atom, and $R^1$, $R^3$, $A^1$ and n are the combinations shown in [Table 1] to [Table 16].

In the formula (F-1), compounds wherein $R^5$ is a trifluoromethylsulfonyl group, $R^8$ is a bromine atom, and $R^1$, $R^3$, $A^1$ and n are the combinations shown in [Table 1] to [Table 16].

In the formula (F-1), compounds wherein $R^5$ is a trifluoromethylsulfonyl group, $R^8$ is a methyl group, and $R^1$, $R^3$, $A^1$ and n are the combinations shown in [Table 1] to [Table 16].

In the formula (F-2), $$\text{(F-2)}$$

wherein symbols represent the same meaning as in the formula (1), compounds wherein $R^6$ is a trifluoromethyl group, $R^8$ is a hydrogen atom, and $R^1$, $R^3$, $A^1$ and n are the combinations shown in [Table 1] to [Table 16].

In the formula (F-2), compounds wherein $R^6$ is a trifluoromethyl group, $R^8$ is a chlorine atom, and $R^1$, $R^3$, $A^1$ and n are the combinations shown in [Table 1] to [Table 16].

In the formula (F-2), compounds wherein $R^6$ is a trifluoromethyl group, $R^8$ is a bromine atom, and $R^1$, $R^3$, $A^1$ and n are the combinations shown in [Table 1] to [Table 16].

In the formula (F-2), compounds wherein $R^6$ is a trifluoromethyl group, $R^8$ is a methyl group, and $R^1$, $R^3$, $A^1$ and n are the combinations shown in [Table 1] to [Table 16].

In the formula (F-2), compounds wherein $R^6$ is a pentafluoroethyl group, $R^8$ is a hydrogen atom, and $R^1$, $R^3$, $A^1$ and n are the combinations shown in [Table 1] to [Table 16].

In the formula (F-2), compounds wherein $R^6$ is a pentafluoroethyl group, $R^8$ is a chlorine atom, and $R^1$, $R^3$, $A^1$ and n are the combinations shown in [Table 1] to [Table 16].

In the formula (F-2), compounds wherein $R^6$ is a pentafluoroethyl group, $R^8$ is a bromine atom, and $R^1$, $R^3$, $A^1$ and n are the combinations shown in [Table 1] to [Table 16].

In the formula (F-2), compounds wherein $R^6$ is a pentafluoroethyl group, $R^8$ is a methyl group, and $R^1$, $R^3$, $A^1$ and n are the combinations shown in [Table 1] to [Table 16].

In the formula (F-2), compounds wherein $R^6$ is a heptafluoroisopropyl group, $R^8$ is a hydrogen atom, and $R^1$, $R^3$, $A^1$ and n are the combinations shown in [Table 1] to [Table 16].
In the formula (F-2), compounds wherein $R^6$ is a heptafluoroisopropyl group, $R^8$ is a chlorine atom, and $R^1$, $R^3$, $A^1$ and n are the combinations shown in [Table 1] to [Table 16].
In the formula (F-2), compounds wherein $R^6$ is a heptafluoroisopropyl group, $R^8$ is a bromine atom, and $R^1$, $R^3$, $A^1$ and n are the combinations shown in [Table 1] to [Table 16].
In the formula (F-2), compounds wherein $R^6$ is a heptafluoroisopropyl group, $R^8$ is a methyl group, and $R^1$, $R^3$, $A^1$ and n are the combinations shown in [Table 1] to [Table 16].
In the formula (F-2), compounds wherein $R^6$ is a trifluoromethoxy group, $R^8$ is a hydrogen atom, and $R^1$, $R^3$, $A^1$ and n are the combinations shown in [Table 1] to [Table 16].
In the formula (F-2), compounds wherein $R^6$ is a trifluoromethoxy group, $R^8$ is a chlorine atom, and $R^1$, $R^3$, $A^1$ and n are the combinations shown in [Table 1] to [Table 16].
In the formula (F-2), compounds wherein $R^6$ is a trifluoromethoxy group, $R^8$ is a bromine atom, and $R^1$, $R^3$, $A^1$ and n are the combinations shown in [Table 1] to [Table 16].
In the formula (F-2), compounds wherein $R^6$ is a trifluoromethoxy group, $R^8$ is a methyl group, and $R^1$, $R^3$, $A^1$ and n are the combinations shown in [Table 1] to [Table 16].
In the formula (F-2), compounds wherein $R^6$ is a trifluoromethylsulfanyl group, $R^8$ is a hydrogen atom, and $R^1$, $R^3$, $A^1$ and n are the combinations shown in [Table 1] to [Table 16].
In the formula (F-2), compounds wherein $R^6$ is a trifluoromethylsulfanyl group, $R^8$ is a chlorine atom, and $R^1$, $R^3$, $A^1$ and n are the combinations shown in [Table 1] to [Table 16].
In the formula (F-2), compounds wherein $R^6$ is a trifluoromethylsulfanyl group, $R^8$ is a bromine atom, and $R^1$, $R^3$, $A^1$ and n are the combinations shown in [Table 1] to [Table 16].
In the formula (F-2), compounds wherein $R^6$ is a trifluoromethylsulfanyl group, $R^8$ is a methyl group, and $R^1$, $R^3$, $A^1$ and n are the combinations shown in [Table 1] to [Table 16].
In the formula (F-2), compounds wherein $R^6$ is a trifluoromethylsulfinyl group, $R^8$ is a hydrogen atom, and $R^1$, $R^3$, $A^1$ and n are the combinations shown in [Table 1] to [Table 16].
In the formula (F-2), compounds wherein $R^6$ is a trifluoromethylsulfinyl group, $R^8$ is a chlorine atom, and $R^1$, $R^3$, $A^1$ and n are the combinations shown in [Table 1] to [Table 16].
In the formula (F-2), compounds wherein $R^6$ is a trifluoromethylsulfinyl group, $R^8$ is a bromine atom, and $R^1$, $R^3$, $A^1$ and n are the combinations shown in [Table 1] to [Table 16].
In the formula (F-2), compounds wherein $R^6$ is a trifluoromethylsulfinyl group, $R^8$ is a methyl group, and R, $R^3$, $A^1$ and n are the combinations shown in [Table 1] to [Table 16].
In the formula (F-2), compounds wherein $R^6$ is a trifluoromethylsulfonyl group, $R^8$ is a hydrogen atom, and $R^1$, $R^3$, $A^1$ and n are the combinations shown in [Table 1] to [Table 16].
In the formula (F-2), compounds wherein $R^6$ is a trifluoromethylsulfonyl group, $R^8$ is a chlorine atom, and $R^1$, $R^3$, $A^1$ and n are the combinations shown in [Table 1] to [Table 16].
In the formula (F-2), compounds wherein $R^6$ is a trifluoromethylsulfonyl group, $R^8$ is a bromine atom, and $R^1$, $R^3$, $A^1$ and n are the combinations shown in [Table 1] to [Table 16].
In the formula (F-2), compounds wherein $R^6$ is a trifluoromethylsulfonyl group, $R^8$ is a methyl group, and $R^1$, $R^3$, $A^1$ and n are the combinations shown in [Table 1] to [Table 16].

Examples of the pest on which the compound of the present invention has an effect include arthropod pests such as pest insects and pest mites and nematoda. Specifically, examples of the pests include those shown below.

Hemiptera: Delphacidae such as *Laodelphax striatellus*, *Nilaparvata lugens*, and *Sogatella furcifera*, Deltocephalidae such as *Nephotettix cincticeps*, *Nephotettix virescens*, and *Empoasca onukii*, Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*, Pentatomidae such as *Nezara antennata*, *Riptortus clavetus*, *Leptocorisa chinensis*, *Eysarcoris parvus*, and *Halyomorpha mista*, Aleyrodidae such as *Trialeurodes vaporariorum*, *Bemisia tabaci*, *Dialeurodes citri*, and *Aleurocanthus spiniferus*, Coccidae such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*, Tingidae, Cimicidae such as *Cimex lectularius*, and Psyllidae.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., and *Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes honmai.*, *Homona magnanima*, *Archips fuscocupreanus*, and *Cydia pomonella*, Gracillariidae such as *Caloptilia theivora*, and *Phyllonorycter ringoneella*, Carposinidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thripidae such as *Frankliniella occidentalis*, *Thrips parmi*, *Scirtothrips dorsalis*, *Thrips tabaci*, and *Frankliniella intonsa*.

Diptera: Culex such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae*, *Hydrellia griseola*, *Liriomyza sativae*, *Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Sciaridae, Simuliidae, Tabanidae such as *Tabanus trigonus*, Stomoxys, and Stomoxyidae.

Coleoptera: Corn rootworm such as *Diabrotica virgifera virgifera* and *Diabrotica undecimpunctata howardi*, Scarabaeidae such as *Anomala cuprea*, *Anomala rufocuprea*, and *Popillia japonica*, Curculionidae such as *Sitophilus zeamais*, *Lissorhoptrus oryzophilus*, *Callosobruchuys chienensis*, *Echinocnemus squameus*, *Anthonomus grandis*, and *Sphenophorus venatus*, Tenebrionidae such as *Tenebrio molitor* and *Tribolium castaneum*, Chrysomelidae such as *Oulema oryzae*, *Aulacophora femoralis*, *Phyllotreta striolata*, and *Leptinotarsa decemlineata*, Dermestidae such as *Anthrenus verbasci* and *Dermestes maculates*, Anobiidae such as *Lasioderma serricorne*, Epilachna such as *Epilachna vigintioctopunctata*, Lyctidae such as *Lyctus brunneus* and *Tomicus piniperda*, Bostrychidae, Ptinidae, Cerambycidae such as *Anoplophora malasiaca*, *Agriotes* spp., and *Paederus fuscipes*.

Orthoptera: *Locusta migratoria*, *Gryllotalpa africana*, *Oxya yezoensis*, *Oxya japonica*, and Grylloidea.

Siphonaptera: *Ctenocephalides felis, Ctenocephalides canis, Pulex irritans, Xenopsylla cheopis* and the like.

Anoplura: *Pediculus humanus corporis, Pediculus humanus humanus, Phthirus pubis, Haematopinus eurysternus, Dalmalinia ovis, Haematopinus suis, Linognathus setosus* and the like.

Mallophaga: *Dalmalinia ovis, Dalmalinia bovis, Menopon gallinae, Trichodectes canis, Felicola subrostrata* and the like.

Hymenoptera: Formicidae such as *Monomorium pharaosis, Formica fusca japonica, Ochetellus glaber, Pristomyrmex pungens, Pheidole noda, Acromyrmex* spp., *Solenopsis* spp., and *Linepithema humile*, Vespidae, Bethylidae, and Tenthredinidae such as *Athalia rosae* and *Athalia japonica*.

Nematoda: *Aphelenchoides besseyi, Nothotylenchus acris, Meloidogyne incognita, Meloidogyne hapla, Meloidogyne javanica, Heterodera glycines, Globodera rostochiensis, Pratylenchus coffeae, Pratylenchus neglectus*.

Blattodea: *Blattella germanica, Periplaneta fuliginosa, Periplaneta americana, Periplaneta brunnea, Blatta orientalis*.

Isoptera: *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes* sp., *Nasutitermes takasagoensis, Pericapritermes nitobei, Sinocapritermes mushae* and the like.

Acarina: Tetranychidae such as *Tetranychus urticae, Tetranychus kanzawai, Panonychus citri, Panonychus ulmi*, and *Oligonychus* spp., Eriophyidae such as *Aculops pelekassi, Phyllocoptruta citri, Aculops lycopersici, Calacarus carinatus, Acaphylla theavagrans, Eriophyes chibaensis*, and *Aculus schlechtendali*, Tarsonemidae such as *Polyphagotarsonemus latus*, Tenuipalpidae such as *Brevipalpus phoenicis*, Tuckerellidae, Ixodidae such as *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus*, and *Rhipicephalus sanguineus*, Acaridae such as *Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus, Cheyletus malaccensis, Cheyletus moorei*, and *Cheyletiella yasguri*, Sarcoptidae such as *Octodectes cynotis* and *Sacroptes scabiei*, Demodicidae such as *Demodex canis*, Listrophoridae, Oribatei, Dermanyssidae such as *Ornithonyssus bacoti, Ornithonyssus sylvairum*, and *Dermanyssus gallinae*, Trombiculidae such as *Leptotrombidium akamushi*, and Arachnida such as *Chiracanthium japonicum* and *Latrodectus hasseltii*, and the like.

Chilopoda: *Thereuonema hilgendorfi, Scolopendra subspinipes* and the like.

Diplopoda: *Oxidus gracilis, Nedyopus tambanus* and the like.

Isopoda: *Armadillidium vulgare* and the like.

Gastropoda: *Limax marginatus, Limax flavus* and the like.

The pest control agent of the present invention contains the compound of the present invention and an inert carrier. The pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powders, flowables, microcapsule formulations, aerosols, fumigants, poisonous baits, resin formulations, shampoo agent, paste formulation, foam agent, carbon dioxide preparation, tablet, and the like. These formulations may be processed into mosquito repellent coil, electric mosquito repellent mat, mosquito repellent liquid formulation, smoking agent, fumigant, sheet formulation, spot-on agent, or oral treatment agent, and used.

The pest control agent of the present invention usually contains the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), chemical fertilizers (ammonium sulfate, ammonium phosphate, ammonium nitrate, urea, ammonium chloride, etc.) and the like, and synthetic resins (polyester resins such as polypropylene, polyacrylonitrile, polymethylmethacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxiliaries for formulation include fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as ester phthalates (dimethyl phthalate, dioctyl phthalate, etc.), ester adipates or stearic acid may be added to these base materials as necessary. The resin formulation is obtained by kneading a compound into the base material using an ordinary kneading apparatus, then molding it by injection molding, extrusion molding, press molding or the like, and can be processed into a plate, film, taped, reticular or string resin formulation by further undergoing molding or cutting step as necessary. These resin formulations are processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing erroneous eating from children and pets such as red pepper powder, a pest attractant such as cheese flavor, onion flavor and peanut oil or the like is added as necessary.

The method for controlling pests of the present invention is carried out by applying an effective amount of the compound of the present invention to a pest directly and/or a place where a pest inhabits (plants, soil, in-house, animal body, etc.). In the method for controlling pests of the present invention, the compound is usually used in the form of the pest control agent of the present invention.

When the pest control agent of the present invention is used in pest controlling in the agricultural field, the application amount is usually 1 to 10000 g in terms of the amount of the compound of the present invention per 10000 $m^2$. When the pest control agent of the present invention is formulated into an emulsifiable concentrate, a wettable powder, a flowable or the like, the pest control agent is usually diluted with water so as to have a concentration of the active ingredient of 0.01 to 10000 ppm and applied, and dust formulations, granules and the like are usually applied as they are.

These formulations and formulation solutions diluted with water may be directly treated by being sprayed on a pest or a plant such as crops which should be protected from pests, and also may be treated on a soil in order to control a pest that inhabits in the soil of cultivated land.

Also, the resin formulation processed into a sheet or string can be also treated by a method such as winding it around crops, spreading it in the vicinity of crops, or spreading it to the soil around crop roots.

When the pest control agent of the present invention is used in controlling the pest that inhabits in the house, the application amount is usually 0.01 to 1000 mg in an amount of the compound of the present invention per 1 $m^2$ of an area to be treated, in the case of using it on a planar area, and is usually 0.01 to 500 mg in an amount of the compound of the present invention per 1 $m^3$ of a space to be treated, in the case of using it in a space. When the pest control agent of the present invention is formulated into an emulsifiable concentrate, a wettable powder, a flowable or the like, the pest control agent is usually diluted with water so as to have a concentration of the active ingredient of 0.1 to 10000 ppm and applied, and oil formulations, aerosols, fumigants, poisonous baits and the like are applied as they are.

When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc.), when systemic control is intended, and the formulation is used, for example, by way of spraying an oil solution or aqueous solution, pour-on or spot-on treatment, washing an animal with a shampoo formulation, or putting a collar or ear tag made of a resin formulation to an animal, when non-systemic control is intended. The amount of the compound of the present invention when administered to an animal body is usually in the range from 0.1 to 1000 mg per 1 kg of the weight of an animal.

The pest control agent of the present invention can be used in the farmland where the following "crops" are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.

Trees other than fruit trees: tea, mulberry, flowering trees and shrubs (*azalea, camellia, hydrangea, sasanqua, Illicium religiosum*, cherry tree, tulip tree, crape myrtle, fragrant olive, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horsechestnut, etc.), sweet viburnum, *Podocarpus macrophyllus*, Japanese cedar, Japanese cypress, croton, spindle tree, Chainese howthorn, etc.

Lawn: *zoysia* (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.

Others: flowers (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, cymbidium, begonia, etc.), bio-fuel plants (Jatropha, curcas, safflower, Camelina alyssum, switchgrass, miscanthus, reed canary grass, Arundo donax, kenaf, cassava, willow, algae, etc.), foliage plants, etc.

The "crops" also include genetically modified crops.

The pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, plant growth regulator, herbicide and synergist are shown below.

Active Ingredients of Insecticide
(1) Organic Phosphorus Compounds
acephate, Aluminium phosphide, butathiofos, cadusafos, chlorethoxyfos, chlorfenvinphos, chlorpyrifos, chlorpyrifos-methyl, cyanophos: CYAP, diazinon, DCIP(dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.
(2) Carbamate Compounds
alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.
(3) Pyrethroid Compounds
acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS; 1RS,3SR)-2,2-dimethyl-3-prop-1-enylcyclopropanecarboxylate, 2,3,5,6-tetrafluoro-4-methylbenzyl (EZ)-(1RS,3RS; 1RS,3SR)-2,2-dimethyl-3-prop-1-enylcyclopropanecarboxylate, and 2,3,5,6-tetrafluoro-4-(methoxymethyl)benzyl(1RS,3RS; 1RS,3SR)-2,2-dimethyl-3-(2-methyl-1-propenyl)cyclopropanecarboxylate, 2,3,5,6-tetrafluoro-4-(methoxymethyl)benzyl (EZ)-(1RS,3RS; 1RS,3SR)-2,2-dimethyl-3-(2-cyano-1-propenyl)cyclopropanecarboxylate.
(4) Nereistoxin Compounds
cartap, bensultap, thiocyclam, monosultap, and bisultap.
(5) Neonicotinoid Compounds
imidacloprid, nitenpyram, acetamiprid, thiamethoxam, thiacloprid, dinotefuran, and clothianidin.
(6) Benzoyl Urea Compounds
chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.
(7) Phenylpyrazole-Based Compounds
acetoprole, ethiprole, fipronil, vaniliprole, pyriprole, and pyrafluprole.
(8) Bt Toxins
Living spores derived from *Bacillus thuringiensis* and produced crystalline toxins and mixtures thereof.
(9) Hydrazine Compounds chromafenozide, halofenozide, methoxyfenozide, and tebufenozide.
(10) Organic Chlorine Compounds
aldrin, dieldrin, dienochlor, endosulfan, and methoxychlor.
(11) Other Active Ingredients of Insecticide
machine oil, nicotine-sulfate; avermectin-B, bromopropylate, buprofezin, chlorphenapyr, cyantraniliprole, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, cyantraniliprole, compounds represented by the following formula (K)

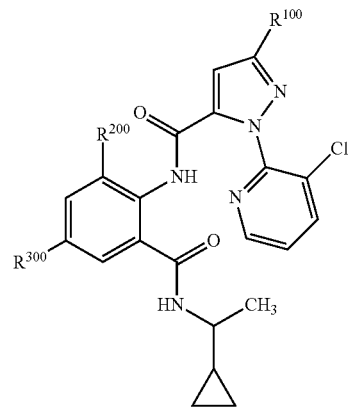

wherein
$R^{100}$ represents chlorine, bromine or a trifluoromethyl group,
$R^{200}$ represents chlorine, bromine or a methyl group, and
$R^{300}$ represents chlorine, bromine or a cyano group, and compounds represented by the following formula (L)

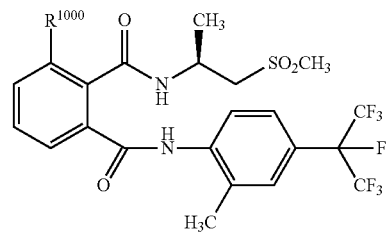

wherein
$R^{1000}$ represents chlorine, bromine or iodine.
Active Ingredients of Miticide
acequinocyl, amitraz, benzoximate, bifenaate, bromopropylate, chinomethionat, chlorobenzilate, CPCBS (chlorfenson), clofentezine, cyflumetofen, kelthane (dicofol, etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.
Active Ingredients of Nematicide
DCIP, fosthiazate, levamisol, methyisothiocyanate, morantel tartarate, and imicyafos.
Active Ingredients of Fungicide
Azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol; Cyclic amine fungicidal compounds such as fenpropimorph, tridemorph, and fenpropidin; Benzimidazole fungicidal compounds such as carbendezim, benomyl, thiabendazole, and thiophanate-methyl; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.

Active Ingredients of Herbicide (1) Phenoxy Fatty Acid Herbicidal Compounds
2,4-PA, MCP, MCPB, phenothiol, mecoprop, fluroxypyr, triclopyr, clomeprop, and naproanilide.

(2) Benzoate Herbicidal Compounds
2,3,6-TBA, dicamba, clopyralid, picloram, aminopyralid, quinclorac, and quinmerac.

(3) Urea Herbicidal Compounds
diuron, linuron, chlortoluron, isoproturon, fluometuron, isouron, tebuthiuron, methabenzthiazuron, cumyluron, daimuron, and methyl-daimuron.

(4) Triazine Herbicidal Compounds
atrazine, ametoryn, cyanazine, simazine, propazine, simetryn, dimethametryn, prometryn, metribuzin, triaziflam, and indaziflam.

(5) Bipyridinium Herbicidal Compounds
paraquat, and diquat.

(6) Hydroxybenzonitrile Herbicidal Compounds
bromoxynil, and ioxynil.

(7) Dinitroaniline Herbicidal Compounds
pendimethalin, prodiamine, and trifluralin.

(8) Organophosphorus Herbicidal Compounds
amiprofos-methyl, butamifos, bensulide, piperophos, anilofos, glyphosate, glufosinate, glufosinate-P, and bialaphos.

(9) Carbamate Herbicidal Compounds
di-allate, tri-allate, EPTC, butylate, benthiocarb, esprocarb, molinate, dimepiperate, swep, chlorpropham, phenmedipham, phenisopham, pyributicarb, and asulam.

(10) Acid Amide Herbicidal Compounds
propanil, propyzamide, bromobutide, and etobenzanid.

(11) Chloroacetanilide Herbicidal Compounds
acetochlor, alachlor, butachlor, dimethenamid, propachlor, metazachlor, metolachlor, pretilachlor, thenylchlor, and pethoxamid.

(12) Diphenyl Ether Herbicidal Compounds
acifluorfen-sodium, bifenox, oxyfluorfen, lactofen, fomesafen, chlomethoxynil, and aclonifen.

(13) Cyclic Imide Herbicidal Compounds
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Herbicidal Compounds
benzofenap, pyrazolate, pyrazoxyfen, topramezone, and pyrasulfotole.

(15) Triketone Herbicidal Compounds
isoxaflutole, benzobicyclon, sulcotrione, mesotrione, tembotrione, and tefuryltrione.

(16) Aryloxyphenoxypropionate Herbicidal Compounds
clodinafop-propargyl, cyhalofop-butyl, diclofop-methyl, fenoxaprop-ethyl, fluazifop-butyl, haloxyfop-methyl, and quizalofop-ethyl, metamifop.

(17) Trione Oxime Herbicidal Compounds
alloxydim-sodium, sethoxydim, butroxydim, clethodim, cloproxydim, cycloxydim, tepraloxydim, traikoxydim, and profoxydim.

(18) Sulfonyl Urea Herbicidal Compounds
chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.

(19) Imidazolinone Herbicidal Compounds
imazamethabenz-methyl, imazamethapyr, imazamox, imazapyr, imazaquin, and imazethapyr.

(20) Sulfonamide Herbicidal Compounds
flumetsulam, metosulam, diclosulam, florasulam, cloransulam-methyl, penoxsulam, and pyroxsulam.

(21) Pyrimidinyloxybenzoate Herbicidal Compounds
pyrithiobac-sodium, bispyribac-sodium, pyriminobac-methyl, pyribenzoxim, pyriftalid, and pyrimisulfan.

(22) Other Herbicidal Compounds
bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active ingredients of Plant Growth Regulator hymexazol, paclobutrazol, uniconazole-P, inabenfide, prohexadione-calcium, aviglycine, naphthalene acetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chloride and 4-CPA (4-chlorophenoxyacetic acid).

Active ingredients of Synergist
piperonyl butoxide, sesamex, sulfoxide, N-(2-ethylhexyl)-8, 9,10-trinorborn-5-ene-2,3-dicarboximide (MGK 264), N-declyimidazole, WARF-antiresistant, TBPT, TPP, IBP, PSCP, $CH_3I$, t-phenylbutenone, diethylmaleate, DMC, FDMC, ETP, and ETN.

EXAMPLES

Hereinbelow, the present invention will be further described in detail by production examples, reference examples, formulation examples, test examples, and the like. However, the present invention is not limited only to these examples.

First, the production examples for the production of the compounds of the present invention will be shown.

Production Example 1 (1)

A mixture of 500 mg of 2-nitro-4-trifluoromethylbenzaldehyde, 349 mg of 2-(ethylsulfanyl)aniline and 4 ml of toluene was refluxed for 4 hours and then concentrated under reduced pressure. The resulting residue was washed with t-butyl methyl ether to obtain 777 mg of (2-ethylsulfanylphenyl) (2-nitro-4-trifluoromethylbenzylidene)amine.

(2-Ethylsulfanylphenyl) (2-nitro-4-trifluoromethylbenzylidene)amine

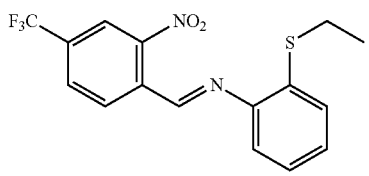 [SMILES: CCSc1ccccc1/N=C/c1ccc(C(F)(F)F)cc1[N+](=O)[O-]]

¹H-NMR (CDCl₃) δ: 8.93 (1H, s), 8.59 (1H, d), 8.36 (1H, s), 8.00 (1H, d), 7.33-7.25 (2H, m), 7.22 (1H, td), 7.11 (1H, d), 2.99 (2H, q), 1.40 (3H, t).

Production Example 1 (2)

A mixture of 777 mg of (2-ethylsulfanylphenyl) (2-nitro-4-trifluoromethylbenzylidene)amine and 3 ml of triethyl phosphite was stirred at 100° C. for 15 minutes and then concentrated under reduced pressure. The resulting residue was applied to a silica gel column chromatography to obtain 558 mg of 2-(2-ethylsulfanylphenyl)-6-trifluoromethyl-2H-indazole (hereinafter, referred to as Compound of Present Invention 1).

Compound of Present Invention 1

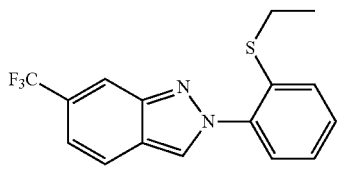 [SMILES: CCSc1ccccc1-n1cc2ccc(C(F)(F)F)cc2n1]

¹H-NMR (CDCl₃) δ: 8.34 (1H, s), 8.15 (1H, s), 7.87 (1H, d), 7.56-7.44 (3H, m), 7.36 (1H, td), 7.31 (1H, dd), 2.80 (2H, q), 1.22 (3H, t).

Production Example 2

607 mg of 3-chloroperoxybenzoic acid (purity of 65% or more) was added to a mixture of 407 mg of 2-(2-ethylsulfanylphenyl)-6-trifluoromethyl-2H-indazole and 5 ml of chloroform under ice cooling, and the mixture was stirred at room temperature for 4 hours. A 10% aqueous sodium thiosulfate solution was poured to the reaction mixture, and the mixture was extracted with chloroform. The organic layer was washed with a saturated aqueous sodium bicarbonate solution and dried over anhydrous magnesium sulfate, then concentrated under reduced pressure to obtain 452 mg of 2-(2-ethylsulfonylphenyl)-6-trifluoromethyl-2H-indazole (hereinafter, referred to as Compound of Present Invention 2)

Compound of Present Invention 2

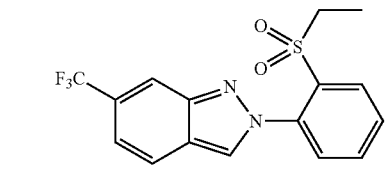 [SMILES: CCS(=O)(=O)c1ccccc1-n1cc2ccc(C(F)(F)F)cc2n1]

¹H-NMR (CDCl₃) δ: 8.42 (1H, s), 8.26 (1H, dd), 8.08 (1H, s), 7.89 (1H, dd), 7.86-7.75 (2H, m), 7.58 (1H, dd), 7.34 (1H, dd), 3.20 (2H, q), 1.23 (3H, t).

Production Example 3

A mixture of 226 mg of 2-(2-ethylsulfonylphenyl)-6-trifluoromethyl-2H-indazole, 86 mg of N-chlorosuccinimide and 2 ml of DMF was stirred at room temperature for 10 hours. A 10% aqueous sodium thiosulfate solution was poured to the reaction mixture, and the mixture was extracted with t-butyl methyl ether. The organic layer was washed with water and dried over anhydrous magnesium sulfate, then concentrated under reduced pressure. The resulting residue was washed with n-hexane to obtain 250 mg of 3-chloro-2-(2-ethylsulfonylphenyl)-6-trifluoromethyl-2H-indazole (hereinafter, referred to as Compound of Present Invention 3).

Compound of Present Invention 3

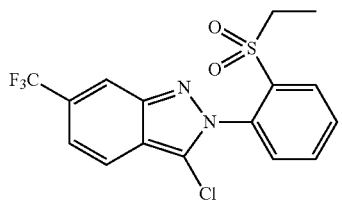 [SMILES: CCS(=O)(=O)c1ccccc1-n1nc2cc(C(F)(F)F)ccc2c1Cl]

¹H-NMR (CDCl₃) δ: 8.25 (1H, dd), 8.00 (1H, s), 7.90-7.81 (2H, m), 7.79 (1H, dd), 7.53 (1H, dd), 7.36 (1H, dd), 3.53-3.32 (2H, m), 1.26 (3H, t).

Production Example 4 (1)

A mixture of 14.1 g of 1-bromo-2-ethylsulfanylbenzene and 65 mL of THF was cooled to −70° C., and 44.7 mL of n-butyllithium (1.63 M hexane solvent) was added to the mixture at a rate so as to maintain an internal temperature of −60° C. or lower, and the mixture was stirred at −50° C. for 30 minutes. A mixture of 14 g of isopropoxyboronic acid pinacol ester and 5 mL of THF was added to the mixture at a rate so as to maintain an internal temperature of −60° C. or lower, and the mixture was heated to room temperature. Water was poured to the reaction mixture, and the mixture was extracted with ethyl acetate. The organic layer was washed with water, then dried over anhydrous sodium sulfate and concentrated under reduced pressure. The resulting residue was applied to a silica gel column chromatography to obtain 7.9 g of 2-ethylsulfanylphenylboronic acid pinacol ester.

2-Ethylsulfanylphenylboronic acid pinacol ester

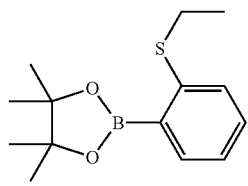 [SMILES: CCSc1ccccc1B1OC(C)(C)C(C)(C)O1]

$^1$H-NMR (CDCl$_3$) δ: 7.63 (1H, dd), 7.33 (1H, td), 7.28-7.25 (1H, m), 7.12 (1H, td), 2.93 (2H, q), 1.38 (12H, s), 1.33 (3H, t).

Production Example 4 (2)

A mixture of 3.0 g of 2-amino-5-trifluoromethylpyridine and 7 ml of bromoethylacetate was stirred at 80° C. for 1 hour, and concentrated under reduced pressure. The resulting residue was suspended in a mixed solvent of acetonitrile and t-butyl methyl ether, and filtered. The resulting solid was washed with t-butyl methyl ether to obtain 2.46 g of (2-imino-5-trifluoromethyl-2H-pyridin-1-yl)ethyl acetate hydrobromide.

(2-Imino-5-trifluoromethyl-2H-pyridin-1-yl)ethyl acetate hydrobromide

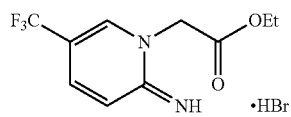 [SMILES: CCOC(=O)Cn1cc(C(F)(F)F)ccc1=N ; Br]

$^1$H-NMR (DMSO-D$_6$) δ: 9.64 (1H, brs), 9.13 (1H, brs), 8.75 (1H, s), 8.21 (1H, dd), 7.27 (1H, d), 5.20 (2H, s), 4.22 (2H, q), 1.26 (3H, t).

Production Example 4 (3)

A mixture of 1.63 g of (2-imino-5-trifluoromethyl-2H-pyridin-1-yl)ethyl acetate hydrobromide, 2.84 g of phosphorus oxybromide and 2 ml of propionitrile was stirred at 100° C. for 2.5 hours. The cooled reaction mixture was neutralized in a saturated aqueous sodium bicarbonate solution and a 5 M aqueous sodium hydroxide solution, and the precipitated solid was filtered. The resulting solid was washed with water and n-hexane to obtain 808 mg of 2-bromo-6-trifluoromethyl-imidazo[1,2-a]pyridine.

2-Bromo-6-trifluoromethyl-imidazo[1,2-a]pyridine

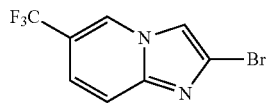 [SMILES: FC(F)(F)c1ccc2nc(Br)cn2c1]

$^1$H-NMR (CDCl$_3$) δ: 8.45 (1H, s), 7.77-7.59 (2H, m), 7.36 (1H, d).

Production Example 4 (4)

A mixture of 526 mg of 2-bromo-6-trifluoromethyl-imidazo[1,2-a]pyridine, 576 mg of 2-ethylsulfanylphenylboronic acid pinacol ester, 50 mg of tris(dibenzylideneacetone)dipalladium(0), 201 mg of tricyclohexylphosphine (18% toluene solution), 1.26 g of tripotassium phosphate, 4.5 ml of 1,4-dioxane and 1.5 ml of water was stirred at 100° C. for 2.5 hours. Ethyl acetate and water were poured to the cooled reaction mixture, and the mixture was filtered. The aqueous layer of the filtrate was extracted with ethyl acetate, then combined with the organic layer of the filtrate, and the mixture was washed with water and dried over anhydrous magnesium sulfate. The mixture was concentrated under reduced pressure, and the resulting residue was applied to a silica gel column chromatography to obtain 570 mg of 2-(2-ethylsulfanylphenyl)-6-trifluoromethyl-imidazo[1,2-a]pyridine (hereinafter, referred to as Compound of Present Invention 4).

Compound of Present Invention 4

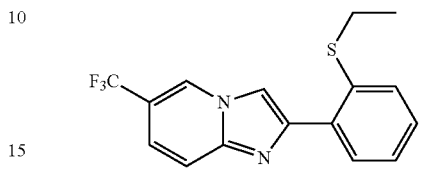

$^1$H-NMR (CDCl$_3$) δ: 8.55 (1H, s), 8.32 (1H, s), 8.03 (1H, dd), 7.74 (1H, d), 7.42 (1H, dd), 7.36-7.30 (3H, m), 2.96 (2H, q), 1.31 (3H, t).

Production Example 5

552 mg of 3-chloroperoxybenzoic acid (purity of 65% or more) was added to a mixture of 370 mg of 2-(2-ethylsulfanylphenyl)-6-trifluoromethyl-imidazo[1,2-a]pyridine and 5 ml of chloroform under ice cooling, and the mixture was stirred at room temperature for 2 hours. A 10% aqueous sodium thiosulfate solution was poured to the reaction mixture, and the mixture was extracted with chloroform. The organic layer was washed with a saturated aqueous sodium bicarbonate solution and dried over anhydrous magnesium sulfate, then concentrated under reduced pressure. The resulting residue was applied to a silica gel column chromatography to obtain 260 mg of 2-(2-ethylsulfonylphenyl)-6-trifluoromethyl-imidazo[1,2-a]pyridine (hereinafter, referred to as Compound of Present Invention 5).

Compound of Present Invention 5

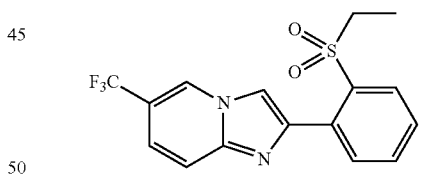

$^1$H-NMR (CDCl$_3$) δ: 8.57 (1H, s), 8.23 (1H, d), 8.20 (1H, s), 7.80 (1H, d), 7.75-7.69 (2H, m), 7.61 (1H, t), 7.38 (1H, d), 3.23 (2H, q), 1.17 (3H, t).

Production Example 6 (1)

A mixture of 1.5 g of 4-bromo-3-fluorobenzotrifluoride, 0.46 ml of ethanethiol, 851 mg of potassium carbonate and 2 ml of DMF was stirred at 75° C. for 2.5 hours. Water was poured to the cooled reaction mixture, and the mixture was extracted with t-butyl methyl ether. The organic layer was washed with water, dried over anhydrous magnesium sulfate and then concentrated under reduced pressure. The resulting residue was applied to a silica gel column chromatography to obtain 1.15 g of 4-bromo-3-ethylsulfanylbenzotrifluoride.

4-Bromo-3-ethylsulfanylbenzotrifluoride

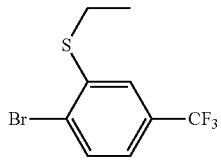

$^1$H-NMR (CDCl$_3$) δ: 7.65 (1H, d), 7.38 (1H, d), 7.26-7.22 (1H, m), 3.01 (2H, q), 1.41 (3H, t).

Production Example 6 (2)

A mixture of 500 mg of 4-bromo-3-ethylsulfanylbenzotrifluoride, 494 mg of bis(pinacolato)diboron, 49 mg of tris(dibenzylideneacetone) dipalladium(0), 198 mg of tricyclohexylphosphine (18% toluene solution), 502 mg of potassium acetate and 2 ml of 1,4-dioxane was stirred at 80° C. for 3 hours. Ethyl acetate and water were poured to the cooled reaction mixture, and the mixture was filtered. The aqueous layer of the filtrate was extracted with ethyl acetate, then combined with the organic layer of the filtrate, and the mixture was washed with water and dried over anhydrous magnesium sulfate. The mixture was concentrated under reduced pressure, and the resulting residue was applied to a silica gel column chromatography to obtain 322 mg of 2-ethylsulfanyl-4-trifluoromethylphenylboronic acid pinacol ester.

2-Ethylsulfanyl-4-trifluoromethylphenylboronic acid pinacol ester

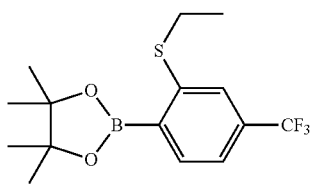 [SMILES: CCSc1cc(C(F)(F)F)ccc1B1OC(C)(C)C(C)(C)O1]

$^1$H-NMR (CDCl$_3$) δ: 7.73 (1H, d), 7.44 (1H, s), 7.34 (1H, d), 2.97 (2H, q), 1.41-1.31 (15H, m).

Production Example 6 (3)

A mixture of 200 mg of 2-bromo-6-trifluoromethyl-imidazo[1,2-a]pyridine, 332 mg of 2-ethylsulfanyl-4-trifluoromethylphenylboronic acid pinacol ester, 21 mg of tris(dibenzylideneacetone) dipalladium(0), 85 mg of tricyclohexylphosphine (18% toluene solution), 480 mg of tripotassium phosphate, 1.5 ml of 1,4-dioxane and 0.5 ml of water was stirred at 100° C. for 4 hours. Water was poured to the cooled reaction mixture, and the mixture was extracted with ethyl acetate. The organic layer was washed with water, dried over anhydrous magnesium sulfate and then concentrated under reduced pressure. The resulting residue was applied to a silica gel column chromatography to obtain 236 mg of 2-(2-ethylsulfanyl-4-trifluoromethylphenyl)-6-trifluoromethyl-imidazo[1,2-a]pyridine (hereinafter, referred to as Compound of Present Invention 6).

Compound of Present Invention 6

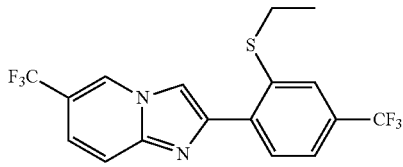 [SMILES: CCSc1cc(C(F)(F)F)ccc1-c1cn2cc(C(F)(F)F)ccc2n1]

$^1$H-NMR (CDCl$_3$) δ: 8.57 (1H, s), 8.39 (1H, s), 8.18 (1H, d), 7.76 (1H, d), 7.61 (1H, s), 7.52 (1H, dd), 7.36 (1H, dd), 3.02 (2H, q), 1.36 (3H, t).

Production Example 7

436 mg of 3-chloroperoxybenzoic acid (purity of 65% or more) was added to a mixture of 236 mg of 2-(2-ethylsulfanyl-4-trifluoromethylphenyl)-6-trifluoromethyl-imidazo[1,2-a]pyridine and 5 ml of chloroform under ice cooling, and the mixture was stirred at room temperature for 4 hours. A 10% aqueous sodium thiosulfate solution was poured to the reaction mixture, and the mixture was extracted with chloroform. The organic layer was washed with a saturated aqueous sodium bicarbonate solution and dried over anhydrous magnesium sulfate, then concentrated under reduced pressure. The resulting residue was applied to a silica gel column chromatography to obtain 122 mg of 2-(2-ethylsulfonyl-4-trifluoromethylphenyl)-6-trifluoromethyl-imidazo[1,2-a]pyridine (hereinafter, referred to as Compound of Present Invention 7).

Compound of Present Invention 7

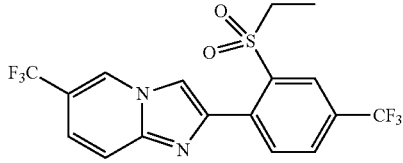 [SMILES: CCS(=O)(=O)c1cc(C(F)(F)F)ccc1-c1cn2cc(C(F)(F)F)ccc2n1]

$^1$H-NMR (CDCl$_3$) δ: 8.59 (1H, s), 8.51 (1H, s), 8.30 (1H, s), 8.01-7.94 (2H, m), 7.75 (1H, d), 7.43 (1H, dd), 3.27 (2H, q), 1.20 (3H, t).

Production Example 8 (1)

8.41 g of 3-chloroperoxybenzoic acid (purity of 65% or more) was added to a mixture of 3.0 g of 2'-ethylsulfanylacetophenone and 40 ml of chloroform under ice cooling, and the mixture was stirred at room temperature for 4 hours. A 10% aqueous sodium thiosulfate solution was poured to the reaction mixture, and the mixture was filtered. The filtrate was washed with a saturated aqueous sodium bicarbonate solution and dried over anhydrous magnesium sulfate, then concentrated under reduced pressure to obtain 3.5 g of 2'-ethylsulfonylacetophenone.

2'-Ethylsulfonylacetophenone

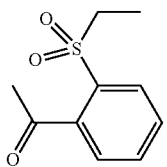

¹H-NMR (CDCl₃) δ: 8.01 (1H, dd), 7.69 (1H, td), 7.61 (1H, td), 7.44 (1H, dd), 3.37 (2H, q), 2.65 (3H, s), 1.30 (3H, t).

Production Example 8 (2)

A mixture of 1.0 g of 2'-ethylsulfonylacetophenone, 1.86 g of phenyltrimethylammonium tribromide and 10 ml of THF was stirred at room temperature for 3 hours. A 10% aqueous sodium thiosulfate solution was poured to the reaction mixture, and the mixture was extracted with t-butyl methyl ether. The organic layer was washed with water and dried over anhydrous magnesium sulfate, then concentrated under reduced pressure to obtain 1.37 g of 2-bromo-2'-ethylsulfonylacetophenone.

2-Bromo-2'-ethylsulfonylacetophenone

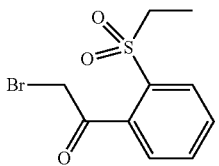

¹H-NMR (CDCl₃) δ: 8.01 (1H, dd), 7.74-7.65 (2H, m), 7.52 (1H, dd), 4.50 (2H, s), 3.25 (2H, q), 1.29 (3H, t).

Production Example 8 (3)

A mixture of 1.0 g of 2-bromo-2'-ethylsulfonylacetophenone, 334 mg of 2-amino-4-trifluoromethylpyridine and 4 ml of ethanol was refluxed for 1 hour and concentrated under reduced pressure. A mixture of the residue, 250 mg of sodium bicarbonate and 1.5 ml of DMF was stirred at 130° C. for 1 hour. Water was poured to the cooled reaction mixture, and the mixture was extracted with ethyl acetate. The organic layer was washed with water, dried over anhydrous magnesium sulfate, and then concentrated under reduced pressure. The resulting residue was applied to a silica gel column chromatography to obtain 190 mg of 2-(2-ethylsulfonylphenyl)-7-trifluoromethyl-imidazo[1,2-a]pyridine (hereinafter, referred to as Compound of Present Invention 8).

Compound of Present Invention 8

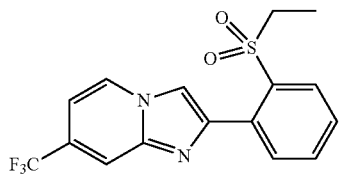 [SMILES: CCS(=O)(=O)c1ccccc1-c1cn2ccc(C(F)(F)F)cc2n1]

¹H-NMR (CDCl₃) δ: 8.29 (1H, d), 8.24 (1H, dd), 8.20 (1H, s), 7.94 (1H, d), 7.78 (1H, dd), 7.72 (1H, td), 7.62 (1H, td), 7.04 (1H, dd), 3.24 (2H, q), 1.17 (3H, t).

The compounds described in the production examples described above and the compounds produced by the production method according to the method described in the production examples described above are shown in the table.

Compounds Represented by Formula (1-1)

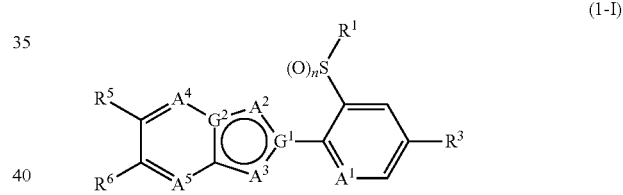

(1-I)

wherein $R^1$, $R^3$, $R^5$, $R^6$, $G^1$, $G^2$, $A^1$, $A^2$, $A^3$, $A^4$, $A^5$ and n represent the combinations in [Table 11] shown below.

TABLE 17

| Compound of Present Invention | $R^1$ | $R^3$ | $R^5$ | $R^6$ | $G^1$ | $G^2$ | $A^1$ | $A^2$ | $A^3$ | $A^4$ | $A^5$ | n |
|---|---|---|---|---|---|---|---|---|---|---|---|---|
| 1 | Et | H | CF₃ | H | N | C | CH | N | CH | CH | CH | 0 |
| 2 | Et | H | CF₃ | H | N | C | CH | N | CH | CH | CH | 2 |
| 3 | Et | H | CF₃ | H | N | C | CH | N | CCl | CH | CH | 2 |
| 4 | Et | H | CF₃ | H | C | N | CH | CH | N | CH | CH | 0 |
| 5 | Et | H | CF₃ | H | C | N | CH | CH | N | CH | CH | 2 |
| 6 | Et | CF₃ | CF₃ | H | C | N | CH | CH | N | CH | CH | 0 |
| 7 | Et | CF₃ | CF₃ | H | C | N | CH | CH | N | CH | CH | 2 |
| 8 | Et | H | H | CF₃ | C | N | CH | CH | N | CH | CH | 2 |
| 9 | Et | H | CF₃ | H | C | N | N | CH | N | CH | CH | 2 |
| 10 | Et | CF₃ | H | CF₃ | C | N | CH | CH | N | CH | CH | 2 |
| 11 | Et | H | H | CF₃ | C | N | N | CH | N | CH | CH | 2 |
| 12 | Et | H | I | H | C | N | CH | CH | N | CH | N | 2 |
| 13 | Et | H | CF₃ | H | C | N | CH | CH | N | N | CH | 2 |
| 14 | Et | H | CF₃CF₂ | H | C | N | CH | CH | N | CH | N | 2 |
| 15 | Et | H | CF₃ | H | C | N | CH | N | CH | CH | N | 2 |
| 16 | Et | CF₃ | CF₃ | H | C | N | N | CH | N | CH | CH | 2 |
| 17 | Et | H | CF₃ | H | N | C | N | N | CH | CH | CH | 2 |
| 18 | Et | CF₃ | CF₃ | H | N | C | N | N | CH | CH | CH | 2 |
| 19 | Et | H | CF₃CF₂ | H | C | N | CH | CH | N | CH | CH | 2 |

TABLE 17-continued

| Compound of Present Invention | R¹ | R³ | R⁵ | R⁶ | G¹ | G² | A¹ | A² | A³ | A⁴ | A⁵ | n |
|---|---|---|---|---|---|---|---|---|---|---|---|---|
| 20 | Et | CF₃ | CF₃ | H | N | C | CH | N | CH | CH | CH | 0 |
| 21 | Et | CF₃ | CF₃ | H | N | C | CH | N | CH | CH | CH | 2 |
| 22 | Et | CF₃ | CF₃ | H | N | C | CH | N | CCl | CH | CH | 2 |
| 23 | Et | CF₃ | CF₃ | H | N | C | CH | N | CBr | CH | CH | 2 |

(In [Table 17] shown above, Et represents an ethyl group.)

$^1$H-NMR data of the compounds of the present invention shown in [Table 17] are shown below.

Compound of Present Invention 12

$^1$H-NMR (CDCl$_3$) δ: 8.73 (1H, d), 8.65 (1H, d), 8.22 (1H, dd), 7.95 (1H, s), 7.78 (1H, dd), 7.71 (1H, td), 7.62 (1H, td), 3.38 (2H, q), 1.20 (3H, t).

Compound of Present Invention 14

$^1$H-NMR (CDCl$_3$) δ: 8.81 (1H, d), 8.71 (1H, d), 8.24 (1H, dd), 8.11 (1H, dd), 7.76-7.7 (2H, m), 7.662 (1H, td), 3.44 (2H, q), 1.23 (3H, t).

Compound of Present Invention 19

$^1$H-NMR (CDCl$_3$) δ: 8.53 (1H, s), 8.24 (1H, dd), 8.21 (1H, s), 7.79 (1H, d), 7.76-7.70 (2H, d), 7.62 (1H, td), 7.36 (1H, d), 3.25 (2H, q), 1.17 (3H, t).

Compound of Present Invention 20

$^1$H-NMR (CDCl$_3$) δ: 8.39 (1H, d), 8.15 (1H, s), 7.88 (1H, d), 7.71 (1H, d), 7.67 (1H, d), 7.60 (1H, dd), 7.33 (1H, dd), 2.89 (2H, q), 1.26 (3H, t).

Compound of Present Invention 21

$^1$H-NMR (CDCl$_3$) δ: 8.54 (1H, d), 8.46 (1H, s), 8.12-8.06 (2H, m), 7.90 (1H, d), 7.75 (1H, d), 7.36 (1H, dd), 3.28 (2H, q), 1.27 (3H, t).

Compound of Present Invention 22

$^1$H-NMR (CDCl$_3$) δ: 8.52 (1H, d), 8.13 (1H, dd), 8.01 (1H, d), 7.79 (1H, d), 7.70 (1H, d), 7.38 (1H, dd), 3.59-3.41 (2H, m), 1.30 (3H, t).

Compound of Present Invention 23

$^1$H-NMR (CDCl$_3$) δ: 8.52 (1H, d), 8.13 (1H, dd), 8.03 (1H, d), 7.75 (1H, d), 7.69 (1H, d), 7.39 (1H, dd), 3.64-3.37 (2H, m), 1.30 (3H, t).

Next, formulation examples of the compounds of the present invention are shown. The part means part by weight in the formulation examples.

Formulation Example 1

10 parts of any one of Compounds of Present Invention 1 to 23 is dissolved in a mixture of 35 parts of xylene and 35 parts of DMF, 14 parts of polyoxyethylenestyrylphenyl ether and 6 parts of calcium dodecylbenzenesulfonate are added thereto. The mixture is mixed to obtain each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of any one of Compounds of Present Invention 1 to 23 is further added thereto. The mixture is mixed to obtain each wettable powder.

Formulation Example 3

1 part of synthetic hydrous silicon oxide fine powder, 2 parts of calcium lignosulfonate, 30 parts of bentonite and 65 parts of kaolin clay are added to 2 parts of any one of Compounds of Present Invention 1 to 23 and mixed. Subsequently, an appropriate amount of water is added to this mixture, and the mixture is further stirred, granulated with a granulator, and forced-air dried to obtain each granule.

Formulation Example 4

1 part of any one of Compounds of Present Invention 1 to 23 is dissolved in an appropriate amount of acetone, and 5 parts of synthetic hydrous silicon oxide fine powder, 0.3 parts of PAP and 93.7 parts of Fubasami clay are added thereto. The mixture is sufficiently stirred and mixed to evaporate acetone to obtain each dust formulation.

Formulation Example 5

35 parts of a mixture of polyoxyethylene alkyl ether sulfate ammonium salt and white carbon (weight ratio 1:1), 10 parts of any one of Compounds of Present Invention 1 to 23 and 55 parts of water are mixed, and finely pulverized by wet grinding method to obtain each flowable.

Formulation Example 6

0.1 parts of any one of Compounds of Present Invention 1 to 23 is dissolved in 5 parts of xylene and 5 parts of trichloroethane, and the mixture is mixed with 89.9 parts of deodorized kerosene to obtain each oil solution.

Formulation Example 7

10 mg of any one of Compounds of Present Invention 1 to 23 is dissolved in 0.5 ml of acetone, and this solution is applied to 5 g of solid feed powder for animal (solid feed powder for breeding CE-2, product of CLEA Japan, Inc.), and the mixture is uniformly mixed. Subsequently, acetone is evaporated to dryness to obtain each poisonous bait.

Formulation Example 8

0.1 parts of any one of Compounds of Present Invention 1 to 23 and 49.9 parts of Neothiozol (Chuo Kasei Co., Ltd.) are filled into an aerosol container, and an aerosol valve is attached, then the container is filled with 25 parts of dimethyl ether and 25 parts of LPG and shaken, and an actuator is attached to obtain an oil-based aerosol.

Formulation Example 9

0.6 parts of any one of Compounds of Present Invention 1 to 23, 0.01 parts of BHT (2,6-di-tert-butyl-4-methylphenol), 5 parts of xylene, 3.39 parts of deodorized kerosene and 1 part of emulsifier {RHEODOL MO60 (product name of Kao Corporation)} are mixed and dissolved, and the resulting solution and 50 parts of distilled water are filled into an aerosol container. A valve is attached to the container, then 40 parts of a propellant (LPG) is filled under pressure through the valve to obtain an aqueous aerosol.

Formulation Example 10

0.1 g of any one of Compounds of Present Invention 1 to 23 is dissolved in 2 ml of propylene glycol, and a porous ceramic plate with a size of 4.0 cm×4.0 cm and 1.2 cm in thickness is impregnated with the resulting solution to obtain a heating type smoking agent.

Formulation Example 11

5 parts of any one of Compounds of Present Invention 1 to 23 and 95 parts of an ethylene-methyl methacrylate copolymer (a ratio of methyl methacrylate in the copolymer: 10% by weight, Acryft WD301, manufactured by Sumitomo Chemical Co., Ltd.) are melt-kneaded with a closed pressurizing kneader (manufactured by Moriyama Works), and the resulting kneaded matter is extruded from a extrusion molding machine through a molding die to obtain a rod-shaped molded body with a size of 15 cm in length and 3 mm in diameter.

Formulation Example 12

5 parts of any one of Compounds of Present Invention 1 to 23 and 95 parts of a soft vinyl chloride resin are melt-kneaded with a closed pressurizing kneader (manufactured by Moriyama Works), and the resulting kneaded matter is extruded from a extrusion molding machine through a molding die to obtain a rod-shaped molded body with a size of 15 cm in length and 3 mm in diameter.

Formulation Example 13

100 mg of any one of Compounds of Present Invention 1 to 23, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture is compressed to an appropriate size to obtain a tablet.

Formulation Example 14

25 mg of any one of Compounds of Present Invention 1 to 23, 60 mg of lactose, 25 mg of corn starch, 6 mg of carmellose calcium and an appropriate amount of 5% hydroxypropyl methylcellulose are mixed, and the resulting mixture is filled into a hard shell gelatin capsule or a hydroxypropyl methylcellulose capsule to obtain an encapsulated formulation.

Formulation Example 15

Distilled water is added to 1000 mg of any one of Compounds of Present Invention 1 to 23, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co.), 35 mg of flavor and 500 mg of colorant, such that the final volume is 100 ml, and the mixture is mixed to obtain a suspension for oral administration.

Formulation Example 16

5 parts of any one of Compounds of Present Invention 1 to 23 is dissolved in 5 parts of polysorbate 85, 3 parts of benzyl alcohol and 30 parts of propylene glycol, and a phosphate buffer is added to this solution so as to have a pH of 6.0 to 6.5, then water is added until the total amount is 100 parts to obtain a liquid formulation for oral administration.

Formulation Example 17

5 parts of aluminum distearate is dispersed in 57 parts of fractionated palm oil and 3 parts of polysorbate 85 by heating. 25 parts of saccharin is dispersed in an oily vehicle obtained by cooling this dispersion to room temperature. Further, 10 parts of any one of Compounds of Present Invention 1 to 23 is added thereto to obtain a paste formulation for oral administration.

Formulation Example 18

5 parts of any one of Compounds of Present Invention 1 to 23 and 95 parts of limestone powder are mixed, and a granule for oral administration is obtained using wet granulation method.

Formulation Example 19

5 parts of any one of Compounds of Present Invention 1 to 23 is dissolved in 80 parts of diethylene glycol monoethyl ether, and 15 parts of propylene carbonate is mixed therewith to obtain a spot-on solution.

Formulation Example 20

10 parts of any one of Compounds of Present Invention 1 to 23 is dissolved in 70 parts of diethylene glycol monoethyl ether, and 20 parts of 2-octyl dodecanol is mixed therewith to obtain a pour-on solution.

Formulation Example 21

60 parts of NIKKOL TEALS-42 (Nikko Chemicals Co., Ltd., 42% aqueous solution of triethanolamine lauryl sulfate) and 20 parts of propylene glycol are added to 0.5 parts of any one of Compounds of Present Invention 1 to 23, and the mixture is sufficiently stirred and mixed until it becomes a uniform solution, then 19.5 parts of water is added and further sufficiently stirred and mixed to obtain a shampoo agent as a uniform solution.

Formulation Example 22

0.15 parts of any one of Compounds of Present Invention 1 to 23, 95 parts of an animal feed and 4.85 parts of a mixture of dibasic calcium phosphate, diatomaceous earth, Aerosil and carbonate (or chalk) are sufficiently stirred and mixed to obtain a feed premix for animal.

Formulation Example 23

7.2 g of any one of Compounds of Present Invention 1 to 23 and 92.8 g of VOSCO S-55 (manufactured by Maruishi Pharmaceutical Co., Ltd.) are dissolved and mixed at 100° C., poured into a suppository mold, and cooled and solidified to obtain a suppository.

Next, the pest control effect of the compound of the present invention is shown as test examples.

Test Example 1

Each of the formulations of Compounds of Present Invention 1, 7, 19, 21 and 23 obtained in Formulation Example 5 was diluted with water so as to have a concentration of the active ingredient of 500 ppm to prepare a test drug solution.

On the other hand, a cucumber seedling (the first true leaf stage) planted in a plastic cup was inoculated with about 30 *Aphis gossypii*, and leaving it for a day. 20 ml of the test drug solution was sprayed on the seedling.

Six days after spraying, the number of the surviving *Aphis gossypii* parasitized on the leaves of the cucumber was examined, and the control value was calculated according to the following equation:

Controlling value(%)={1−(Cb×Tai)/(Cai×Tb)}×100 wherein the symbols represent as follows:
Cb: the number of insects in a non-treated section before treatment
Cai: the number of insects in a non-treated section on observation
Tb: the number of insects in a treated section before treatment
Tai: the number of insects in a treated section on observation
wherein the non-treated section refers to a section where the test drug solution prepared by diluting the formulation not containing the compound of the present invention as in Formulation Example 5 with the same amount of water as in the treated section was sprayed.

As a result, in the treated section using each test drug solution of Compounds of Present Invention 1, 7, 19, 21 and 23, the control value was 90% or more.

Test Example 2

The formulation of Compound of Present Invention 19 as obtained in Formulation Example 5 was diluted with water, so as to have a concentration of the active ingredient of 500 ppm, to prepare a test drug solution.

On the other hand, a cucumber seedling (the second true leaf stage) planted in a plastic cup was drenched at its foot with 5 ml of the test drug solution, and kept in a greenhouse at 25° C. for 7 days. The cucumber leaf surface was inoculated with 30 *Aphis gossypii* (whole stage), and further kept in the greenhouse for 6 days, then the number of living *Aphis gossypii* parasitized on the leaves of the cucumber was examined, and the control value was calculated according to the following equation, then adequate results were obtained.

Controlling value(%)={1−(Cb×Tai)/(Cai×Tb)}×100 wherein the symbols represent as follows:
Cb: the number of insects in a non-treated section before treatment
Cai: the number of insects in a non-treated section on observation
Tb: the number of insects in a treated section before treatment
Tai: the number of insects in a treated section on observation
wherein the non-treated section refers to a section where the test drug solution prepared by diluting the formulation not containing the compound of the present invention as in Formulation Example 5 with the same amount of water as in the treated section was sprayed.

As a result, in the treated section using the test drug solution of Compound of Present Invention 19, the control value was 90% or more.

Test Example 3

Each of the formulations of Compounds of Present Invention 1, 19, 21, 22 and 23 as obtained in Formulation Example 5 was diluted with water, so as to have a concentration of the active ingredient of 500 ppm, to prepare a test drug solution.

To a rice seedling in the second leaf stage planted in a polyethylene cup was sprayed 10 ml of each test drug solution. After air-drying, 20 third-fourth instar larvae of *Nilaparvata lugens* were released, and kept in the greenhouse at 25° C. After 6 days, the number of *Nilaparvata lugens* parasitized on the rice was examined, and the control value was calculated according to the following equation:

Controlling value(%)={1−($Cb \times Tai$)/($Cai \times Tb$)}×100 wherein the symbols represent as follows:

Cb: the number of insects in a non-treated section before treatment

Cai: the number of insects in a non-treated section on observation

Tb: the number of insects in a treated section before treatment

Tai: the number of insects in a treated section on observation wherein the non-treated section refers to a section where the test drug solution prepared by diluting the formulation not containing the compound of the present invention as in Formulation Example 5 with the same amount of water as in the treated section was sprayed.

As a result, in the treated section using each test drug solution of Compounds of Present Invention 1, 19, 21, 22 and 23, the control value was 90% or more.

Test Example 4

Each of the formulations of Compounds of Present Invention as obtained in Formulation Example 5 is diluted with water, so as to have a concentration of the active ingredient of 500 ppm, to prepare a test drug solution.

On the other hand, a rice seedling (2 weeks after sowing, the second leaf stage) planted in a plastic cup is drenched at its foot with 5 ml of each test drug solution, and kept in a greenhouse at 25° C. for 7 days. 20 third-fourth instar larvae of *Nilaparvata lugens* are released, and further kept in the greenhouse for 6 days, then the number of living *Nilaparvata lugens* parasitized on the leaves of the rice is examined, and the control value is calculated according to the following equation, then adequate results are obtained.

Controlling value(%)={1−($Cb \times Tai$)/($Cai \times Tb$)}×100 wherein the symbols represent as follows:

Cb: the number of insects in a non-treated section before treatment

Cai: the number of insects in a non-treated section on observation

Tb: the number of insects in a treated section before treatment

Tai: the number of insects in a treated section on observation wherein the non-treated section refers to a section where the test drug solution prepared by diluting the formulation not containing the compound of the present invention as in Formulation Example 5 with the same amount of water as in the treated section is sprayed.

As a result, in the treated section using each test drug solution of Compounds of Present Invention, adequate control value is obtained.

Test Example 5

Each of the formulations of Compounds of Present Invention as obtained in Formulation Example 5 is diluted with water, so as to have a concentration of the active ingredient of 500 ppm, to prepare a test drug solution.

On the other hand, adult *Bemisia tabaci* is released on a tomato seedling (the third true leaf stage) planted in a polyethylene cup, and made to lay eggs for about 72 hours. The tomato seedling is kept in a greenhouse for 8 days, and when instar larvae hatch from the eggs, the above test drug solution is sprayed at a rate of 20 ml/cup, and the cup is kept in a greenhouse at 25° C. After 7 days, the number of surviving instar larvae on the tomato leaves is examined, and the control value is calculated according to the following equation:

Controlling value(%)={1−($Cb \times Tai$)/($Cai \times Tb$)}×100 wherein the symbols represent as follows:

Cb: the number of insects in a non-treated section before treatment

Cai: the number of insects in a non-treated section on observation

Tb: the number of insects in a treated section before treatment

Tai: the number of insects in a treated section on observation wherein the non-treated section refers to a section where the test drug solution prepared by diluting the formulation without the compound of the present invention as in Formulation Example 5 with the same amount of water as in the treated section is sprayed.

As a result, in the treated section using each test drug solution of the compounds of the present invention, adequate control value is obtained.

Test Example 6

Each of the formulations of Compounds of Present Invention 1 to 5, 7, 8, 19, 21, 22 and 23 as obtained in Formulation Example 5 was diluted with water, so as to have a concentration of the active ingredient of 500 ppm, to prepare a test drug solution.

On the other hand, to cabbage at the third leaf stage planted in a polyethylene cup was sprayed the test drug solution at a rate of 20 mL/cup. After the drug solution was dried, the foliage part was cut off, and then placed in a 50 mL volume cup. Five second instar larvae of *Plutella xylostella* were released into the cup, and the cup was sealed with a lid. The cup was kept at 25° C., and after 5 days, the number of living insects was counted. The death rate was calculated according to the following equation:

Death rate(%)=(Number of dead insects/Number of tested insects)×100

As a result, in the treated section using each test drug solution of Compounds of Present Invention 1 to 5, 7, 8, 19, 21, 22 and 23, the death rate was 80% or more.

Test Example 7

Each of the formulations of Compounds of Present Invention 3, 5, 7, 8, 19, 21, 22 and 23 as obtained in Formulation Example 5 was diluted with water, so as to have a concentration of the active ingredient of 500 ppm, to prepare a test spray solution.

On the other hand, an apple tree was planted in a plastic cup, and grown until the seventh-eighth true leaf was spread. To the apple tree was sprayed the test drug solution at a rate of 20 mL/cup. After the drug solution was dried, 60 first-instar larvae of *Adoxophyes orana fasciata* were released, the cup was covered with a plastic cup upside-down in which the bottom was cut off, and a filter paper was put thereon. After 7 days, the number of living insects was counted, and the death rate was calculated according to the following equation:

Death rate(%)=(Number of dead insects/Number of tested insects)×100

As a result, in the treated section using each test drug solution of Compounds of Present Invention 3, 5, 7, 8, 19, 21, 22 and 23, the death rate was 90% or more.

Test Example 8

Each of the formulations of Compounds of Present Invention as obtained in Formulation Example 5 is diluted with water, so as to have a concentration of the active ingredient of 500 ppm, to prepare a test drug solution.

A filter paper having a diameter of 5.5 cm is spread on the bottom of a polyethylene cup having the same diameter, 0.7 ml of the test drug solution is added dropwise onto the filter paper, and 30 mg of sucrose is uniformly placed as bait. Into the polyethylene cup, 10 female imagoes of *Musca domestica* are released, and the cup is sealed with a lid. After 24 hours, the life and death of *Musca domestica* is examined, and the death rate is calculated.

As a result, the adequate death rate is obtained in the treated section using the test drug solution of the compound of the present invention.

Test Example 9

Each of the formulations of Compounds of Present Invention as obtained in Formulation Example 5 is diluted with water, so as to have a concentration of the active ingredient of 500 ppm, to prepare a test drug solution.

A filter paper having a diameter of 5.5 cm is spread on the bottom of a polyethylene cup having the same diameter, 0.7 ml of the test drug solution is added dropwise onto the filter paper, and 30 mg of sucrose is uniformly placed as bait. Into the polyethylene cup, 2 male imagoes of *Blattella germanica* are released, and the cup is sealed with a lid. After 6 days, the life and death of *Blattella germanica* is examined, and the death rate is calculated.

As a result, the adequate death rate is obtained in the treated section using the test drug solution of the compound of the present invention.

Test Example 10

Each of the formulations of Compounds of Present Invention 1, 7 and 21 as obtained in Formulation Example 5 was diluted with water, so as to have a concentration of the active ingredient of 500 ppm, to prepare a test drug solution.

0.7 ml of the test drug solution was added to 100 ml of ion-exchanged water (active ingredient concentration: 3.5 ppm). Twenty last-instar larvae of *Culex pipiens pallens* were released into the solution. One day after, the life and death of the *Culex pipiens pallens* was examined, and the death rate was calculated.

As a result, in the treatment with Compounds of Present Invention 1, 7 and 21, the death rate was 91% or more.

Test Example 11

2 mg of Compound of Present Invention 1 was weighed in a screw tube (Maruemu No. 5; 27×55 mm), 0.2 mL of acetone was added thereto, and the screw tube was sealed with a cap to dissolve the compound. The screw tube was rotated and inverted to uniformity coat the whole inner wall of the tube with the drug solution. After removing the cap, the solution was air-dried for about 2 hours, then non-blood-sucking nymphal ticks, *Haemaphysalis longicornis* (5 ticks/group) were released, and the tube was sealed with the cap. After 2 days, the number of dead ticks was examined, and the death rate was calculated according to the following equation:

Death rate(%)=100×(Number of dead ticks/Number of tested ticks)

As a result, in the treatment with Compound of Present Invention 1, the death rate was 100%.

INDUSTRIAL APPLICABILITY

The compound of the present invention has a controlling effect on pests and is useful as an active ingredient of a pest control agent.

The invention claimed is:
1. A fused heterocyclic compound represented by formula (C-1) or an N-oxide thereof,

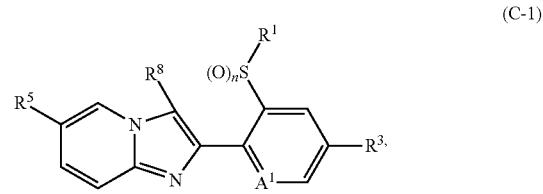

wherein
$A^1$ represents a nitrogen atom or $CR^7$;
$R^1$ represents a C1 to C6 chain hydrocarbon group optionally substituted with one or more atoms or groups selected from the group consisting of halogen atoms and cyclopropyl groups (wherein the cyclopropyl group is optionally substituted with one or more halogen atoms or one or more C1 to C3 alkyl groups), a C2 to C6 alkenyl group optionally substituted with one or more halogen atoms, a C2 to C6 alkynyl group optionally substituted with one or more halogen atoms, or a C3 to C6 cycloalkyl group optionally substituted with one or more halogen atoms or one or more C1 to C3 alkyl groups;
$R^3$ represents a C1 to C6 alkyl group optionally substituted with one or more halogen atoms, a C2 to C6 alkenyl group optionally substituted with one or more halogen atoms, a C2 to C6 alkynyl group optionally substituted with one or more halogen atoms, a 5- or 6-membered aromatic heterocyclic group (wherein the 5- or 6-membered aromatic heterocyclic group is optionally substituted with one or more atoms or groups selected from the group consisting of halogen atoms, C1 to C3 alkyl groups optionally substituted with a halogen atom and C1 to C3 alkoxy groups optionally substituted with a halogen atom), $-OR^{12}$, $-S(O)_m R^{12}$, a cyano group, a nitro group, a halogen atom, or a hydrogen atom;
$R^5$ represents a C1 to C6 alkyl group optionally substituted with one or more halogen atoms, $-OR^{14}$, $-S(O)_m R^{14}$, $-SF_5$, or a halogen atom;
$R^7$ is a halogen atom or a hydrogen atom;
$R^8$ represents a C1 to C6 alkyl group optionally substituted with one or more halogen atoms, a halogen atom, or a hydrogen atom;
$R^{12}$ and $R^{14}$ are the same or different and represent a C1 to C6 alkyl group optionally substituted with one or more halogen atoms;

each m independently represents 0, 1, or 2; and
n represents 0, 1, or 2
when m is 1 or 2 in —S(O)$_m$R$^{12}$, R$^{12}$ does not represent a hydrogen atom; and when m is 1 or 2 in —S(O)$_m$R$^{14}$, R$^{14}$ does not represent a hydrogen atom.

2. The fused heterocyclic compound according to claim 1, wherein R$^1$ is an ethyl group or a cyclopropylmethyl group; R$^7$ is a hydrogen atom;
R$^3$ is a C1 to C6 alkyl group optionally having one or more halogen atoms, —OR$^{12}$, S(O)$_m$R$^{12}$, a halogen atom, or a hydrogen atom;
R$^5$ is a C1 to C6 haloalkyl group, —OR$^{14}$ (wherein R$^{14}$ is a C1 to C6 haloalkyl group), —S(O)$_m$R$^{14}$ (wherein R$^{14}$ is a C1 to C6 haloalkyl group, and m is 0, 1, or 2), SF$_5$, or a halogen atom; and
R$^8$ is a methyl group, a hydrogen atom, or a halogen atom.

3. A pest control composition comprising the fused heterocyclic compound as defined in claim 1, and an inert carrier.

4. A method for controlling pests comprising applying an effective amount of the fused heterocyclic compound as defined in claim 1 to a pest or a place where a pest inhabits.

5. The fused heterocyclic compound according to claim 1, wherein A$^1$ is a nitrogen atom.

6. The fused heterocyclic compound according to claim 1, wherein A$^1$ is CR$^7$.

\* \* \* \* \*